US011633477B2

(12) United States Patent
Koizumi et al.

(10) Patent No.: US 11,633,477 B2
(45) Date of Patent: Apr. 25, 2023

(54) TREATMENT OF CORNEA USING LAMININ

(71) Applicants: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

(72) Inventors: Noriko Koizumi, Kyotanabe (JP); Naoki Okumura, Kyotanabe (JP); Shigeru Kinoshita, Kyoto (JP)

(73) Assignees: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

(*) Notice: Subject to any disclaimer, the term of this patent is extended or adjusted under 35 U.S.C. 154(b) by 28 days.

(21) Appl. No.: 15/523,231

(22) PCT Filed: Oct. 30, 2015

(86) PCT No.: PCT/JP2015/005473
§ 371 (c)(1),
(2) Date: Apr. 28, 2017

(87) PCT Pub. No.: WO2016/067628
PCT Pub. Date: May 6, 2016

(65) Prior Publication Data
US 2017/0319693 A1 Nov. 9, 2017

(30) Foreign Application Priority Data
Oct. 31, 2014 (JP) .............................. JP2014-222947

(51) Int. Cl.
*A61K 45/00* (2006.01)
*A61K 31/4409* (2006.01)
*A61K 35/30* (2015.01)
*A61K 38/39* (2006.01)
*A61K 35/44* (2015.01)
*A61K 31/137* (2006.01)

(52) U.S. Cl.
CPC .......... *A61K 45/05* (2013.01); *A61K 31/4409* (2013.01); *A61K 35/30* (2013.01); *A61K 35/44* (2013.01); *A61K 38/39* (2013.01); *A61K 45/00* (2013.01); *A61K 31/137* (2013.01)

(58) Field of Classification Search
None
See application file for complete search history.

(56) References Cited

U.S. PATENT DOCUMENTS

| 6,153,593 | A | * | 11/2000 | Burgeson | ............... A61K 38/39 |
| | | | | | 424/443 |
| 6,693,169 | B1 | * | 2/2004 | Brunken | ............... C07K 14/78 |
| | | | | | 530/350 |
| 6,933,273 | B2 | | 8/2005 | Tryggvason et al. | |
| 2002/0142954 | A1 | * | 10/2002 | Burgeson | ............... C07K 14/78 |
| | | | | | 514/17.7 |
| 2004/0106646 | A1 | | 6/2004 | Takayama et al. | |
| 2005/0214259 | A1 | | 9/2005 | Sano et al. | |
| 2007/0092550 | A1 | * | 4/2007 | Lui | ....................... C12N 5/0621 |
| | | | | | 424/427 |
| 2007/0275365 | A1 | * | 11/2007 | Lui | ....................... C12N 5/0621 |
| | | | | | 435/1.3 |
| 2008/0131430 | A1 | | 6/2008 | Csaky et al. | |
| 2009/0306772 | A1 | * | 12/2009 | Tao | ........................... A61F 2/14 |
| | | | | | 623/4.1 |
| 2010/0028407 | A1 | | 2/2010 | Del Priore et al. | |
| 2010/0209402 | A1 | * | 8/2010 | Koizumi | .............. A61K 31/496 |
| | | | | | 424/93.7 |
| 2010/0233240 | A1 | * | 9/2010 | Koizumi | .................. A61L 27/24 |
| | | | | | 424/427 |
| 2011/0117062 | A1 | | 5/2011 | Klimanskaya et al. | |
| 2012/0156254 | A1 | | 6/2012 | Tryggvason et al. | |
| 2012/0282324 | A1 | | 11/2012 | Xing et al. | |
| 2012/0288482 | A1 | | 11/2012 | Takahashi et al. | |
| 2013/0195806 | A1 | * | 8/2013 | Gay | ........................... A61P 3/10 |
| | | | | | 424/93.7 |

(Continued)

FOREIGN PATENT DOCUMENTS

| CN | 1893988 A | 1/2007 |
| CN | 102597217 A | 7/2012 |

(Continued)

OTHER PUBLICATIONS

Davis, Regulation of Tissue Injury Responses by the Exposure of Matricryptic sites within Extracellular Matrix Molecules, American Journal of Pathology, vol. 156, No. 5, May 2000 (Year: 2000).*
LM332, Human Laminin 332, Kerafast Catalog page, 2019 (Year: 2019).*
Kaufman, The corneal endothelium in intraocular surgery, Journal of the Royal society of Medicine, vol. 73, Mar. 1980 (Year: 1980).*
Fuch's dystrophy, Medline Plus article, Apr. 5, 2015 (Year: 2015).*
Colby, Medical Treatment of Fuch's Dystrophy in our lifetime, Research highlight, The Association for Research in Vision and Ophthalmology, Inc., IOVS (Year: 2013).*
Takizawa (Mechanistic basis for the recognition of laminin-511 by α6β1 integrin, Sci. Adv. 2017, 3:e1701497 (Year: 2017).*
Laminin, Novus Biologicals, Catalog, Webpage (Year: 2022).*
Definition of "suspension", accessed online on Aug. 26, 2022 at: https://www.thoughtco.com/definition-of-suspension-605714 (Year: 2022).*

(Continued)

*Primary Examiner* — Robert J Yamasaki
(74) *Attorney, Agent, or Firm* — Leydig, Voit & Mayer, Ltd.

(57) ABSTRACT

The present invention provides a technique for treating the cornea. More specifically, the present invention is an agent for the treatment or prevention of a state of corneal endothelial disease, the agent including at least one factor selected from the group consisting of laminin and fragments thereof, wherein the problem is solved by also providing a technique characterized in that this agent is administered together with corneal endothelial cells. Specifically, the present invention can include laminin 511 (α5β1γ1), laminin 521 (α5β2γ1), or a fragment of these.

15 Claims, 14 Drawing Sheets

Specification includes a Sequence Listing.

(56) References Cited

U.S. PATENT DOCUMENTS

| | | | |
|---|---|---|---|
| 2014/0170751 A1* | 6/2014 | Hayashi | C12N 5/0621 435/377 |
| 2014/0341864 A1 | 11/2014 | Nakano et al. | |
| 2014/0370007 A1* | 12/2014 | McCabe | A61K 35/30 424/133.1 |
| 2015/0025452 A1* | 1/2015 | Marinkovich | A61Q 7/00 514/20.7 |
| 2017/0002318 A1 | 1/2017 | Koizumi et al. | |
| 2017/0319665 A1 | 11/2017 | Koizumi et al. | |
| 2020/0138868 A1* | 5/2020 | Thon | A61K 9/127 |

FOREIGN PATENT DOCUMENTS

| | | |
|---|---|---|
| CN | 102770136 A | 11/2012 |
| CN | 103384679 A | 11/2013 |
| CN | 103931608 A | 7/2014 |
| CN | 103937738 A | 7/2014 |
| EP | 2193806 A1 | 6/2010 |
| EP | 2487236 A1 | 8/2012 |
| EP | 2733201 A1 | 5/2014 |
| JP | 2013-128474 A | 7/2013 |
| RU | 2418067 C1 | 5/2011 |
| WO | WO 2000/066731 A2 | 11/2000 |
| WO | WO 2005/037144 A2 | 4/2005 |
| WO | WO 2007/091790 A1 | 8/2007 |
| WO | WO 2012/173207 A1 | 12/2012 |
| WO | WO 2013/012087 A1 | 1/2013 |
| WO | WO 2014/087244 A2 | 6/2014 |
| WO | WO 2015/053375 A1 | 4/2015 |

OTHER PUBLICATIONS

Caissie et al., "In vivo enhancement of sensory perception recovery in a tissue-engineered skin enriched with laminin," *Biomaterials*, 27: 2988-2993 (2006).

Liebkind et al., "Is the Soluble KDI Domain of γ1 Laminin a Regeneration Factor for the Mammalian Central Nervous System?" *J. Neurosci. Res.*, 73: 637-643 (2003).

McMillan et al., "Colocalization of Multiple Laminin Isoforms Predominantly beneath Hemidesmosomes in the Upper Lamina Densa of the Epidermal Basement Membrane," *J. Histochem. Cytochem.*, 54(1): 109-118 (2006).

Menezes et al., "Polylaminin, a polymeric form of laminin, promotes regeneration after spinal cord injury," *FASEB J.*, 24: 4513-4522 (2010).

Plantman et al., "Integrin-laminin interactions controlling neurite outgrowth from adult DRG neurons in vitro," *Mol. Cell. Sci.*, 39: 50-62 (2008).

Chinese Patent Office, Second Office Action in Chinese Patent Application No. 201480065134.X (dated Jul. 3, 2019).

Mexican Patent Office, Office Action in Mexican Patent Application No. MX/a/2016/006915 (dated Jun. 20, 2019).

Russian Patent Office, Official Action in Russian Patent Application No. 2017118405 (dated May 31, 2019).

Kakutani et al., "The efficiency of laminin-511 and laminin-521 as extracellular matrix for human corneal endothelial cell culture," *Invest. Ophthalmol. Vis. Sci.*, 55: E-Abstract 2055-C0074 (2014).

Yamaguchi et al., "Adhesion, Migration, and Proliferation of Cultured Human Corneal Endothelial Cells by Laminin-5," *Invest. Ophthalmol. Vis. Sci.*, 52(2): 679-684 (2011).

European Patent Office, Extended European Search Report in European Patent Application No. 15854129.2 (dated May 4, 2018).

Aumailley et al., "A simplified laminin nomenclature," *Matrix Biol.*, 24: 326-332 (2005).

Doi et al., "Recombinant Human Laminin (α5β1γ1)," *J. Biol. Chem.*, 277(15): 12741-12748 (2002).

Engelmann et al., "Isolation and Long-Term Cultivation of Human Corneal Endothelial Cells," *Invest. Opthalmol. Vis. Sci.*, 29(11): 1656-1662 (1988).

Miyazaki et al., "Laminin E8 fragments support efficient adhesion and expansion of dissociated human pluripotent stem cells," *Nat. Commun.*, 3: 1236 (2012).

Okamoto et al., "Chapter 3 Strategies Toward Clinical Uses and Front-Line—Toward Drug Discovery and Establishment of Multicellular Bodies", *Experimental Medicine*, 30(10): 1646-1650 (2012).

European Patent Office, Communication pursuant to Article 94(3) EPC in European Patent Application No. 14831100.4 (dated May 12, 2017).

European Patent Office, Communication Pursuant to Article 94(3) EPC in European Patent Application No. 14831100.4 (dated Mar. 28, 2018).

European Patent Office, Communication Pursuant to Article 94(3) EPC in European Patent Application No. 14831100.4 (dated Dec. 18, 2018).

European Patent Office, Communication Pursuant to Rule 164(1) EPC in European Patent Application No. 15854105.2 (dated Jun. 11, 2018).

Japanese Patent Office, International Search Report in International Patent Application No. PCT/JP2014/081917 (dated Apr. 1, 2015).

Japanese Patent Office, International Search Report in International Patent Application No. PCT/JP2015/005474 (dated Dec. 8, 2015).

Japanese Patent Office, Official Action in Japanese Patent Application No. 2016-535065 (dated Aug. 27, 2018).

Russian Patent Office, Official Action in Russian Patent Application No. 2016125225 (dated May 28, 2018).

Russian Patent Office, Search Report in Russian Patent Application No. 2016125225 (dated May 28, 2018).

Russian Patent Office, Official Action in Russian Patent Application No. 2016125225 (dated Sep. 5, 2018).

Li et al., "Relevance Between Proliferation of Corneal Endothelial Cell and Cytoskeleton Under the Action of Laminin," *Ophthalmic Research*, 23(1): 29 (2005).

Chinese Patent Office, First Office Action in Chinese Patent Application No. 201480065134X (dated Feb. 3, 2019).

Chinese Patent Office, Search Report in Chinese Patent Application No. 201480065134X (dated Feb. 3, 2019).

Russian Patent Office, Notification of Official Action in Russian Patent Application No. 2016125225 (dated Jan. 22, 2019).

Koizumi, "Development of New Therapeutic Modalities for Corneal Endothelial Disease Using Somatic Stem Cells", *Journal of Clinical and Experimental Medicine*, 241(10): 765-770 (2012).

Numata et al., "Usefulness of Laminins 511 and 521 as Culture Substrates for Human Endothelial Cells", *Japan Cornea Conference 2014: 38th Japan Cornea Society and 30th Annual Meeting of Keratoplasty Society of Japan Program Shorokushu*, p. 82, abstract 038 (Jan. 31, 2014).

Okumura et al., "Usefulness of Laminins 511 and 521 in Culture of Corneal Endothelial Cells", *Regenerative Medicine*, 13 (Suppl. 2014): 243, abstract O-44-1 (Jan. 27, 2014).

Sekiguchi et al., "Laminin-511 E8 Fragment as a Culture Substrate for Human Pluripotent Stem Cells Under Feeder-Free/Xeno-Free Conditions", *Clinical Evaluation*, 41(1): 124-127 (2013).

Sekiguchi et al., "Fundamental Technique for the Spread of Regenerative Medicine", *Saishin Igaku*, 69: 685-697 (Mar. 2014).

Ueno et al., "Realization of Regenerative Medicine for Corneal Endothelium by Transplantation of Cultured Human Corneal Endothelial Cells", *Inflammation and Immunology*, 21(2): 131-135 (2013).

Japanese Patent Office, International Search Report in International Patent Application No. PCT/JP2015/005473 (dated Dec. 8, 2015).

Deutzmann et al., "Cell adhesion, spreading and neurite stimulation by laminin fragment E8 depends on maintenance of secondary and tertiary structure in its rod and globular domain," *Eur. J. Biochem.*, 191: 513-522 (1990).

Europen Patent Office, Communication Pursuant to Article 94(3) EPC in European Patent Application No. 15854105.2 (dated Oct. 14, 2019).

Huang et al., "A Hierarchy of Endothelial Colony-Forming Cell Activity Displayed by Bovine Corneal Endothelial Cells," *Invest. Ophthalmol. Vis. Sci.*, 51(8): 3943-3949 (2010).

Okumura et al., "Laminin-511 and -521 Enable Efficient In Vitro Expansion of Human Corneal Endothelial Cells," *Invest. Ophthalmol. Vis. Sci.*, 56(5): 2933-2942 (2015).

(56) References Cited

OTHER PUBLICATIONS

Brazilian Patent Office, Office Action in Brazilian Patent Application No. BR112016011096-0 (dated Nov. 4, 2019).
Japanese Patent Office, Office Action in Japanese Patent Application No. 2016-556373 (dated Aug. 2, 2019).
Japanese Patent Office, Office Action in Japanese Patent Application No. 2016-556374 (dated Aug. 2, 2019).
Bystrom et al., "Distribution of Laminins in the Developing Human Eye," *Invest. Ophthalmol Vis. Sci.*, 47(3): 777-785 (2006).
Osumi et al., "Concise Review: Pax6 Transcription Factor Contributes to both Embryonic and Adult Neurogenesis as a Multifunctional Regulator," *Stem Cells*, 26(7): 1663-1672 (2008).
Powell et al., "Neuronal Laminins and their Cellular Receptors," *Int. J. Biochem. Cell Biol.*, 29(3): 401-414 (1997).
Japanese Patent Office, Notice of Reasons for Refusal in Japanese Patent Application No. 2016-556374 (dated Mar. 3, 2020).
Miner et al., "Laminin Functions in Tissue Morphogenesis," *Annu. Rev. Cell Dev. Biol.*, 20: 255-284 (2004).
Brazilian Patent Office, Preliminary Office Action in Brazilian Patent Application No. BR112017008805-3 (dated Aug. 13, 2020).
China National Intellectual Property Administration, Second Office Action in Chinese Patent Application No. 201580059642.1 (dated Sep. 2, 2020).
Mexican Patent Office, Office Action in Mexican Patent Application No. MX/a/2017/005522 (dated Sep. 17, 2020).
European Patent Office, Communication Pursuant to Article 94(3) EPC in European Patent Application No. 15854105.2 (dated May 12, 2020).
Taniguchi et al., "The C-terminal Region of Laminin β Chains Modulates the Integrin Binding Affinities of Laminins," *J. Biol. Chem.*, 284(12): 7820-7831 (2009).
China National Intellectual Property Administration, First Office Action and Search Report in Chinese Patent Application No. 201580059642.1 (dated Feb. 3, 2020).
European Patent Office, Communication Pursuant to Article 94(3) EPC in European Patent Application No. 15854129.2 (dated Jan. 28, 2020).
Japanese Patent Office, Final Office Action in Japanese Patent Application No. 2016-556373 (dated Mar. 3, 2020).
Yan et al., "III. Repair of Corneal endothelial Wound," *Ocular Physiology*, 46-47 (Dec. 31, 2001).
Zheng, "VI. Research progress of corneal endothelial transplantation," *Ophthalmological Clinical Theory and Practice*, 87-88 (Oct. 31, 1998).
China National Intellectual Property Administration, Third Office Action in Chinese Patent Application No. 201580059642.1 (dated Jan. 4, 2021).
Japanese Patent Office, Inquiry in Appeal No. 2020-7637 for Japanese Patent Application No. 2016-556373 (Apr. 9, 2021).
Japanese Patent Office, Notice of Reasons for Rejection in Appeal No. 2020-7637 for Japanese Patent Application No. 2016-556373 (dated Apr. 9, 2021).
European Patent Office, Communication Pursuant to Article 94(3) EPC in European Patent Application No. 15854129.2 (dated Mar. 9, 2021).
China National Intellectual Property Administration, Decision of Rejection in Chinese Patent Application No. 201580059642.1 (dated Apr. 21, 2021).
Mexican Patent Office, Office Action in Mexican Patent Application No. MX/a/2017/005522 (dated Apr. 15, 2021).
Edwards et al., "Laminins and retinal vascular development," *Cell Adhesion and Migration*, 7(1): 82-89 (2013).
Suzuki et al., "Functional Sites in the Laminin Alpha Chains," *Connective Tissue Research*, 46(3): 142-152 (2005).
Japanese Patent Office, Decision of Refusal in Japanese Patent Application No. 2020-097055 (dated Feb. 15, 2022).
U.S. Appl. No. 15/100,147, filed May 27, 2016.
U.S. Appl. No. 15/523,282, filed Apr. 28, 2017.
Canadian Patent Office, Examination Report and Search Report in Canadian Patent Application No. 2,965,770 (dated Oct. 20, 2021).
Japanese Patent Office, Notice of Reasons for Refusal in Japanese Patent Application No. 2020-097055 (dated Oct. 6, 2021).
Farina et al., "Temporal proteomic profiling of embryonic stem cell secretome during cardiac and neural differentiation," *Proteomics*, 11(20): 3972-3982 (2011).
Gospodarowicz et al., "The Production and Localization of Laminin in Cultured Vascular and Corneal Endothelial Cells," *J. Cell. Phys.*, 107(2): 171-183 (1981).
Okumura et al., "Enhancement on Primate Corneal Endothelial Cell Survival In Vitro by a Rock Inhibitor," *Invest. Ophthalmol. Vis. Sci.*, 50(8): 3680-3687 (2009).
Canadian Intellectual Property Office, Examiner Requisition in Canadian Patent Application No. 2,965,770 (dated Nov. 2, 2022).

* cited by examiner

Fig. 2 Change in corneal thickness after cultured cornea transplantation in rabbit bullous keratopathy model using laminin 511-E8 fragments Fig. 4 Effect of laminin on early cell adhesion in cultured corneal endothelium with concomitant use of ROCK inhibitor Fig. 6 Change in corneal thickness after cultured corneal endothelium transplantation in rabbit bullous keratopathy model with concomitant use of laminin and ROCK inhibitor Fig. 7 Change in ocular pressure after cultured corneal endothelium transplantation in rabbit bullous keratopathy model with concomitant use of laminin and ROCK inhibitor Fig. 9 Pictures of anterior ocular segment after cultured corneal endothelium transplantation in monkey bullous keratopathy model with concomitant use of laminin 511-E8

MCEC ($5.0 \times 10^5$ cells) + E8 fragment (2.1nM) + Y-27632 (100μM)

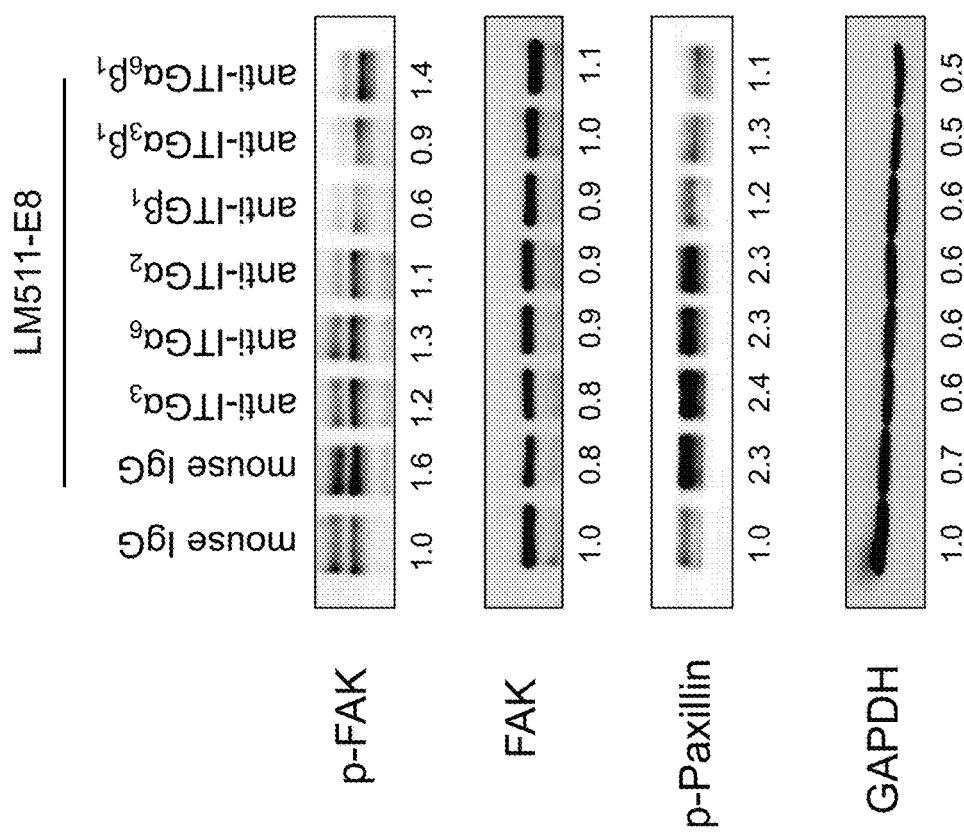
Fig. 14 Activation of cell adhesion associated proteins is mediated by integrin

SEQUENCE LISTING

```
<160> NUMBER OF SEQ ID NOS: 8

<210> SEQ ID NO 1
<211> LENGTH: 11445
<212> TYPE: DNA
<213> ORGANISM: Homo sapiens

<400> SEQUENCE: 1
agacccgccg ggctcccgcc gcgcgcgctg tccctggagc tcggggacgc ggcccggagc       60
cgggaagatg gcgaagcggc tctgcgcggg gagcgcactg tgtgttcgcg gccccgggg      120
```

-continued

```
cccegegeeg ctgctgctgg tegggctggc gctgctggge geggegeggg egeggagga    180 ggegggegge ggcttcagec tgcacccgcc ctacttcaac ctggccgagg cgcccgcat    240 cgccgcctcc gcgacctgcg gagaggaggc cccggcgcgc ggctcccgc gccccaccga    300 ggacctttac tgcaagctgg tagggggccc cgtggccggc ggcgacccca accagaccat    360
ccggggccag tactgtgaca tctgcacggc tgccaacagc aacaaggcac accccgcgag    420
caatgccatc gatggcacgg agcgctggtg gcagagtcca ccgctgtccc gcggcctgga    480
gtacaacgag gtcaacgtca ccctggacct gggccaggtc ttccacgtgg cctacgtcct    540
catcaagttt gccaactcac cccggccgga cctctgggtg ctggagcggt ccatggactt    600
cggccgcacc taccagccct ggcagttctt tgcctcctcc aagagggact gtctggagcg    660
gttcgggcca cagacgctgg agcgcatcac acgggacgac gcggccatct gcaccaccga    720
gtactcacgc atcgtgcccc tggagaacgg agagatcgtg gtgtccctgg tgaacggacg    780
tccgggcgcc atgaatttct cctactcgcc gctgctacgt gagttcacca aggccaccaa    840
cgtccgcctg cgcttcctgc gtaccaacac gctgctgggc catctcatgg ggaaggcgct    900
gcgggacccc acgtcacccg gccggtatta ttacagcatc aaggatatca gcatcggagg    960
ccgctgtgtc tgccacggcc acgcggatgc ctgcgatgcc aaagaccccca cggacccgtt   1020 caggctgcag tgcacctgcc agcacaaacac ctgcgggggc acctgcgacc gctgctgccc   1080
cggcttcaat cagcagccgt ggaagcctgc gactgccaac agtgccaacg agtgccagtc   1140
ctgtaactgc tacggccatg ccaccgactg ttactacgac cctgaggtgg accggcgccg   1200
cgccagccag agcctggatg gcacctatca gggtgggggt gtctgtatcg actgccagca   1260
ccacaccacc ggcgtcaact gtgagcgctg cctgcccggc ttctaccgct ctcccaacca   1320
ccctctcgac tcgccccacg tctgccgccg ctgcaactgc gagtccgact tcacggatgg   1380
cacctgcgag gacctgacgg gtcgatgcta ctgccggccc aacttctctg gggagcggtg   1440
tgacgtgtgt gccgagggct tcacgggctt cccaagctgc taccccgacgc cctcgtcctc   1500 caatgacacc agggagcagg tgctgccagc cggccagatt gtgaattgtg actgcagcgc   1560
ggcagggacc cagggcaacg cctgccggaa ggacccaagg gtgggacgct gtctgtgcaa   1620
acccaacttc caaggcaccc attgtgagct ctgcgcgcca gggttctacg gccccggctg   1680
ccagccctgc cagtgttcca gccctggagt ggccgatgac cgctgtgacc ctgacacagg   1740
ccagtgcagg tgccgagtgg gcttcgaggg ggccacatgt gatcgctgtg cccccggcta   1800
ctttcacttc cctctctgcc agttgtgtgg ctgcagccct gcaggaacct gcccgagggg   1860
ctgcgatgag gccggccgct gcctatgcca gcctgagttt gctggacctc attgtgaccg   1920
gtgccgccct ggctaccatg gtttccccaa ctgccaagca tgcacctgcg accctcgggg   1980
agccctggac cagctctgtg gggcgggagg tttgtgccgc tgccgccccg gctacacagg   2040
cactgcctgc caggaatgca gccccggctt tcacggcttc cccagctgtg tccctgcca   2100 ctgctctgct gaaggctccc tgcacgcagc ctgtgacccc cggagtgggc agtgcagctg   2160
ccggccccgt gtgacggggc tgcggtgtga cacatgtgtg cccggtgcct acaacttccc   2220
ctactgcgaa gctggctctt gccacccctgc cggtctggcc ccagtggatc ctgcccttcc   2280
tgaggcacag gttccctgta tgtgccgggc tcacgtggag gggccgagct gtgaccgctg   2340
caaacctggg ttctgggac tgagccccag caaccccgag gctgtaccc gctgcagctg   2400 cgacctcagg ggcacactgg gtggagttgc tgagtgccag ccgggcaccg ccagtgctt   2460 ctgcaagccc cacgtgtgcg gccaggcctg cgcgtcctgc aaggatggct ctttggact   2520
```

-continued

```
ggatcaggct gactattttg gctgccgcag ctgccggtgt gacattggcg gtgcactggg    2580
ccagagctgt gaaccgagga cgggcgtctg ccggtgccgc cccaacaccc agggccccac    2640
ctgcagcgag cctgcgaggg accactacct cccggacctg caccacctgc gcctggagct    2700
ggaggaggct gccacacctg agggtcacgc cgtgcgcttt ggcttcaacc ccctcgagtt    2760
cgagaacttc agctggaggg gctacgcgca gatggcacct gtccagccca ggatcgtggc    2820
caggctgaac ctgaccctcc ctgaccttt ctggctcgtc ttccgatacg tcaaccgggg    2880
ggccatgagt gtgagcgggc gggtctctgt gcgagaggag ggcaggtcgg ccacctgcgc    2940
caactgcaca gcacagagtc agcccgtggc cttcccaccc agcacggagc ctgccttcat    3000
caccgtgccc cagaggggct cggagagcc ctttgtgctg aaccctggca cctgggccct    3060
gcgtgtggag gccgaagggg tgctcctgga ctacgtggtt ctgctgccta gcgcatacta    3120
cgaggcggcg ctcctgcagc tgcgggtgac tgaggcctgc atataccgtc cctctgccca    3180
gcagtctggc gacaactgcc tcctctacac acacctcccc ctggatggct ccccctcggc    3240
cgccgggctg gaggccctgt gtcgccagga caacagcctg ccccggccct gccccacgga    3300
gcagctcagc ccgtcgcacc cgccactgat cacctgcacg ggcagtgatg tggacgtcca    3360
gcttcaagtg gcagtgccac agccaggccg ctatgcccta gtggtggagt acgccaatga    3420
ggatgcccgc caggaggtgg gcgtggccgt gcacacccca cagcgggccc ccagcaggg    3480 gctgctctcc ctgcacccct gcctgtacag caccctgtgc cggggcactg cccgggatac    3540
ccaggaccac ctggctgtct tccacctgga ctcggaggcc agcgtgaggc tcacagccga    3600
acaggcacgc ttcttcctgc acgggtcac tctggtgccc attgaggagt tcagcccgga    3660
gttcgtggag ccccgggtca gctgcatcag cagccacggc gcctttggcc caacagtgc    3720 cgcctgtctg ccctcgcgct tcccaaagcc gccccagccc atcatcctca gggactgcca    3780
ggtgatcccg ctgccgcccg gcctcccgct gacccacgcg caggatctca ctccagccat    3840
gtccccagct ggaccccgac ctcggccccc caccgctgtg gaccctgatg cagagcccac    3900
cctgctgcgt gagccccagg ccaccgtggt cttcaccacc catgtgccca cgctgggccg    3960
ctatgccttc ctgctgcacg gctaccagcc agccacccc accttccccg tggaagtcct    4020
catcaacgcc ggccgcgtgt ggcagggcca cgccaacgcc agcttctgtc cacatggcta    4080
cggctgccgc accctggtgg tgtgtgaggg ccaggccctg ctggacgtga cccacagcga    4140
gctcactgtg accgtgcgtg tgcccaaggg ccggtggctc tggctggatt atgtactcgt    4200
ggtccctgag aacgtctaca gctttggcta cctccgggag gagccctgg ataaatccta    4260 tgacttcatc agccactgcg cagcccaggg ctaccacatc agccccagca gctcatccct    4320
gttctgccga aacgctgctg cttccctctc cctcttctat aacaacggag cccgtccatg    4380
tggctgccac gaagtaggtg ctacaggccc cacgtgtgag cccttcgggg ccagtgtcc    4440 ctgccatgcc catgtcattg gccgtgactg ctccgctgt gccaccggat actgggcttt    4500
ccccaactgc aggccctgtg actgcggtgc ccgcctctgt gacgagctca cgggccagtg    4560 catctgccc caacgcacca tcccgcccga ctgcctgctg tgccagcccc agacctttgg    4620
ctgccacccc ctggtcggct gtgaggagtg taactgctca gggcccggca tccaggagct    4680
cacagaccct acctgtgaca cagacagcgg ccagtgcaag tgcagaccca acgtgactgg    4740
gcgccgctgt gatacctgct ctccgggctt ccatggctac cccgctgcc gccctgtga    4800 ctgtcacgag gcgggcactg cgcctggcgt gtgtgaccc ctcacagggc agtgctactg    4860
```

```
taaggagaac gtgcagggcc ccaaatgtga ccagtgcagc cttgggacct tctcactgga    4920
tgctgccaac cccaaaggtt gcacccgctg cttctgcttt ggggccacgg agcgctgccg    4980
gagctcgtcc tacacccgcc aggagttcgt ggatatggag ggatgggtgc tgctgagcac    5040
tgaccggcag gtggtgcccc acgagcggca gccaggacg gagatgctcc gtgcagacct    5100
gcggcacgtg cctgaggctg tgcccgaggc tttccccgag ctgtactggc aggccccacc    5160
ctcctacctg ggggaccggg tgtcatccta cggtgggacc ctccgttatg aactgcactc    5220
agagacccag cggggagatg tctttgtccc catggagagc aggccggatg tggtgctgca    5280
gggcaaccag atgagcatca cattcctgga gccggcatac cccacgcctg ccacgttca    5340 ccgtgggcag ctgcagctgg tggaggggaa cttccggcat acggagacgc gcaacactgt    5400
gtcccgcgag gagctcatga tggtgctggc cagcctggag cagctgcaga tccgtgccct    5460
cttctcacag atctcctcgg ctgtcttcct gcgcagggtg gcactggagg tggccagccc    5520
agcaggccag ggggccctgg ccagcaatgt ggagctgtgc ctgtgccccg ccagctaccg    5580
gggggactca tgccaggaat gtgccccccgg cttctatcgg gacgtcaaag gtctcttcct    5640
gggccgatgt gtcccttgtc agtgccatgg acactcagac cgctgcctcc ctggctctgg    5700
cgtctgtgtg gactgccagc acaacaccga aggggcccac tgtgagcgct gccaggctgg    5760
cttcgtgagc agcagggacg accccagcgc ccctgtgtc agctgcccct gcccctctc    5820 agtgccttcc aacaacttcg ccgagggctg tgtcctgcga ggcggccgca cccagtgcct    5880
ctgcaaacct ggttatgcag gtgcctcctg cgagcggtgt gcgcccggat tctttgggaa    5940
cccactggtg ctgggcagct cctgccagcc atgcgactgc agcggcaacg gtgaccccaa    6000
cttgctcttc agcgactgcg acccctgac gggcgcctgc cgtggctgcc tgcgccacac    6060
cactgggccc cgctgcgaga tctgtgcccc cggcttctac ggcaacgccc tgctgcccgg    6120
caactgcacc cggtgcgact gtaccccatg tgggacagag gcctgcgacc cccacagcgg    6180
gcactgcctg tgcaaggcgg gcgtgactgg cggcgctgt gaccgctgcc aggagggaca    6240
ttttggtttc gatggctgcg gggctgccg cccgtgtgct tgtggaccgg ccgccgaggg    6300
ctccgagtgc caccccaga gcggacagtg ccactgccga ccaggaccca tgggaccccca    6360 gtgccgcgag tgtgcccctg gctactgggg gctccctgag cagggctgca ggcgctgcca    6420
gtgccctggg ggccgctgtg accctcacac gggccgctgc aactgccccc cggggctcag    6480
cggggagcgc tgcgacacct gcagccagca gcatcaggtg cctgttccag gcgggcctgt    6540
gggccacagc atccactgtg aagtgtgtga ccactgtgtg gtcctgctcc tggatgacct    6600
ggaacgggcc ggcgccctcc tccccgccat tcacgagcaa ctgcgtggca tcaatgccag    6660
ctccatggcc tgggccgtc tgcacaggct gaacgcctcc atcgctgacc tgcagagcca    6720
gctccggagc cccctgggcc cccgccatga cacggcacag cagctggagg tgctggagca    6780
gcagagcaca agcctcgggc aggacgcacg gcggctaggc ggccaggccg tggggacccg    6840
agaccaggcg agccaattgc tggccggcac cgaggccaca ctgggccatg cgaagacgct    6900
gttggcggcc atccgggctg tggaccgcac cctgagcgag ctcatgtccc agacgggcca    6960
cctggggctg ccaatgcct cggctccatc aggtgagcag ctgctccgga cactggccga    7020
ggtggagcgg ctgctctggg agatgcgggc ccgggacctg ggggccccgc aggcagcagc    7080
tgaggctgag ttggctgcag cacagagatt gctggcccgg gtgcaggagc agctgagcag    7140
cctctgggag gagaaccagg cactggccac acaaacccgc gaccggctgg cccagcacga    7200
ggccggcctc atggacctgc gagaggcttt gaaccgggca gtggacgcca cacgggaggc    7260
```

```
ccaggagctc aacagccgca accaggagcg cctggaggaa gccctgcaaa ggaagcagga    7320
gctgtcccgg gacaatgcca ccctgcaggc cactctgcat gcggctaggg acaccctggc    7380
cagcgtcttc agattgctgc acagcctgga ccaggctaag gaggagctgg agcgcctcgc    7440
cgccagcctg gacggggctc ggaccccact gctgcagagg atgcagacct tctcccggc     7500
gggcagcaag ctgcgtctag tggaggccgc cgaggcccac gcacagcagc tgggccagct    7560
ggcactcaat ctgtccagca tcatcctgga cgtcaaccag gaccgcctca cccagagggc    7620
catcgaggcc tccaacgcct acagccgcat cctgcaggcc gtgcaggctg ccgaggatgc    7680
tgctggccag gccctgcagc aggcggacca cacgtgggcg acggtggtgc ggcagggcct    7740
ggtggaccga gcccagcagc tcctggccaa cagcactgca ctagaagagg ccatgctcca    7800
ggaacagcag aggctgggcc ttgtgtgggc tgccctccag ggtgccagga cccagctccg    7860
agatgtccgg gccaagaagg accagctgga ggcgcacatc caggcggcgc aggccatgct    7920
tgccatggac acagacgaga caagcaagaa gatcgcacat gccaaggctg tggctgctga    7980
agcccaggac accgccaccc gtgtgcagtc ccagctgcag gccatgcagg agaatgtgga    8040
gcggtggcag ggccagtacg agggcctgcg gggccaggac ctgggccagg cagtgcttga    8100
cgcaggccac tcagtgtcca ccctggagaa gacgctgccc cagctgctgg ccaagctgag    8160
catcctggaa aaccgtgggg tgcacaacgc cagcctggcc ctgtccgcca gcattggccg    8220
cgtgcgagag ctcattgccc aggcccgggg ggctgccagt aaggtcaagg tgcccatgaa    8280
gttcaacggg cgctcagggg tgcagctgcg caccccacgg gatcttgccg accttgctgc    8340
ctacactgcc ctcaagttct acctgcaggg cccagagcct gagcctgggc agggtaccga    8400
ggatcgcttt gtgatgtaca tgggcagccg ccaggccact ggggactaca tgggtgtgtc    8460
tctgcgtgac aagaaggtgc actgggtgta tcagctgggt gaggcgggcc ctgcagtcct    8520
aagcatcgat gaggacattg gggagcagtt cgcagctgtc agcctggaca ggactctcca    8580
gtttggccac atgtccgtca cagtggagag acagatgatc caggaaacca agggtgacac    8640
ggtggcccct ggggcagagg ggctgctcaa cctgcggcca gacgacttcg tcttctacgt    8700
cggggggtac cccagtacct tcacgccccc tcccctgctt cgcttcccccg ctaccggggg  8760
ctgcatcgag atggacacgc tgaatgagga ggtggtcagc ctctacaact tcgagaggac    8820
cttccagctg gacacggctg tggacaggcc ttgtgcccgc tccaagtcga ccggggaccc    8880
gtggctcacg gacggctcct acctggacgg caccggcttc gcccgcatca gcttcgacag    8940
tcagatcagc accaccaagc gcttcgagca ggagctgcgg ctcgtgtcct acagcggggt    9000
gctcttcttc ctgaagcagc agagccagtt cctgtgcttg gccgtgcaag aaggcagcct    9060
cgtgctgttg tatgactttg gggctggcct gaaaaaggcc gtcccactgc agcccccacc    9120
gccccctgacc tcggccagca aggcgatcca ggtgttcctg ctgggggggca gccgcaagcg   9180
tgtgctggtc gtgtggagc gggccacggt gtacagcgtg gagcaggaca atgatctgga    9240
gctggccgac gcctactacc tgggggggcgt gccgcccgac cagctgcccc cgagcctgcg   9300
acggctcttc cccaccggag gctcagtccg tggctgcgtc aaaggcatca aggccctggg    9360
caagtatgtg gacctcaagc ggctgaacac gacaggcgtg agcgccggct gcaccgccga    9420
cctgctggtg gggcgcgcca tgactttcca tggccacggc ttccttcgcc tggcgctctc    9480
gaacgtggca ccgctcactg gcaacgtcta ctccggcttc ggcttccaca cgcgcccagga   9540
cagtgccctg ctctactacc gggcgtcccc ggatgggcta tgccaggtgt ccctgcagca    9600
```

```
gggccgtgtg agcctacagc tcctgaggac tgaagtgaaa actcaagcgg gcttcgccga   9660
tggtgccccc cattacgtcg ccttctacag caatgccacg ggagtctggc tgtatgtcga   9720
tgaccagctc cagcagatga agccccaccg ggaccacccc ccgagctcc agccgcagcc    9780
tgaggggccc ccgaggctcc tcctgggagg cctgcctgag tctggcacca tttacaactt   9840
cagtggctgc atcagcaacg tcttcgtgca gcggctcctg ggcccacagc gcgtatttga   9900
tctgcagcag aacctgggca gcgtcaatgt gagcacgggc tgtgcacccg ccctgcaagc   9960
ccagaccccg ggcctggggc tagaggact gcaggccacc gcccggaagg cctcccgccg   10020
cagccgtcag cccgcccggc atcctgcctg catgctgccc ccacacctca ggaccacccg   10080
agactcctac cagtttgggg gttccctgtc cagtcacctg gagtttgtgg gcatcctggc   10140
ccgacatagg aactggccca gtctctccat gcacgtcctc ccgcgaagct cccgaggcct   10200
cctcctcttc actgcccgtc tgaggcccgg cagcccctcc ctggcgctct tcctgagcaa   10260
tggccacttc gttgcacaga tggaaggcct cgggactcgg ctccgcgccc agagccgcca   10320
gcgctcccgg cctggccgct ggcacaaggt ctccgtgcgc tgggagaaga accggatcct   10380
gctggtgacg gacggggccc gggcctggag ccaggagggg ccgcaccggc agcaccaggg   10440
ggcagagcac ccccagcccc acaccctctt tgtgggcggc ctcccggcca gcagccacag   10500
ctccaaactt ccggtgaccg tcgggttcag cggctgtgtg aagagactga ggctgcacgg   10560
gaggcccctg ggggccccca cacgatggc agggtcaca ccctgcatct ggccccct     10620
ggaggcgggc ctgttcttcc caggcagcgg gggagttatc actttagacc tcccaggagc   10680
tacactgcct gatgtgggcc tggaactgga ggtgcggccc ctggcagtca ccggactgat   10740
cttccacttg ggccaggccc ggacgccccc ctacttgcag ttgcaggtga ccgagaagca   10800
agtcctgctg cgggcggatg acggagcagg ggagttctcc acgtcagtga cccgccccct   10860
agtgctgtgt gatggccagt ggcaccggct agcggtgatg aaaagcggga atgtgctccg   10920
gctggaggtg gacgcgcaga gcaaccacac cgtgggcccc ttgctggcgg ctgcagctgg   10980
tgccccagcc cctctgtacc tcgggggcct gcctgagccc atggccgtgc agccctggcc   11040
ccccgcctac tgcggctgca tgaggaggct ggcggtgaac cggtccccg tcgccatgac    11100
tcgctctgtg gaggtccacg gggcagtggg ggccagtggc tgcccagccg cctaggacac   11160
agccaaccc ggcccctggt caggcccctg cagctgcctc acaccgcccc ttgtgctcgc    11220
ctcataggtg tctatttgga ctctaagctc tacgggtgac agatcttgtt tctgaagatg   11280
gtttaagtta tagcttctta aacgaaagaa taaaatactg caaaatgttt ttatatttgg   11340
cccttccacc cattttttaat tgtgagagat ttgtcaccaa tcatcactgg ttcctcctta   11400
aaaattaaaa agtaacttct gtgtaaccga aaaaaaaaa aaaaa                   11445
```

<210> SEQ ID NO 2
<211> LENGTH: 3695
<212> TYPE: PRT
<213> ORGANISM: Homo sapiens

<400> SEQUENCE: 2

```
Met Ala Lys Arg Leu Cys Ala Gly Ser Ala Leu Cys Val Arg Gly Pro
1               5                   10                  15

Arg Gly Pro Ala Pro Leu Leu Leu Val Gly Leu Ala Leu Leu Gly Ala
            20                  25                  30

Ala Arg Ala Arg Glu Glu Ala Gly Gly Gly Phe Ser Leu His Pro Pro
        35                  40                  45
```

```
Tyr Phe Asn Leu Ala Glu Gly Ala Arg Ile Ala Ala Ser Ala Thr Cys
     50                  55                  60

Gly Glu Glu Ala Pro Ala Arg Gly Ser Pro Arg Pro Thr Glu Asp Leu
 65                  70                  75                  80

Tyr Cys Lys Leu Val Gly Gly Pro Val Ala Gly Gly Asp Pro Asn Gln
                 85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
            115                 120                 125

Gln Ser Pro Pro Leu Ser Arg Gly Leu Glu Tyr Asn Glu Val Asn Val
            130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Phe Ala Ser Ser Lys
            180                 185                 190

Arg Asp Cys Leu Glu Arg Phe Gly Pro Gln Thr Leu Glu Arg Ile Thr
            195                 200                 205

Arg Asp Asp Ala Ala Ile Cys Thr Thr Glu Tyr Ser Arg Ile Val Pro
            210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
            275                 280                 285

Tyr Ser Ile Lys Asp Ile Ser Ile Gly Gly Arg Cys Val Cys His Gly
            290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
            325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
            355                 360                 365

Tyr Tyr Asp Pro Glu Val Asp Arg Arg Arg Ala Ser Gln Ser Leu Asp
            370                 375                 380

Gly Thr Tyr Gln Gly Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
            435                 440                 445

Cys Arg Pro Asn Phe Ser Gly Glu Arg Cys Asp Val Cys Ala Glu Gly
450                 455                 460

Phe Thr Gly Phe Pro Ser Cys Tyr Pro Thr Pro Ser Ser Ser Asn Asp
```

-continued

```
                465                 470                 475                 480
            Thr Arg Glu Gln Val Leu Pro Ala Gly Gln Ile Val Asn Cys Asp Cys
                            485                 490                 495

Ser Ala Ala Gly Thr Gln Gly Asn Ala Cys Arg Lys Asp Pro Arg Val
                            500                 505                 510

Gly Arg Cys Leu Cys Lys Pro Asn Phe Gln Gly Thr His Cys Glu Leu
                            515                 520                 525

Cys Ala Pro Gly Phe Tyr Gly Pro Gly Cys Gln Pro Cys Gln Cys Ser
                            530                 535                 540

Ser Pro Gly Val Ala Asp Asp Arg Cys Asp Pro Asp Thr Gly Gln Cys
            545                 550                 555                 560

Arg Cys Arg Val Gly Phe Glu Gly Ala Thr Cys Asp Arg Cys Ala Pro
                            565                 570                 575

Gly Tyr Phe His Phe Pro Leu Cys Gln Leu Cys Gly Cys Ser Pro Ala
                            580                 585                 590

Gly Thr Leu Pro Glu Gly Cys Asp Glu Ala Gly Arg Cys Leu Cys Gln
                            595                 600                 605

Pro Glu Phe Ala Gly Pro His Cys Asp Arg Cys Arg Pro Gly Tyr His
                            610                 615                 620

Gly Phe Pro Asn Cys Gln Ala Cys Thr Cys Asp Pro Arg Gly Ala Leu
            625                 630                 635                 640

Asp Gln Leu Cys Gly Ala Gly Gly Leu Cys Arg Cys Arg Pro Gly Tyr
                            645                 650                 655

Thr Gly Thr Ala Cys Gln Glu Cys Ser Pro Gly Phe His Gly Phe Pro
                            660                 665                 670

Ser Cys Val Pro Cys His Cys Ser Ala Glu Gly Ser Leu His Ala Ala
                            675                 680                 685

Cys Asp Pro Arg Ser Gly Gln Cys Ser Cys Arg Pro Arg Val Thr Gly
                            690                 695                 700

Leu Arg Cys Asp Thr Cys Val Pro Gly Ala Tyr Asn Phe Pro Tyr Cys
            705                 710                 715                 720

Glu Ala Gly Ser Cys His Pro Ala Gly Leu Ala Pro Val Asp Pro Ala
                            725                 730                 735

Leu Pro Glu Ala Gln Val Pro Cys Met Cys Arg Ala His Val Glu Gly
                            740                 745                 750

Pro Ser Cys Asp Arg Cys Lys Pro Gly Phe Trp Gly Leu Ser Pro Ser
                            755                 760                 765

Asn Pro Glu Gly Cys Thr Arg Cys Ser Cys Asp Leu Arg Gly Thr Leu
                            770                 775                 780

Gly Gly Val Ala Glu Cys Gln Pro Gly Thr Gly Gln Cys Phe Cys Lys
            785                 790                 795                 800

Pro His Val Cys Gly Gln Ala Cys Ala Ser Cys Lys Asp Gly Phe Phe
                            805                 810                 815

Gly Leu Asp Gln Ala Asp Tyr Phe Gly Cys Arg Ser Cys Arg Cys Asp
                            820                 825                 830

Ile Gly Gly Ala Leu Gly Gln Ser Cys Glu Pro Arg Thr Gly Val Cys
                            835                 840                 845

Arg Cys Arg Pro Asn Thr Gln Gly Pro Thr Cys Ser Glu Pro Ala Arg
                            850                 855                 860

Asp His Tyr Leu Pro Asp Leu His His Leu Arg Leu Glu Leu Glu Glu
            865                 870                 875                 880

Ala Ala Thr Pro Glu Gly His Ala Val Arg Phe Gly Phe Asn Pro Leu
                            885                 890                 895
```

-continued

```
Glu Phe Glu Asn Phe Ser Trp Arg Gly Tyr Ala Gln Met Ala Pro Val
            900                 905                 910
Gln Pro Arg Ile Val Ala Arg Leu Asn Leu Thr Ser Pro Asp Leu Phe
            915                 920                 925
Trp Leu Val Phe Arg Tyr Val Asn Arg Gly Ala Met Ser Val Ser Gly
            930                 935                 940
Arg Val Ser Val Arg Glu Glu Gly Arg Ser Ala Thr Cys Ala Asn Cys
945                 950                 955                 960
Thr Ala Gln Ser Gln Pro Val Ala Phe Pro Pro Ser Thr Glu Pro Ala
                965                 970                 975
Phe Ile Thr Val Pro Gln Arg Gly Phe Gly Pro Phe Val Leu Asn
            980                 985                 990
Pro Gly Thr Trp Ala Leu Arg Val  Glu Ala Glu Gly Val  Leu Leu Asp
            995                 1000                1005
Tyr Val  Val Leu Leu Pro Ser  Ala Tyr Tyr Glu Ala  Ala Leu Leu
    1010                1015                1020
Gln Leu Arg Val Thr Glu Ala  Cys Thr Tyr Arg Pro  Ser Ala Gln
    1025                1030                1035
Gln Ser  Gly Asp Asn Cys Leu  Leu Tyr Thr His Leu  Pro Leu Asp
    1040                1045                1050
Gly Phe  Pro Ser Ala Ala Gly  Leu Glu Ala Leu Cys  Arg Gln Asp
    1055                1060                1065
Asn Ser  Leu Pro Arg Pro Cys  Pro Thr Glu Gln Leu  Ser Pro Ser
    1070                1075                1080
His Pro  Pro Leu Ile Thr Cys  Thr Gly Ser Asp Val  Asp Val Gln
    1085                1090                1095
Leu Gln  Val Ala Val Pro Gln  Pro Gly Arg Tyr Ala  Leu Val Val
    1100                1105                1110
Glu Tyr  Ala Asn Glu Asp Ala  Arg Gln Glu Val Gly  Val Ala Val
    1115                1120                1125
His Thr  Pro Gln Arg Ala Pro  Gln Gln Gly Leu Leu  Ser Leu His
    1130                1135                1140
Pro Cys  Leu Tyr Ser Thr Leu  Cys Arg Gly Thr Ala  Arg Asp Thr
    1145                1150                1155
Gln Asp  His Leu Ala Val Phe  His Leu Asp Ser Glu  Ala Ser Val
    1160                1165                1170
Arg Leu  Thr Ala Glu Gln Ala  Arg Phe Phe Leu His  Gly Val Thr
    1175                1180                1185
Leu Val  Pro Ile Glu Glu Phe  Ser Pro Glu Phe Val  Glu Pro Arg
    1190                1195                1200
Val Ser  Cys Ile Ser Ser His  Gly Ala Phe Gly Pro  Asn Ser Ala
    1205                1210                1215
Ala Cys  Leu Pro Ser Arg Phe  Pro Lys Pro Pro Gln  Pro Ile Ile
    1220                1225                1230
Leu Arg  Asp Cys Gln Val Ile  Pro Leu Pro Pro Gly  Leu Pro Leu
    1235                1240                1245
Thr His  Ala Gln Asp Leu Thr  Pro Ala Met Ser Pro  Ala Gly Pro
    1250                1255                1260
Arg Pro  Arg Pro Pro Thr Ala  Val Asp Pro Asp Ala  Glu Pro Thr
    1265                1270                1275
Leu Leu  Arg Glu Pro Gln Ala  Thr Val Val Phe Thr  Thr His Val
    1280                1285                1290
```

```
Pro Thr Leu Gly Arg Tyr Ala Phe Leu Leu His Gly Tyr Gln Pro
    1295                1300                1305

Ala His Pro Thr Phe Pro Val Glu Val Leu Ile Asn Ala Gly Arg
    1310                1315                1320

Val Trp Gln Gly His Ala Asn Ala Ser Phe Cys Pro His Gly Tyr
    1325                1330                1335

Gly Cys Arg Thr Leu Val Val Cys Glu Gly Gln Ala Leu Leu Asp
    1340                1345                1350

Val Thr His Ser Glu Leu Thr Val Thr Val Arg Val Pro Lys Gly
    1355                1360                1365

Arg Trp Leu Trp Leu Asp Tyr Val Leu Val Val Pro Glu Asn Val
    1370                1375                1380

Tyr Ser Phe Gly Tyr Leu Arg Glu Glu Pro Leu Asp Lys Ser Tyr
    1385                1390                1395

Asp Phe Ile Ser His Cys Ala Ala Gln Gly Tyr His Ile Ser Pro
    1400                1405                1410

Ser Ser Ser Ser Leu Phe Cys Arg Asn Ala Ala Ala Ser Leu Ser
    1415                1420                1425

Leu Phe Tyr Asn Asn Gly Ala Arg Pro Cys Gly Cys His Glu Val
    1430                1435                1440

Gly Ala Thr Gly Pro Thr Cys Glu Pro Phe Gly Gly Gln Cys Pro
    1445                1450                1455

Cys His Ala His Val Ile Gly Arg Asp Cys Ser Arg Cys Ala Thr
    1460                1465                1470

Gly Tyr Trp Gly Phe Pro Asn Cys Arg Pro Cys Asp Cys Gly Ala
    1475                1480                1485

Arg Leu Cys Asp Glu Leu Thr Gly Gln Cys Ile Cys Pro Pro Arg
    1490                1495                1500

Thr Ile Pro Pro Asp Cys Leu Leu Cys Gln Pro Gln Thr Phe Gly
    1505                1510                1515

Cys His Pro Leu Val Gly Cys Glu Glu Cys Asn Cys Ser Gly Pro
    1520                1525                1530

Gly Ile Gln Glu Leu Thr Asp Pro Thr Cys Asp Thr Asp Ser Gly
    1535                1540                1545

Gln Cys Lys Cys Arg Pro Asn Val Thr Gly Arg Arg Cys Asp Thr
    1550                1555                1560

Cys Ser Pro Gly Phe His Gly Tyr Pro Arg Cys Arg Pro Cys Asp
    1565                1570                1575

Cys His Glu Ala Gly Thr Ala Pro Gly Val Cys Asp Pro Leu Thr
    1580                1585                1590

Gly Gln Cys Tyr Cys Lys Glu Asn Val Gln Gly Pro Lys Cys Asp
    1595                1600                1605

Gln Cys Ser Leu Gly Thr Phe Ser Leu Asp Ala Ala Asn Pro Lys
    1610                1615                1620

Gly Cys Thr Arg Cys Phe Cys Phe Gly Ala Thr Glu Arg Cys Arg
    1625                1630                1635

Ser Ser Ser Tyr Thr Arg Gln Glu Phe Val Asp Met Glu Gly Trp
    1640                1645                1650

Val Leu Leu Ser Thr Asp Arg Gln Val Val Pro His Glu Arg Gln
    1655                1660                1665

Pro Gly Thr Glu Met Leu Arg Ala Asp Leu Arg His Val Pro Glu
    1670                1675                1680

Ala Val Pro Glu Ala Phe Pro Glu Leu Tyr Trp Gln Ala Pro Pro
```

-continued

```
            1685                1690                1695
Ser Tyr Leu Gly Asp Arg Val Ser Ser Tyr Gly Gly Thr Leu Arg
    1700                1705                1710
Tyr Glu Leu His Ser Glu Thr Gln Arg Gly Asp Val Phe Val Pro
    1715                1720                1725
Met Glu Ser Arg Pro Asp Val Val Leu Gln Gly Asn Gln Met Ser
    1730                1735                1740
Ile Thr Phe Leu Glu Pro Ala Tyr Pro Thr Pro Gly His Val His
    1745                1750                1755
Arg Gly Gln Leu Gln Leu Val Glu Gly Asn Phe Arg His Thr Glu
    1760                1765                1770
Thr Arg Asn Thr Val Ser Arg Glu Glu Leu Met Met Val Leu Ala
    1775                1780                1785
Ser Leu Glu Gln Leu Gln Ile Arg Ala Leu Phe Ser Gln Ile Ser
    1790                1795                1800
Ser Ala Val Phe Leu Arg Arg Val Ala Leu Glu Val Ala Ser Pro
    1805                1810                1815
Ala Gly Gln Gly Ala Leu Ala Ser Asn Val Glu Leu Cys Leu Cys
    1820                1825                1830
Pro Ala Ser Tyr Arg Gly Asp Ser Cys Gln Glu Cys Ala Pro Gly
    1835                1840                1845
Phe Tyr Arg Asp Val Lys Gly Leu Phe Leu Gly Arg Cys Val Pro
    1850                1855                1860
Cys Gln Cys His Gly His Ser Asp Arg Cys Leu Pro Gly Ser Gly
    1865                1870                1875
Val Cys Val Asp Cys Gln His Asn Thr Glu Gly Ala His Cys Glu
    1880                1885                1890
Arg Cys Gln Ala Gly Phe Val Ser Ser Arg Asp Asp Pro Ser Ala
    1895                1900                1905
Pro Cys Val Ser Cys Pro Cys Pro Leu Ser Val Pro Ser Asn Asn
    1910                1915                1920
Phe Ala Glu Gly Cys Val Leu Arg Gly Gly Arg Thr Gln Cys Leu
    1925                1930                1935
Cys Lys Pro Gly Tyr Ala Gly Ala Ser Cys Glu Arg Cys Ala Pro
    1940                1945                1950
Gly Phe Phe Gly Asn Pro Leu Val Leu Gly Ser Ser Cys Gln Pro
    1955                1960                1965
Cys Asp Cys Ser Gly Asn Gly Asp Pro Asn Leu Leu Phe Ser Asp
    1970                1975                1980
Cys Asp Pro Leu Thr Gly Ala Cys Arg Gly Cys Leu Arg His Thr
    1985                1990                1995
Thr Gly Pro Arg Cys Glu Ile Cys Ala Pro Gly Phe Tyr Gly Asn
    2000                2005                2010
Ala Leu Leu Pro Gly Asn Cys Thr Arg Cys Asp Cys Thr Pro Cys
    2015                2020                2025
Gly Thr Glu Ala Cys Asp Pro His Ser Gly His Cys Leu Cys Lys
    2030                2035                2040
Ala Gly Val Thr Gly Arg Arg Cys Asp Arg Cys Gln Glu Gly His
    2045                2050                2055
Phe Gly Phe Asp Gly Cys Gly Gly Cys Arg Pro Cys Ala Cys Gly
    2060                2065                2070
Pro Ala Ala Glu Gly Ser Glu Cys His Pro Gln Ser Gly Gln Cys
    2075                2080                2085
```

```
His Cys Arg Pro Gly Thr Met Gly Pro Gln Cys Arg Glu Cys Ala
2090                2095                2100

Pro Gly Tyr Trp Gly Leu Pro Glu Gln Gly Cys Arg Arg Cys Gln
2105                2110                2115

Cys Pro Gly Gly Arg Cys Asp Pro His Thr Gly Arg Cys Asn Cys
2120                2125                2130

Pro Pro Gly Leu Ser Gly Glu Arg Cys Asp Thr Cys Ser Gln Gln
2135                2140                2145

His Gln Val Pro Val Pro Gly Gly Pro Val Gly His Ser Ile His
2150                2155                2160

Cys Glu Val Cys Asp His Cys Val Val Leu Leu Leu Asp Asp Leu
2165                2170                2175

Glu Arg Ala Gly Ala Leu Leu Pro Ala Ile His Glu Gln Leu Arg
2180                2185                2190

Gly Ile Asn Ala Ser Ser Met Ala Trp Ala Arg Leu His Arg Leu
2195                2200                2205

Asn Ala Ser Ile Ala Asp Leu Gln Ser Gln Leu Arg Ser Pro Leu
2210                2215                2220

Gly Pro Arg His Glu Thr Ala Gln Gln Leu Glu Val Leu Glu Gln
2225                2230                2235

Gln Ser Thr Ser Leu Gly Gln Asp Ala Arg Arg Leu Gly Gly Gln
2240                2245                2250

Ala Val Gly Thr Arg Asp Gln Ala Ser Gln Leu Leu Ala Gly Thr
2255                2260                2265

Glu Ala Thr Leu Gly His Ala Lys Thr Leu Leu Ala Ala Ile Arg
2270                2275                2280

Ala Val Asp Arg Thr Leu Ser Glu Leu Met Ser Gln Thr Gly His
2285                2290                2295

Leu Gly Leu Ala Asn Ala Ser Ala Pro Ser Gly Glu Gln Leu Leu
2300                2305                2310

Arg Thr Leu Ala Glu Val Glu Arg Leu Leu Trp Glu Met Arg Ala
2315                2320                2325

Arg Asp Leu Gly Ala Pro Gln Ala Ala Ala Glu Ala Glu Leu Ala
2330                2335                2340

Ala Ala Gln Arg Leu Leu Ala Arg Val Gln Glu Gln Leu Ser Ser
2345                2350                2355

Leu Trp Glu Glu Asn Gln Ala Leu Ala Thr Gln Thr Arg Asp Arg
2360                2365                2370

Leu Ala Gln His Glu Ala Gly Leu Met Asp Leu Arg Glu Ala Leu
2375                2380                2385

Asn Arg Ala Val Asp Ala Thr Arg Glu Ala Gln Glu Leu Asn Ser
2390                2395                2400

Arg Asn Gln Glu Arg Leu Glu Glu Ala Leu Gln Arg Lys Gln Glu
2405                2410                2415

Leu Ser Arg Asp Asn Ala Thr Leu Gln Ala Thr Leu His Ala Ala
2420                2425                2430

Arg Asp Thr Leu Ala Ser Val Phe Arg Leu Leu His Ser Leu Asp
2435                2440                2445

Gln Ala Lys Glu Glu Leu Glu Arg Leu Ala Ala Ser Leu Asp Gly
2450                2455                2460

Ala Arg Thr Pro Leu Leu Gln Arg Met Gln Thr Phe Ser Pro Ala
2465                2470                2475
```

```
Gly Ser Lys Leu Arg Leu Val Glu Ala Ala Glu Ala His Ala Gln
    2480                2485                2490

Gln Leu Gly Gln Leu Ala Leu Asn Leu Ser Ser Ile Ile Leu Asp
    2495                2500                2505

Val Asn Gln Asp Arg Leu Thr Gln Arg Ala Ile Glu Ala Ser Asn
    2510                2515                2520

Ala Tyr Ser Arg Ile Leu Gln Ala Val Gln Ala Ala Glu Asp Ala
    2525                2530                2535

Ala Gly Gln Ala Leu Gln Gln Ala Asp His Thr Trp Ala Thr Val
    2540                2545                2550

Val Arg Gln Gly Leu Val Asp Arg Ala Gln Gln Leu Leu Ala Asn
    2555                2560                2565

Ser Thr Ala Leu Glu Glu Ala Met Leu Gln Glu Gln Gln Arg Leu
    2570                2575                2580

Gly Leu Val Trp Ala Ala Leu Gln Gly Ala Arg Thr Gln Leu Arg
    2585                2590                2595

Asp Val Arg Ala Lys Lys Asp Gln Leu Glu Ala His Ile Gln Ala
    2600                2605                2610

Ala Gln Ala Met Leu Ala Met Asp Thr Asp Glu Thr Ser Lys Lys
    2615                2620                2625

Ile Ala His Ala Lys Ala Val Ala Ala Glu Ala Gln Asp Thr Ala
    2630                2635                2640

Thr Arg Val Gln Ser Gln Leu Gln Ala Met Gln Glu Asn Val Glu
    2645                2650                2655

Arg Trp Gln Gly Gln Tyr Glu Gly Leu Arg Gly Gln Asp Leu Gly
    2660                2665                2670

Gln Ala Val Leu Asp Ala Gly His Ser Val Ser Thr Leu Glu Lys
    2675                2680                2685

Thr Leu Pro Gln Leu Leu Ala Lys Leu Ser Ile Leu Glu Asn Arg
    2690                2695                2700

Gly Val His Asn Ala Ser Leu Ala Leu Ser Ala Ser Ile Gly Arg
    2705                2710                2715

Val Arg Glu Leu Ile Ala Gln Ala Arg Gly Ala Ala Ser Lys Val
    2720                2725                2730

Lys Val Pro Met Lys Phe Asn Gly Arg Ser Gly Val Gln Leu Arg
    2735                2740                2745

Thr Pro Arg Asp Leu Ala Asp Leu Ala Ala Tyr Thr Ala Leu Lys
    2750                2755                2760

Phe Tyr Leu Gln Gly Pro Glu Pro Glu Pro Gly Gln Gly Thr Glu
    2765                2770                2775

Asp Arg Phe Val Met Tyr Met Gly Ser Arg Gln Ala Thr Gly Asp
    2780                2785                2790

Tyr Met Gly Val Ser Leu Arg Asp Lys Lys Val His Trp Val Tyr
    2795                2800                2805

Gln Leu Gly Glu Ala Gly Pro Ala Val Leu Ser Ile Asp Glu Asp
    2810                2815                2820

Ile Gly Glu Gln Phe Ala Ala Val Ser Leu Asp Arg Thr Leu Gln
    2825                2830                2835

Phe Gly His Met Ser Val Thr Val Glu Arg Gln Met Ile Gln Glu
    2840                2845                2850

Thr Lys Gly Asp Thr Val Ala Pro Gly Ala Glu Gly Leu Leu Asn
    2855                2860                2865

Leu Arg Pro Asp Asp Phe Val Phe Tyr Val Gly Gly Tyr Pro Ser
```

-continued

```
                  2870                2875                2880

Thr Phe Thr Pro Pro Leu Leu Arg Phe Pro Gly Tyr Arg Gly
        2885                2890                2895

Cys Ile Glu Met Asp Thr Leu Asn Glu Val Val Ser Leu Tyr
        2900                2905                2910

Asn Phe Glu Arg Thr Phe Gln Leu Asp Thr Ala Val Asp Arg Pro
        2915                2920                2925

Cys Ala Arg Ser Lys Ser Thr Gly Asp Pro Trp Leu Thr Asp Gly
        2930                2935                2940

Ser Tyr Leu Asp Gly Thr Gly Phe Ala Arg Ile Ser Phe Asp Ser
        2945                2950                2955

Gln Ile Ser Thr Thr Lys Arg Phe Glu Gln Glu Leu Arg Leu Val
        2960                2965                2970

Ser Tyr Ser Gly Val Leu Phe Phe Leu Lys Gln Gln Ser Gln Phe
        2975                2980                2985

Leu Cys Leu Ala Val Gln Glu Gly Ser Leu Val Leu Leu Tyr Asp
        2990                2995                3000

Phe Gly Ala Gly Leu Lys Lys Ala Val Pro Leu Gln Pro Pro Pro
        3005                3010                3015

Pro Leu Thr Ser Ala Ser Lys Ala Ile Gln Val Phe Leu Leu Gly
        3020                3025                3030

Gly Ser Arg Lys Arg Val Leu Val Arg Val Glu Arg Ala Thr Val
        3035                3040                3045

Tyr Ser Val Glu Gln Asp Asn Asp Leu Glu Leu Ala Asp Ala Tyr
        3050                3055                3060

Tyr Leu Gly Gly Val Pro Pro Asp Gln Leu Pro Pro Ser Leu Arg
        3065                3070                3075

Arg Leu Phe Pro Thr Gly Gly Ser Val Arg Gly Cys Val Lys Gly
        3080                3085                3090

Ile Lys Ala Leu Gly Lys Tyr Val Asp Leu Lys Arg Leu Asn Thr
        3095                3100                3105

Thr Gly Val Ser Ala Gly Cys Thr Ala Asp Leu Leu Val Gly Arg
        3110                3115                3120

Ala Met Thr Phe His Gly His Gly Phe Leu Arg Leu Ala Leu Ser
        3125                3130                3135

Asn Val Ala Pro Leu Thr Gly Asn Val Tyr Ser Gly Phe Gly Phe
        3140                3145                3150

His Ser Ala Gln Asp Ser Ala Leu Leu Tyr Tyr Arg Ala Ser Pro
        3155                3160                3165

Asp Gly Leu Cys Gln Val Ser Leu Gln Gln Gly Arg Val Ser Leu
        3170                3175                3180

Gln Leu Leu Arg Thr Glu Val Lys Thr Gln Ala Gly Phe Ala Asp
        3185                3190                3195

Gly Ala Pro His Tyr Val Ala Phe Tyr Ser Asn Ala Thr Gly Val
        3200                3205                3210

Trp Leu Tyr Val Asp Asp Gln Leu Gln Gln Met Lys Pro His Arg
        3215                3220                3225

Gly Pro Pro Pro Glu Leu Gln Pro Gln Pro Glu Gly Pro Pro Arg
        3230                3235                3240

Leu Leu Leu Gly Gly Leu Pro Glu Ser Gly Thr Ile Tyr Asn Phe
        3245                3250                3255

Ser Gly Cys Ile Ser Asn Val Phe Val Gln Arg Leu Leu Gly Pro
        3260                3265                3270
```

```
Gln Arg Val Phe Asp Leu Gln Gln Asn Leu Gly Ser Val Asn Val
    3275                3280                3285

Ser Thr Gly Cys Ala Pro Ala Leu Gln Ala Gln Thr Pro Gly Leu
    3290                3295                3300

Gly Pro Arg Gly Leu Gln Ala Thr Ala Arg Lys Ala Ser Arg Arg
    3305                3310                3315

Ser Arg Gln Pro Ala Arg His Pro Ala Cys Met Leu Pro Pro His
    3320                3325                3330

Leu Arg Thr Thr Arg Asp Ser Tyr Gln Phe Gly Gly Ser Leu Ser
    3335                3340                3345

Ser His Leu Glu Phe Val Gly Ile Leu Ala Arg His Arg Asn Trp
    3350                3355                3360

Pro Ser Leu Ser Met His Val Leu Pro Arg Ser Ser Arg Gly Leu
    3365                3370                3375

Leu Leu Phe Thr Ala Arg Leu Arg Pro Gly Ser Pro Ser Leu Ala
    3380                3385                3390

Leu Phe Leu Ser Asn Gly His Phe Val Ala Gln Met Glu Gly Leu
    3395                3400                3405

Gly Thr Arg Leu Arg Ala Gln Ser Arg Gln Arg Ser Arg Pro Gly
    3410                3415                3420

Arg Trp His Lys Val Ser Val Arg Trp Glu Lys Asn Arg Ile Leu
    3425                3430                3435

Leu Val Thr Asp Gly Ala Arg Ala Trp Ser Gln Glu Gly Pro His
    3440                3445                3450

Arg Gln His Gln Gly Ala Glu His Pro Gln Pro His Thr Leu Phe
    3455                3460                3465

Val Gly Gly Leu Pro Ala Ser Ser His Ser Ser Lys Leu Pro Val
    3470                3475                3480

Thr Val Gly Phe Ser Gly Cys Val Lys Arg Leu Arg Leu His Gly
    3485                3490                3495

Arg Pro Leu Gly Ala Pro Thr Arg Met Ala Gly Val Thr Pro Cys
    3500                3505                3510

Ile Leu Gly Pro Leu Glu Ala Gly Leu Phe Phe Pro Gly Ser Gly
    3515                3520                3525

Gly Val Ile Thr Leu Asp Leu Pro Gly Ala Thr Leu Pro Asp Val
    3530                3535                3540

Gly Leu Glu Leu Glu Val Arg Pro Leu Ala Val Thr Gly Leu Ile
    3545                3550                3555

Phe His Leu Gly Gln Ala Arg Thr Pro Pro Tyr Leu Gln Leu Gln
    3560                3565                3570

Val Thr Glu Lys Gln Val Leu Leu Arg Ala Asp Asp Gly Ala Gly
    3575                3580                3585

Glu Phe Ser Thr Ser Val Thr Arg Pro Ser Val Leu Cys Asp Gly
    3590                3595                3600

Gln Trp His Arg Leu Ala Val Met Lys Ser Gly Asn Val Leu Arg
    3605                3610                3615

Leu Glu Val Asp Ala Gln Ser Asn His Thr Val Gly Pro Leu Leu
    3620                3625                3630

Ala Ala Ala Ala Gly Ala Pro Ala Pro Leu Tyr Leu Gly Gly Leu
    3635                3640                3645

Pro Glu Pro Met Ala Val Gln Pro Trp Pro Pro Ala Tyr Cys Gly
    3650                3655                3660
```

| Cys | Met | Arg | Arg | Leu | Ala | Val | Asn | Arg | Ser | Pro | Val | Ala | Met | Thr |
| | 3665 | | | | 3670 | | | | | 3675 | | | | |

| Arg | Ser | Val | Glu | Val | His | Gly | Ala | Val | Gly | Ala | Ser | Gly | Cys | Pro |
| 3680 | | | | | 3685 | | | | | 3690 | | | | |

Ala Ala
    3695

<210> SEQ ID NO 3
<211> LENGTH: 5866
<212> TYPE: DNA
<213> ORGANISM: Homo sapiens

<400> SEQUENCE: 3

```
gggacctgga agcgcccag ccccgcagcg atcgcagatt cggctttcaa acaaaagagg      60
cgccccgggg ggtgggaccg ggacctcacc cggtcctcgc agagttgcgg ccgcccgccc     120
cttcagcccc ggctctccgt atgcgcatga gcagaggcgc ctccctctgt tcctcccaag     180
gctaaacttt ctaattccct tctttgggct cggggctcc cggagcaggg cgagagctcg      240
cgtcgccgga aaggaagacg ggaagaaagg gcaggcggct cggcgggcgt cttctccact     300
cctctgccgc gtccccgtgg ctgcaggag ccggcatggg gcttctccag ttgctagctt      360
tcagtttctt agccctgtgc agagcccgag tgcgcgctca ggaacccgag ttcagctacg     420
gctgcgcaga aggcagctgc tatcccgcca cgggcgacct tctcatcggc cgagcacaga     480
agctttcggt gacctcgacg tgcgggctgc acaagcccga accctactgt atcgtcagcc     540
acttgcagga ggacaaaaaa tgcttcatat gcaattccca agatcctat catgagaccc       600
tgaatcctga cagccatctc attgaaaatg tggtcactac atttgctcca aaccgcctta     660
agatttggtg gcaatctgaa aatggtgtgg aaaatgtaac tatccaactg gatttggaag     720
cagaattcca ttttactcat ctcataatga cttcaagac attccgtcca gctgctatgc      780
tgatagaacg atcgtccgac tttgggaaaa cctggggtgt gtatagatac ttcgcctatg     840
actgtgaggc ctcgttccca ggcatttcaa ctggcccat gaaaaaagtc gatgacataa       900
tttgtgattc tcgatattct gacattgaac cctcaactga aggagaggtg atatttcgtg     960
ctttagatcc tgctttcaaa atagaagatc cttatagccc aaggatacag aatttattaa     1020
aaattaccaa cttgagaatc aagttttgtg aactgcatac tttgggagat aaccttctgg     1080
attccaggat ggaaatcaga gaaaagtatt attatgcagt ttatgatatg gtggttcgag     1140
gaaattgctt ctgctatggt catgccagcg aatgtgcccc tgtggatgga ttcaatgaag     1200
aagtggaagg aatggttcac ggacactgca tgtgcaggca taacaccaag ggcttaaact     1260
gtgaactctg catggatttc taccatgatt taccttggag acctgctgaa ggccgaaaca     1320
gcaacgcctg taaaaaatgt aactgcaatg aacattccat ctcttgtcac tttgacatgg     1380
ctgtttacct ggccacgggg aacgtcagcg gaggcgtgtg tgatgactgt cagcacaaca     1440
ccatggggcg caactgtgag cagtgcaagc cgttttacta ccagcaccca gagagggaca     1500
tccgagatcc taatttctgt gaacgatgta cgtgtgaccc agctggctct caaaatgagg     1560
gaatttgtga cagctatact gattttttcta ctggtctcat tgctggccag tgtcggtgta     1620
aattaaatgt ggaaggagaa cattgtgatg tttgcaaaga aggcttctat gatttaagca     1680
gtgaagatcc atttggttgt aaatcttgtg cttgcaatcc tctgggaaca attcctggag     1740
ggaatccttg tgattccgag acaggtcact gctactgcaa gcgtctggtg acaggacagc     1800
attgtgacca gtgcctgcca gagcactggg gcttaagcaa tgatttggat ggatgtcgac     1860
```

```
catgtgactg tgaccttggg ggagccttaa acaacagttg ctttgcggag tcaggccagt    1920
gctcatgccg gcctcacatg attggacgtc agtgcaacga agtggaacct ggttactact    1980
ttgccaccct ggatcactac ctctatgaag cggaggaagc caacttgggg cctggggtta    2040
gcatagtgga gcggcaatat atccaggacc ggattccctc ctggactgga gccggcttcg    2100
tccgagtgcc tgaaggggct tatttggagt ttttcattga acatacca tattccatgg     2160 agtacgacat cctaattcgc tacgagccac agctacccga ccactgggaa aaagctgtca    2220
tcacagtgca gcgacctgga aggattccaa ccagcagccg atgtggtaat accatccccg    2280
atgatgacaa ccaggtggtg tcattatcac caggctcaag atatgtcgtc cttcctcggc    2340
cggtgtgctt tgagaaggga acaaactaca cggtgaggtt ggagctgcct cagtacacct    2400
cctctgatag cgacgtggag agccctaca cgctgatcga ttctcttgtt ctcatgccat     2460
actgtaaatc actggacatc ttcaccgtgg gaggttcagg agatggggtg gtcaccaaca    2520
gtgcctggga aacctttcag agataccgat gtctagagaa cagcagaagc gttgtgaaaa    2580
caccgatgac agatgtttgc agaaacatca tctttagcat ttctgccctg ttacaccaga    2640
caggcctggc ttgtgaatgc gaccctcagg gttcgttaag ttccgtgtgt gatcccaacg    2700
gaggccagtg ccagtgccgg cccaacgtgg ttggaagaac ctgcaacaga tgtgcacctg    2760
gaactttggg ctttggcccc agtggatgca aaccttgtga gtgccatctg caaggatctg    2820
tcaatgcctt ctgcaatccc gtcactggcc agtgccactg tttccaggga gtgtatgctc    2880
ggcagtgtga tcggtgctta cctgggcact ggggctttcc aagttgccag ccctgccagt    2940
gcaatggcca cgccgatgac tgcgacccag tgactgggga gtgcttgaac tgccaggact    3000
acaccatggg tcataactgt gaaaggtgct tggctggtta ctatggcgac cccatcattg    3060
ggtcaggaga tcactgccgc ccttgccctt gcccagatgg tcccgacagt ggacgccagt    3120
ttgccaggag ctgctaccaa gatcctgtta ctttacagct tgcctgtgtt tgtgatcctg    3180
gatacattgg ttccagatgt gacgactgtg cctcaggata cttttggcaat ccatcagaag    3240 ttgggggtc gtgtcagcct tgccagtgtc acaacaacat tgacacgaca gacccagaag    3300
cctgtgacaa ggagactggg aggtgtctca agtgcctgta ccacacggaa ggggaacact    3360
gtcagttctg ccggtttgga tactatggtg atgccctcca gcaggactgt cgaaagtgtg    3420
tctgtaatta cctgggcacc gtgcaagagc actgtaacgg ctctgactgc cagtgcgaca    3480
aagccactgg tcagtgcttg tgtcttccta atgtgatcgg gcagaactgt gaccgctgtg    3540
cgcccaatac ctggcagctg gccagtggca ctggctgtga cccatgcaac tgcaatgctg    3600
ctcattcctt cgggccatct tgcaatgagt tcacggggca gtgccagtgc atgcctgggt    3660
ttggaggccg cacctgcagc gagtgccagg aactcttctg gggagacccc gacgtggagt    3720
gccgagcctg tgactgtgac cccaggggca ttgagacgcc acagtgtgac cagtccacgg    3780
gccagtgtgt ctgcgttgag ggtgttgagg gtccacgctg tgacaagtgc acgcgagggt    3840
actcgggggt cttccctgac tgcacaccct gccaccagtg ctttgctctc tgggatgtga    3900
tcattgccga gctgaccaac aggacacaca gattcctgga aaagccaag gccttgaaga     3960 tcagtggtgt gatcggcct taccgtgaga ctgtggactc ggtggagagg aaagtcagcg     4020
agataaaaga catcctggcg cagagccccg cagcagagcc actgaaaaac attgggaatc    4080
tctttgagga agcagagaaa ctgattaaag atgttacaga aatgatggct caagtagaag    4140
tgaaattatc tgcacacaact tcccaaagca acagcacagc caaagaactg gattctctac    4200
agacagaagc cgaaagccta gacaacactg tgaaagaact tgctgaacaa ctggaattta    4260
```

-continued

```
tcaaaaactc agatattcgg ggtgccttgg atagcattac caagtatttc cagatgtctc    4320
ttgaggcaga ggagagggtg aatgcctcca ccacagaacc caacagcact gtggagcagt    4380
cagccctcat gagagacaga gtagaagacg tgatgatgga gcgagaatcc cagttcaagg    4440
aaaaacaaga ggagcaggct cgcctccttg atgaactggc aggcaagcta caaagcctag    4500
acctttcagc cgctgccgaa atgacctgtg aacacccccc aggggcctcc tgttccgaga    4560
ctgaatgtgg cgggccaaac tgcagaactg acgaaggaga gaggaagtgt gggggggcctg   4620 gctgtggtgg tctggttact gttgcacaca acgcctggca gaaagccatg gacttggacc    4680
aagatgtcct gagtgccctg gctgaagtgg aacagctctc caagatggtc tctgaagcaa    4740
aactgagggc agatgaggca aaacaaagtg ctgaagacat tctgttgaag acaaatgcta    4800
ccaaagaaaa aatggacaag agcaatgagg agctgagaaa tctaatcaag caaatcagaa    4860 acttttttgac ccaggatagt gctgatttgg acagcattga agcagttgct aatgaagtat    4920
tgaaaatgga gatgcctagc accccacagc agttacagaa cttgacagaa gatatacgtg    4980
aacgagttga aagcctttct caagtagagg ttattcttca gcatagtgct gctgacattg    5040
ccagagctga gatgttgtta gaagaagcta aagagcaag caaagtgca acagatgtta    5100 aagtcactgc agatatggta aaggaagctc tggaagaagc agaaaaggcc caggtcgcag    5160
cagagaaggc aattaaacaa gcagatgaag acattcaagg aacccagaac ctgttaactt    5220
cgattgagtc tgaaacagca gcttctgagg aaaccttgtt caacgcgtcc cagcgcatca    5280
gcgagttaga gaggaatgtg gaagaactta agcggaaagc tgcccaaaac tccggggagg    5340
cagaatatat tgaaaaagta gtatatactg tgaagcaaag tgcagaagat gttaagaaga    5400
ctttagatgg tgaacttgat gaaaagtata aaaaagtaga aaatttaatt gccaaaaaaa    5460
ctgaagagtc agctgatgcc agaaggaaag ccgaaatgct acaaaatgaa gcaaaaactc    5520
ttttagctca agcaaatagc aagctgcaac tgctcaaaga tttagaaaga aaatatgaag    5580
acaatcaaag atacttagaa gataaagctc aagaattagc aagactggaa ggagaagtcc    5640
gttcactcct aaaggatata agccagaaag ttgctgtgta tagcacatgc ttgtaacaga    5700
ggagaataaa aaatggctga ggtgaacaag gtaaaacaac tacattttaa aaactgactt    5760
aatgctcttc aaaataaaac atcacctatt taatgttttt aatcacattt tgtatggagt    5820
taaataaagt acagtgcttt tgtataaaaa aaaaaaaaa aaaaa                     5866
```

<210> SEQ ID NO 4
<211> LENGTH: 1786
<212> TYPE: PRT
<213> ORGANISM: Homo sapiens

<400> SEQUENCE: 4

```
Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
    50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
```

```
                        85                      90                      95
Glu Asn Val Val Thr Thr Phe Ala Pro Asn Arg Leu Lys Ile Trp Trp
                100                     105                     110

Gln Ser Glu Asn Gly Val Glu Asn Val Thr Ile Gln Leu Asp Leu Glu
            115                     120                     125

Ala Glu Phe His Phe Thr His Leu Ile Met Thr Phe Lys Thr Phe Arg
        130                     135                     140

Pro Ala Ala Met Leu Ile Glu Arg Ser Ser Asp Phe Gly Lys Thr Trp
145                     150                     155                     160

Gly Val Tyr Arg Tyr Phe Ala Tyr Asp Cys Glu Ala Ser Phe Pro Gly
                165                     170                     175

Ile Ser Thr Gly Pro Met Lys Lys Val Asp Asp Ile Ile Cys Asp Ser
                180                     185                     190

Arg Tyr Ser Asp Ile Glu Pro Ser Thr Glu Gly Glu Val Ile Phe Arg
            195                     200                     205

Ala Leu Asp Pro Ala Phe Lys Ile Glu Asp Pro Tyr Ser Pro Arg Ile
        210                     215                     220

Gln Asn Leu Leu Lys Ile Thr Asn Leu Arg Ile Lys Phe Val Lys Leu
225                     230                     235                     240

His Thr Leu Gly Asp Asn Leu Leu Asp Ser Arg Met Glu Ile Arg Glu
                245                     250                     255

Lys Tyr Tyr Tyr Ala Val Tyr Asp Met Val Val Arg Gly Asn Cys Phe
                260                     265                     270

Cys Tyr Gly His Ala Ser Glu Cys Ala Pro Val Asp Gly Phe Asn Glu
            275                     280                     285

Glu Val Glu Gly Met Val His Gly His Cys Met Cys Arg His Asn Thr
        290                     295                     300

Lys Gly Leu Asn Cys Glu Leu Cys Met Asp Phe Tyr His Asp Leu Pro
305                     310                     315                     320

Trp Arg Pro Ala Glu Gly Arg Asn Ser Asn Ala Cys Lys Lys Cys Asn
                325                     330                     335

Cys Asn Glu His Ser Ile Ser Cys His Phe Asp Met Ala Val Tyr Leu
                340                     345                     350

Ala Thr Gly Asn Val Ser Gly Gly Val Cys Asp Asp Cys Gln His Asn
            355                     360                     365

Thr Met Gly Arg Asn Cys Glu Gln Cys Lys Pro Phe Tyr Tyr Gln His
        370                     375                     380

Pro Glu Arg Asp Ile Arg Asp Pro Asn Phe Cys Glu Arg Cys Thr Cys
385                     390                     395                     400

Asp Pro Ala Gly Ser Gln Asn Glu Gly Ile Cys Asp Ser Tyr Thr Asp
                405                     410                     415

Phe Ser Thr Gly Leu Ile Ala Gly Gln Cys Arg Cys Lys Leu Asn Val
                420                     425                     430

Glu Gly Glu His Cys Asp Val Cys Lys Glu Gly Phe Tyr Asp Leu Ser
            435                     440                     445

Ser Glu Asp Pro Phe Gly Cys Lys Ser Cys Ala Cys Asn Pro Leu Gly
        450                     455                     460

Thr Ile Pro Gly Gly Asn Pro Cys Asp Ser Glu Thr Gly His Cys Tyr
465                     470                     475                     480

Cys Lys Arg Leu Val Thr Gly Gln His Cys Asp Gln Cys Leu Pro Glu
                485                     490                     495

His Trp Gly Leu Ser Asn Asp Leu Asp Gly Cys Arg Pro Cys Asp Cys
                500                     505                     510
```

```
Asp Leu Gly Gly Ala Leu Asn Asn Ser Cys Phe Ala Glu Ser Gly Gln
            515                 520                 525

Cys Ser Cys Arg Pro His Met Ile Gly Arg Gln Cys Asn Glu Val Glu
        530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
            580                 585                 590

Glu Gly Ala Tyr Leu Glu Phe Phe Ile Asp Asn Ile Pro Tyr Ser Met
        595                 600                 605

Glu Tyr Asp Ile Leu Ile Arg Tyr Glu Pro Gln Leu Pro Asp His Trp
    610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
            660                 665                 670

Glu Lys Gly Thr Asn Tyr Thr Val Arg Leu Glu Leu Pro Gln Tyr Thr
        675                 680                 685

Ser Ser Asp Ser Asp Val Glu Ser Pro Tyr Thr Leu Ile Asp Ser Leu
    690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
            740                 745                 750

Asp Val Cys Arg Asn Ile Ile Phe Ser Ile Ser Ala Leu Leu His Gln
        755                 760                 765

Thr Gly Leu Ala Cys Glu Cys Asp Pro Gln Gly Ser Leu Ser Ser Val
    770                 775                 780

Cys Asp Pro Asn Gly Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
            820                 825                 830

Cys Asn Pro Val Thr Gly Gln Cys His Cys Phe Gln Gly Val Tyr Ala
        835                 840                 845

Arg Gln Cys Asp Arg Cys Leu Pro Gly His Trp Gly Phe Pro Ser Cys
    850                 855                 860

Gln Pro Cys Gln Cys Asn Gly His Ala Asp Asp Cys Asp Pro Val Thr
865                 870                 875                 880

Gly Glu Cys Leu Asn Cys Gln Asp Tyr Thr Met Gly His Asn Cys Glu
                885                 890                 895

Arg Cys Leu Ala Gly Tyr Tyr Gly Asp Pro Ile Ile Gly Ser Gly Asp
            900                 905                 910

His Cys Arg Pro Cys Pro Cys Pro Asp Gly Pro Asp Ser Gly Arg Gln
        915                 920                 925
```

-continued

Phe Ala Arg Ser Cys Tyr Gln Asp Pro Val Thr Leu Gln Leu Ala Cys
930                935                940

Val Cys Asp Pro Gly Tyr Ile Gly Ser Arg Cys Asp Asp Cys Ala Ser
945                950                955                960

Gly Tyr Phe Gly Asn Pro Ser Glu Val Gly Gly Ser Cys Gln Pro Cys
                965                970                975

Gln Cys His Asn Asn Ile Asp Thr Thr Asp Pro Glu Ala Cys Asp Lys
            980                985                990

Glu Thr Gly Arg Cys Leu Lys Cys Leu Tyr His Thr Glu Gly Glu His
        995                1000                1005

Cys Gln Phe Cys Arg Phe Gly Tyr Tyr Gly Asp Ala Leu Gln Gln
    1010                1015                1020

Asp Cys Arg Lys Cys Val Cys Asn Tyr Leu Gly Thr Val Gln Glu
    1025                1030                1035

His Cys Asn Gly Ser Asp Cys Gln Cys Asp Lys Ala Thr Gly Gln
    1040                1045                1050

Cys Leu Cys Leu Pro Asn Val Ile Gly Gln Asn Cys Asp Arg Cys
    1055                1060                1065

Ala Pro Asn Thr Trp Gln Leu Ala Ser Gly Thr Gly Cys Asp Pro
    1070                1075                1080

Cys Asn Cys Asn Ala Ala His Ser Phe Gly Pro Ser Cys Asn Glu
    1085                1090                1095

Phe Thr Gly Gln Cys Gln Cys Met Pro Gly Phe Gly Gly Arg Thr
    1100                1105                1110

Cys Ser Glu Cys Gln Glu Leu Phe Trp Gly Asp Pro Asp Val Glu
    1115                1120                1125

Cys Arg Ala Cys Asp Cys Asp Pro Arg Gly Ile Glu Thr Pro Gln
    1130                1135                1140

Cys Asp Gln Ser Thr Gly Gln Cys Val Cys Val Glu Gly Val Glu
    1145                1150                1155

Gly Pro Arg Cys Asp Lys Cys Thr Arg Gly Tyr Ser Gly Val Phe
    1160                1165                1170

Pro Asp Cys Thr Pro Cys His Gln Cys Phe Ala Leu Trp Asp Val
    1175                1180                1185

Ile Ile Ala Glu Leu Thr Asn Arg Thr His Arg Phe Leu Glu Lys
    1190                1195                1200

Ala Lys Ala Leu Lys Ile Ser Gly Val Ile Gly Pro Tyr Arg Glu
    1205                1210                1215

Thr Val Asp Ser Val Glu Arg Lys Val Ser Glu Ile Lys Asp Ile
    1220                1225                1230

Leu Ala Gln Ser Pro Ala Ala Glu Pro Leu Lys Asn Ile Gly Asn
    1235                1240                1245

Leu Phe Glu Glu Ala Glu Lys Leu Ile Lys Asp Val Thr Glu Met
    1250                1255                1260

Met Ala Gln Val Glu Val Lys Leu Ser Asp Thr Thr Ser Gln Ser
    1265                1270                1275

Asn Ser Thr Ala Lys Glu Leu Asp Ser Leu Gln Thr Glu Ala Glu
    1280                1285                1290

Ser Leu Asp Asn Thr Val Lys Glu Leu Ala Glu Gln Leu Glu Phe
    1295                1300                1305

Ile Lys Asn Ser Asp Ile Arg Gly Ala Leu Asp Ser Ile Thr Lys
    1310                1315                1320

Tyr Phe Gln Met Ser Leu Glu Ala Glu Glu Arg Val Asn Ala Ser

-continued

```
            1325                1330                1335
Thr Thr Glu Pro Asn Ser Thr Val Glu Gln Ser Ala Leu Met Arg
        1340                1345                1350

Asp Arg Val Glu Asp Val Met Met Glu Arg Glu Ser Gln Phe Lys
        1355                1360                1365

Glu Lys Gln Glu Glu Gln Ala Arg Leu Leu Asp Glu Leu Ala Gly
        1370                1375                1380

Lys Leu Gln Ser Leu Asp Leu Ser Ala Ala Ala Glu Met Thr Cys
        1385                1390                1395

Gly Thr Pro Pro Gly Ala Ser Cys Ser Glu Thr Glu Cys Gly Gly
        1400                1405                1410

Pro Asn Cys Arg Thr Asp Glu Gly Glu Arg Lys Cys Gly Gly Pro
        1415                1420                1425

Gly Cys Gly Gly Leu Val Thr Val Ala His Asn Ala Trp Gln Lys
        1430                1435                1440

Ala Met Asp Leu Asp Gln Asp Val Leu Ser Ala Leu Ala Glu Val
        1445                1450                1455

Glu Gln Leu Ser Lys Met Val Ser Glu Ala Lys Leu Arg Ala Asp
        1460                1465                1470

Glu Ala Lys Gln Ser Ala Glu Asp Ile Leu Leu Lys Thr Asn Ala
        1475                1480                1485

Thr Lys Glu Lys Met Asp Lys Ser Asn Glu Glu Leu Arg Asn Leu
        1490                1495                1500

Ile Lys Gln Ile Arg Asn Phe Leu Thr Gln Asp Ser Ala Asp Leu
        1505                1510                1515

Asp Ser Ile Glu Ala Val Ala Asn Glu Val Leu Lys Met Glu Met
        1520                1525                1530

Pro Ser Thr Pro Gln Gln Leu Gln Asn Leu Thr Glu Asp Ile Arg
        1535                1540                1545

Glu Arg Val Glu Ser Leu Ser Gln Val Glu Val Ile Leu Gln His
        1550                1555                1560

Ser Ala Ala Asp Ile Ala Arg Ala Glu Met Leu Leu Glu Glu Ala
        1565                1570                1575

Lys Arg Ala Ser Lys Ser Ala Thr Asp Val Lys Val Thr Ala Asp
        1580                1585                1590

Met Val Lys Glu Ala Leu Glu Glu Ala Glu Lys Ala Gln Val Ala
        1595                1600                1605

Ala Glu Lys Ala Ile Lys Gln Ala Asp Glu Asp Ile Gln Gly Thr
        1610                1615                1620

Gln Asn Leu Leu Thr Ser Ile Glu Ser Glu Thr Ala Ala Ser Glu
        1625                1630                1635

Glu Thr Leu Phe Asn Ala Ser Gln Arg Ile Ser Glu Leu Glu Arg
        1640                1645                1650

Asn Val Glu Glu Leu Lys Arg Lys Ala Ala Gln Asn Ser Gly Glu
        1655                1660                1665

Ala Glu Tyr Ile Glu Lys Val Val Tyr Thr Val Lys Gln Ser Ala
        1670                1675                1680

Glu Asp Val Lys Lys Thr Leu Asp Gly Glu Leu Asp Glu Lys Tyr
        1685                1690                1695

Lys Lys Val Glu Asn Leu Ile Ala Lys Lys Thr Glu Glu Ser Ala
        1700                1705                1710

Asp Ala Arg Arg Lys Ala Glu Met Leu Gln Asn Glu Ala Lys Thr
        1715                1720                1725
```

| | | | | | | | | | | |
|---|---|---|---|---|---|---|---|---|---|---|
| Leu | Leu | Ala | Gln | Ala | Asn | Ser | Lys | Leu | Gln | Leu | Leu | Lys | Asp | Leu |
| | 1730 | | | | 1735 | | | | 1740 | |

Glu Arg Lys Tyr Glu Asp Asn Gln Arg Tyr Leu Glu Asp Lys Ala
    1745              1750              1755

Gln Glu Leu Ala Arg Leu Glu Gly Glu Val Arg Ser Leu Leu Lys
    1760              1765              1770

Asp Ile Ser Gln Lys Val Ala Val Tyr Ser Thr Cys Leu
    1775              1780              1785

<210> SEQ ID NO 5
<211> LENGTH: 5817
<212> TYPE: DNA
<213> ORGANISM: Homo sapiens

<400> SEQUENCE: 5

```
gaaggcagtt tccggaggga aggggtaggg ttggggtggg ggcgctctcc gcccggtgtt      60
gcgctccttc ccagaatccg ctccggcctt tccttcctgc cgcgattccc aactttgctc     120
aaagtcgctg gactctaagc tgtcggaggg accgctggac agacctggga actgacagag     180
ggcctggagg gaaacaggcc aaagacccac aggcagagtt gacacggaac cccaaagcaa     240
ggaggagggc tcgggcccga gaccgttcac ctccccttat ccctgttccc ctcttcagga     300
tggagctgac ctcaagggaa agagggaggg gacagcctct gccctgggaa cttcgactgg     360
gcctactgct aagcgtgctg gctgccacac tggcacaggc ccctgccccg gatgtgcctg     420
gctgttccag gggaagctgc taccccgcca cgggcgacct gctggtgggc cgagctgaca     480
gactgactgc ctcatccact tgtggcctga atggccccca gccctactgc atcgtcagtc     540
acctgcagga cgaaaagaag tgcttccttt gtgactcccg cgcccccttc tctgctagag     600
acaacccaca cagccatcgc atccagaatg tagtcaccag ctttgcacca cagcggcggg     660
cagcctggtg gcagtcagag aatggtatcc ctgcggtcac catccagctg acctggaggg     720
ctgagtttca tttcacacac ctcattatga ccttcaagac atttcgccct gctgccatgc     780
tggtggaacg ctcagcagac tttggccgca cctggcatgt gtaccgatat ttctcctatg     840
actgtgggc tgacttccca ggagtcccac tagcaccccc acggcactgg gatgatgtag     900
tctgtgagtc ccgctactca gagattgagc catccactga aggcgaggtc atctatcgtg     960
tgctggaccc tgccatccct atcccagacc cctacagctc acggattcag aacctgttga    1020
agatcaccaa cctacgggtg aacctgactc gtctacacac gttgggagac aacctactcg    1080
acccacggag ggagatccga gagaagtact actatgccct ctatgagctg gttgtacgtg    1140
gcaactgctt ctgctacgga cacgcctcag agtgtgcacc cgccccaggg gcaccagccc    1200
atgctgaggg catggtgcac ggagcttgca tctgcaaaca caacacacgt ggcctcaact    1260
gcgagcagtg tcaggatttc tatcgtgacc tgccctggcg tccggctgag gacggccata    1320
gtcatgcctg taggaagtgt gagtgccatg gcacaccca gctgccacac ttcgacatgg    1380
```

```
gcactccttg tgaccccaac agtggatcct gttactgcaa acgtctagtg actggacgtg    1800
gatgtgaccg ctgcctgcct ggccactggg gcctgagcca cgacctgctc ggctgccgcc    1860
cctgtgactg cgacgtgggt ggtgctttgg atccccagtg tgatgagggc acaggtcaat    1920
gccactgccg ccagcacatg gttgggcgac gctgtgagca ggtgcaacct ggctacttcc    1980
ggcccttcct ggaccaccta atttgggagg ctgaggacac ccgagggcag gtgctcgatg    2040
tggtggagcg cctggtgacc cccggggaaa ctccatcctg gactggctca ggcttcgtgc    2100
ggctacagga aggtcagacc ctggagttcc tggtggcctc tgtgccgaag ctatggact     2160
atgacctgct gctgcgctta gagccccagg tccctgagca atgggcagag ttggaactga    2220
ttgtgcagcg tccagggcct gtgcctgccc acagcctgtg tgggcatttg gtgcccaagg    2280
atgatcgcat ccaagggact ctgcaaccac atgccaggta cttgatattt cctaatcctg    2340
tctgccttga gcctggtatc tcctacaagc tgcatctgaa gctggtacgg acaggggaa     2400
gtgcccagcc tgagactccc tactctggac ctggcctgct cattgactcg ctggtgctgc    2460
tgccccgtgt cctggtgcta gagatgttta gtggggtga tgctgctgcc ctggagcgcc     2520
aggccacctt tgaacgctac caatgccatg aggagggtct ggtgcccagc aagacttctc    2580
cctctgaggc ctgcgcaccc ctcctcatca gcctgtccac cctcatctac aatggtgccc    2640
tgccatgtca gtgcaaccct caaggttcac tgagttctga gtgcaaccct catggtggtc    2700
agtgcctgtg caagcctgga gtggttgggc gccgctgtga cctctgtgcc cctggctact    2760
atggctttgg ccccacaggc tgtcaagcct gccagtgcag ccacgagggg gcactcagca    2820
gtctctgtga aaagaccagt gggcaatgtc tctgtcgaac tggtgccttt gggcttcgct    2880
gtgaccgctg ccagcgtggc cagtggggat tccctagctg ccggccatgt gtctgcaatg    2940
ggcatgcaga tgagtgcaac acccacacag gcgcttgcct gggctgccgt gatcacacag    3000
ggggtgagca ctgtgaaagg tgcattgctg gtttccacgg ggaccacgg ctgccatatg      3060
ggggccagtg ccgccctgt ccctgtcctg aaggccctgg gagccaacgg cactttgcta      3120
cttcttgcca ccaggatgaa tattcccagc agattgtgtg ccactgccgg gcaggctata    3180
cggggctgcg atgtgaagct tgtgcccctg ggcactttgg ggacccatca aggccaggtg    3240
gccggtgcca actgtgtgag tgcagtggga acattgaccc aatggatcct gatgcctgtg    3300
acccccacac gggcaatgc ctgcgctgtt tacaccacac agagggtcca cactgtgccc      3360
actgcaagcc tggcttccat gggcaggctg cccgacagag ctgtcaccgc tgcacatgca    3420
acctgctggg cacaaatccg cagcagtgcc catctcctga ccagtgccac tgtgatccaa    3480
gcagtgggca gtgcccatgc ctccccaatg tccagggccc tagctgtgac cgctgtgccc    3540
ccaacttctg gaacctcacc agtggccatg gttgccagcc ttgtgcctgc cacccaagcc    3600
gggccagagg ccccacctgc aacgagttca gggcagtg ccactgccgt gccggctttg       3660
gagggcggac ttgttctgag tgccaagagc tccactgggg agaccctggg ttgcagtgcc    3720
atgcctgtga ttgtgactct cgtggaatag atacacctca gtgtcaccgc ttcacaggtc    3780
actgcagctg ccgcccaggg gtgtctggtg tgcgctgtga ccagtgtgcc cgtggcttct    3840
caggaatctt tcctgcctgc catccctgcc atgcatgctt cggggattgg gaccgagtgg    3900
tgcaggactt ggcagcccgt acacagcgcc tagagcagcg ggcgcaggag ttgcaacaga    3960
cgggtgtgct gggtgccttt gagagcagct tctggacat gcaggagaag ctgggcattg     4020
tgcagggcat cgtaggtgcc cgcaacacct cagccgcctc cactgcacag cttgtggagg    4080
ccacagagga gctgcggcgt gaaattgggg aggccactga gcacctgact cagctcgagg    4140
```

-continued

```
cagacctgac agatgtgcaa gatgagaact tcaatgccaa ccatgcacta agtggtctgg    4200
agcgagatag gcttgcactt aatctcacac tgcggcagct cgaccagcat cttgacttgc    4260
tcaaacattc aaacttcctg ggtgcctatg acagcatccg gcatgcccat agccagtctg    4320
cagaggcaga acgtcgtgcc aatacctcag ccctggcagt acctagccct gtgagcaact    4380
cggcaagtgc tcggcatcgg acagaggcac tgatggatgc tcagaaggag gacttcaaca    4440
gcaaacacat ggccaaccag cgggcacttg gcaagctctc tgcccatacc cacaccctga    4500
gcctgacaga cataaatgag ctggtgtgtg gggcaccagg ggatgcaccc tgtgctacaa    4560
gcccttgtgg gggtgccggc tgtcgagatg aggatgggca gccgcgctgt gggggcctca    4620
gctgcaatgg ggcagcggct acagcagacc tagcactggg ccgggcccgg cacacacagg    4680
cagagctgca gcgggcactg gcagaaggtg gtagcatcct cagcagagtg gctgagactc    4740
gtcggcaggc aagcgaggca cagcagcggg cccaggcagc cctggacaag gctaatgctt    4800
ccaggggaca ggtggaacag gccaaccagg aacttcaaga acttatccag agtgtgaagg    4860
acttcctcaa ccaggagggg gctgatcctg atagcattga aatggtggcc acacgggtgc    4920
tagagctctc catcccagct tcagctgagc agatccagca cctggcgggt gcgattgcag    4980
agcgagtccg gagcctggca gatgtggatg cgatcctggc acgtactgta ggagatgtgc    5040
gtcgtgccga gcagctactg caggatgcac ggcgggcaag gagctgggct gaggatgaga    5100
aacagaaggc agagacagta caggcagcac tggaggaggc ccagcgggca cagggtattg    5160
cccagggtgc catccggggg gcagtggctg acacacggga cacagagcag accctgtacc    5220
aggtacagga gaggatggca ggtgcagagc gggcactgag ctctgcaggt gaaagggctc    5280
ggcagttgga tgctctcctg gaggctctga aattgaaacg gcaggaaat agtctggcag    5340 cctctacagc agaagaaacg gcaggcagtg cccagggtcg tgcccaggag gctgagcagc    5400
tgctacgcgg tcctctgggt gatcagtacc agacggtgaa ggcctagct gagcgcaagg    5460 cccaaggtgt gctggctgca caggcaaggg cagaacaact gcgggatgag gctcgggacc    5520
tgttgcaagc cgctcaggac aagctgcagc ggctacagga attggaaggc acctatgagg    5580
aaaatgagcg ggcactggag agtaaggcag cccagttgga cgggttggag gccaggatgc    5640
gcagcgtgct tcaagccatc aacttgcagg tgcagatcta caacacctgc cagtgacccc    5700
tgcccaaggc ctaccccagt tcctagcact gccccacatg catgtctgcc tatgcactga    5760
agagctcttg gccggcagg gccccaata aaccagtgtg aacccccaaa aaaaaaa       5817
```

<210> SEQ ID NO 6
<211> LENGTH: 1798
<212> TYPE: PRT
<213> ORGANISM: Homo sapiens

<400> SEQUENCE: 6

```
Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
            20                  25                  30

Gln Ala Pro Ala Pro Asp Val Pro Gly Cys Ser Arg Gly Ser Cys Tyr
        35                  40                  45

Pro Ala Thr Gly Asp Leu Leu Val Gly Arg Ala Asp Arg Leu Thr Ala
    50                  55                  60

Ser Ser Thr Cys Gly Leu Asn Gly Pro Gln Pro Tyr Cys Ile Val Ser
65                  70                  75                  80
```

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
            115                 120                 125

Gly Ile Pro Ala Val Thr Ile Gln Leu Asp Leu Glu Ala Glu Phe His
        130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
            195                 200                 205

Ile Glu Pro Ser Thr Glu Gly Glu Val Ile Tyr Arg Val Leu Asp Pro
210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
            245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
            275                 280                 285

Ala Ser Glu Cys Ala Pro Ala Pro Gly Ala Pro Ala His Ala Glu Gly
            290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
                325                 330                 335

Glu Asp Gly His Ser His Ala Cys Arg Lys Cys Glu Cys His Gly His
            340                 345                 350

Thr His Ser Cys His Phe Asp Met Ala Val Tyr Leu Ala Ser Gly Asn
            355                 360                 365

Val Ser Gly Gly Val Cys Asp Gly Cys Gln His Asn Thr Ala Gly Arg
        370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415

Ser Gln Asp Gly Gly Arg Cys Asp Ser His Asp Asp Pro Ala Leu Gly
            420                 425                 430

Leu Val Ser Gly Gln Cys Arg Cys Lys Glu His Val Val Gly Thr Arg
            435                 440                 445

Cys Gln Gln Cys Arg Asp Gly Phe Phe Gly Leu Ser Ile Ser Asp Arg
            450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
            485                 490                 495

-continued

Val Thr Gly Arg Gly Cys Asp Arg Cys Leu Pro Gly His Trp Gly Leu
            500                 505                 510

Ser His Asp Leu Leu Gly Cys Arg Pro Cys Asp Cys Asp Val Gly Gly
        515                 520                 525

Ala Leu Asp Pro Gln Cys Asp Glu Gly Thr Gly Gln Cys His Cys Arg
    530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
            580                 585                 590

Ser Trp Thr Gly Ser Gly Phe Val Arg Leu Gln Glu Gly Gln Thr Leu
        595                 600                 605

Glu Phe Leu Val Ala Ser Val Pro Lys Ala Met Asp Tyr Asp Leu Leu
    610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
            660                 665                 670

Arg Tyr Leu Ile Phe Pro Asn Pro Val Cys Leu Glu Pro Gly Ile Ser
        675                 680                 685

Tyr Lys Leu His Leu Lys Leu Val Arg Thr Gly Gly Ser Ala Gln Pro
    690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
            740                 745                 750

Gly Leu Val Pro Ser Lys Thr Ser Pro Ser Glu Ala Cys Ala Pro Leu
        755                 760                 765

Leu Ile Ser Leu Ser Thr Leu Ile Tyr Asn Gly Ala Leu Pro Cys Gln
    770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Leu Cys
                805                 810                 815

Ala Pro Gly Tyr Tyr Gly Phe Gly Pro Thr Gly Cys Gln Ala Cys Gln
            820                 825                 830

Cys Ser His Glu Gly Ala Leu Ser Ser Leu Cys Glu Lys Thr Ser Gly
        835                 840                 845

Gln Cys Leu Cys Arg Thr Gly Ala Phe Gly Leu Arg Cys Asp Arg Cys
    850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
            900                 905                 910

His Gly Asp Pro Arg Leu Pro Tyr Gly Gly Gln Cys Arg Pro Cys Pro

-continued

```
                915                 920                 925
    Cys Pro Glu Gly Pro Gly Ser Gln Arg His Phe Ala Thr Ser Cys His
        930                 935                 940
    Gln Asp Glu Tyr Ser Gln Gln Ile Val Cys His Cys Arg Ala Gly Tyr
    945                 950                 955                 960
    Thr Gly Leu Arg Cys Glu Ala Cys Ala Pro Gly His Phe Gly Asp Pro
                    965                 970                 975
    Ser Arg Pro Gly Gly Arg Cys Gln Leu Cys Glu Cys Ser Gly Asn Ile
                        980                 985                 990
    Asp Pro Met Asp Pro Asp Ala Cys Asp Pro His Thr Gly Gln Cys Leu
                        995                1000                1005
    Arg Cys Leu His His Thr Glu Gly Pro His Cys Ala His Cys Lys
            1010                1015                1020
    Pro Gly Phe His Gly Gln Ala Ala Arg Gln Ser Cys His Arg Cys
            1025                1030                1035
    Thr Cys Asn Leu Leu Gly Thr Asn Pro Gln Gln Cys Pro Ser Pro
            1040                1045                1050
    Asp Gln Cys His Cys Asp Pro Ser Ser Gly Gln Cys Pro Cys Leu
            1055                1060                1065
    Pro Asn Val Gln Gly Pro Ser Cys Asp Arg Cys Ala Pro Asn Phe
            1070                1075                1080
    Trp Asn Leu Thr Ser Gly His Gly Cys Gln Pro Cys Ala Cys His
            1085                1090                1095
    Pro Ser Arg Ala Arg Gly Pro Thr Cys Asn Glu Phe Thr Gly Gln
            1100                1105                1110
    Cys His Cys Arg Ala Gly Phe Gly Gly Arg Thr Cys Ser Glu Cys
            1115                1120                1125
    Gln Glu Leu His Trp Gly Asp Pro Gly Leu Gln Cys His Ala Cys
            1130                1135                1140
    Asp Cys Asp Ser Arg Gly Ile Asp Thr Pro Gln Cys His Arg Phe
            1145                1150                1155
    Thr Gly His Cys Ser Cys Arg Pro Gly Val Ser Gly Val Arg Cys
            1160                1165                1170
    Asp Gln Cys Ala Arg Gly Phe Ser Gly Ile Phe Pro Ala Cys His
            1175                1180                1185
    Pro Cys His Ala Cys Phe Gly Asp Trp Asp Arg Val Val Gln Asp
            1190                1195                1200
    Leu Ala Ala Arg Thr Gln Arg Leu Glu Gln Arg Ala Gln Glu Leu
            1205                1210                1215
    Gln Gln Thr Gly Val Leu Gly Ala Phe Glu Ser Ser Phe Trp His
            1220                1225                1230
    Met Gln Glu Lys Leu Gly Ile Val Gln Gly Ile Val Gly Ala Arg
            1235                1240                1245
    Asn Thr Ser Ala Ala Ser Thr Ala Gln Leu Val Glu Ala Thr Glu
            1250                1255                1260
    Glu Leu Arg Arg Glu Ile Gly Glu Ala Thr Glu His Leu Thr Gln
            1265                1270                1275
    Leu Glu Ala Asp Leu Thr Asp Val Gln Asp Glu Asn Phe Asn Ala
            1280                1285                1290
    Asn His Ala Leu Ser Gly Leu Glu Arg Asp Arg Leu Ala Leu Asn
            1295                1300                1305
    Leu Thr Leu Arg Gln Leu Asp Gln His Leu Asp Leu Leu Lys His
            1310                1315                1320
```

```
Ser Asn Phe Leu Gly Ala Tyr Asp Ser Ile Arg His Ala His Ser
1325                1330                1335

Gln Ser Ala Glu Ala Glu Arg Arg Ala Asn Thr Ser Ala Leu Ala
1340                1345                1350

Val Pro Ser Pro Val Ser Asn Ser Ala Ser Ala Arg His Arg Thr
1355                1360                1365

Glu Ala Leu Met Asp Ala Gln Lys Glu Asp Phe Asn Ser Lys His
1370                1375                1380

Met Ala Asn Gln Arg Ala Leu Gly Lys Leu Ser Ala His Thr His
1385                1390                1395

Thr Leu Ser Leu Thr Asp Ile Asn Glu Leu Val Cys Gly Ala Pro
1400                1405                1410

Gly Asp Ala Pro Cys Ala Thr Ser Pro Cys Gly Gly Ala Gly Cys
1415                1420                1425

Arg Asp Glu Asp Gly Gln Pro Arg Cys Gly Gly Leu Ser Cys Asn
1430                1435                1440

Gly Ala Ala Thr Ala Asp Leu Ala Leu Gly Arg Ala Arg His
1445                1450                1455

Thr Gln Ala Glu Leu Gln Arg Ala Leu Ala Glu Gly Gly Ser Ile
1460                1465                1470

Leu Ser Arg Val Ala Glu Thr Arg Arg Gln Ala Ser Glu Ala Gln
1475                1480                1485

Gln Arg Ala Gln Ala Ala Leu Asp Lys Ala Asn Ala Ser Arg Gly
1490                1495                1500

Gln Val Glu Gln Ala Asn Gln Glu Leu Gln Glu Leu Ile Gln Ser
1505                1510                1515

Val Lys Asp Phe Leu Asn Gln Glu Gly Ala Asp Pro Asp Ser Ile
1520                1525                1530

Glu Met Val Ala Thr Arg Val Leu Glu Leu Ser Ile Pro Ala Ser
1535                1540                1545

Ala Glu Gln Ile Gln His Leu Ala Gly Ala Ile Ala Glu Arg Val
1550                1555                1560

Arg Ser Leu Ala Asp Val Asp Ala Ile Leu Ala Arg Thr Val Gly
1565                1570                1575

Asp Val Arg Arg Ala Glu Gln Leu Leu Gln Asp Ala Arg Arg Ala
1580                1585                1590

Arg Ser Trp Ala Glu Asp Glu Lys Gln Lys Ala Glu Thr Val Gln
1595                1600                1605

Ala Ala Leu Glu Glu Ala Gln Arg Ala Gln Gly Ile Ala Gln Gly
1610                1615                1620

Ala Ile Arg Gly Ala Val Ala Asp Thr Arg Asp Thr Glu Gln Thr
1625                1630                1635

Leu Tyr Gln Val Gln Glu Arg Met Ala Gly Ala Glu Arg Ala Leu
1640                1645                1650

Ser Ser Ala Gly Glu Arg Ala Arg Gln Leu Asp Ala Leu Leu Glu
1655                1660                1665

Ala Leu Lys Leu Lys Arg Ala Gly Asn Ser Leu Ala Ala Ser Thr
1670                1675                1680

Ala Glu Glu Thr Ala Gly Ser Ala Gln Gly Arg Ala Gln Glu Ala
1685                1690                1695

Glu Gln Leu Leu Arg Gly Pro Leu Gly Asp Gln Tyr Gln Thr Val
1700                1705                1710
```

| | | | | | | | | |
|---|---|---|---|---|---|---|---|---|
| Lys | Ala | Leu | Ala | Glu | Arg | Lys | Ala | Gln | Gly | Val | Leu | Ala | Ala | Gln |

Lys Ala Leu Ala Glu Arg Lys Ala Gln Gly Val Leu Ala Ala Gln
1715                1720                1725

Ala Arg Ala Glu Gln Leu Arg Asp Glu Ala Arg Asp Leu Leu Gln
1730                1735                1740

Ala Ala Gln Asp Lys Leu Gln Arg Leu Gln Glu Leu Glu Gly Thr
1745                1750                1755

Tyr Glu Glu Asn Glu Arg Ala Leu Glu Ser Lys Ala Ala Gln Leu
1760                1765                1770

Asp Gly Leu Glu Ala Arg Met Arg Ser Val Leu Gln Ala Ile Asn
1775                1780                1785

Leu Gln Val Gln Ile Tyr Asn Thr Cys Gln
1790                1795

<210> SEQ ID NO 7
<211> LENGTH: 7889
<212> TYPE: DNA
<213> ORGANISM: Homo sapiens

<400> SEQUENCE: 7

```
gtgcaggctg ctcccggggt aggtgaggga agcgcggagg cggcgcgcgg gggcagtggt      60
cggcgagcag cgcggtcctc gctaggggcg cccacccgtc agtctctccg gcgcgagccg     120
ccgccaccgc ccgcgccgga gtcaggcccc tgggccccca ggctcaagca gcgaagcggc     180
ctccggggga cgccgctagg cgagaggaac gcgccggtgc ccttgccttc gccgtgaccc     240
agcgtgcggg cggcgggatg agagggagcc atcgggccgc gccggccctg cggccccggg     300
ggcggctctg gccgtgctg gccgtgctgg cggcggccgc cgcggcgggc tgtgcccagg       360
cagccatgga cgagtgcacg gacgagggcg ggcggccgca gcgctgcatg cccgagttcg     420
tcaacgccgc cttcaacgtg actgtggtgg ccaccaacac gtgtgggact ccgcccgagg     480
aatactgtgt gcagaccggg gtgaccgggg tcaccaagtc ctgtcacctg tgcgacgccg     540
ggcagcccca cctgcagcac ggggcagcct tcctgaccga ctacaacaac caggccgaca     600
ccacctggtg gcaaagccag accatgctgg ccggggtgca gtaccccagc tccatcaacc     660
tcacgctgca cctgggaaaa gcttttgaca tcacctatgt gcgtctcaag ttccacacca     720
gccgccgga gagctttgcc atttacaagc gcacacggga agacgggccc tggattcctt      780
accagtacta cagtggttcc tgtgagaaca cctactccaa ggcaaaccgc ggcttcatca     840
ggacaggagg ggacgagcag caggccttgt gtactgatga attcagtgac atttctcccc     900
tcactggggg caacgtggcc ttttctaccc tggaaggaag gcccagcgcc tataactttg     960
acaatagccc tgtgctgcag gaatgggtaa ctgccactga catcagagta actcttaatc    1020
gcctgaacac ttttggagat gaagtgttta acgatcccaa agttctcaag tcctattatt    1080
atgccatctc tgattttgct gtaggtggca gatgtaaatg taatggacac gcaagcgagt    1140
gtatgaagaa cgaatttgat aagctggtgt gtaattgcaa acataacaca tatgagtag     1200
actgtgaaaa gtgtcttcct ttcttcaatg accggccgtg gaggagggca actgcggaaa    1260
gtgccagtga atgcctgccc tgtgattgca atggtcgatc ccaggaatgc tacttcgacc    1320
ctgaactcta tcgttccact ggccatgggg ccactgtaca caactgccag gataacacag    1380
atggcgccca ctgtgagagg tgccgagaga acttcttccg ccttggcaac aatgaagcct    1440
gctcttcatg ccactgtagt cctgtgggct ctctaagcac acagtgtgat agttacggca    1500
gatgcagctg taagccagga gtgatggggg acaaatgtga ccgttgccag cctggattcc    1560
attctctcac tgaagcagga tgcaggccat gctcttgtga tccctctggc agcatagatg    1620
```

```
aatgtaatat tgaaacagga agatgtgttt gcaaagacaa tgtcgaaggc ttcaattgtg    1680
aaagatgcaa acctggattt tttaatctgg aatcatctaa tcctcggggt tgcacaccct    1740
gcttctgctt tgggcattct tctgtctgta caaacgctgt tggctacagt gtttattcta    1800
tctcctctac ctttcagatt gatgaggatg ggtggcgtgc ggaacagaga gatggctctg    1860
aagcatctct cgagtggtcc tctgagaggc aagatatcgc cgtgatctca gacagctact    1920
ttcctcggta cttcattgct cctgcaaagt tcttgggcaa gcaggtgttg agttatggtc    1980
agaacctctc cttctccttt cgagtggaca ggcgagatac tcgcctctct gcagaagacc    2040
ttgtgcttga gggagctggc ttaagagtat ctgtaccctt gatcgctcag gcaattcct     2100
atccaagtga gaccactgtg aagtatgtct tcaggctcca tgaagcaaca gattacccttg   2160
ggaggcctgc tcttacccct tttgaatttc agaagctcct aaacaacttg acctctatca    2220
agatacgtgg gacatacagt gagagaagtg ctggatattt ggatgatgtc accctggcaa    2280
gtgctcgtcc tgggcctgga gtccctgcaa cttgggtgga gtcctgcacc tgtcctgtgg    2340
gatatggagg gcagttttgt gagatgtgcc tctcaggtta cagaagagaa actcctaatc    2400
ttggaccata cagtccatgt gtgctttgcg cctgcaatgg acacagcgag acctgtgatc    2460
ctgagacagg tgtttgtaac tgcagagaca atacggctgg cccgcactgt gagaagtgca    2520
gtgatgggta ctatggagat tcaactgcag gcacctcctc cgattgccaa ccctgtccgt    2580
gtcctggagg ttcaagttgt gctgttgttc ccaagacaaa ggaggtggtg tgcaccaact    2640
gtcctactgg caccactggt aagagatgtg agctctgtga tgatggctac tttggagacc    2700
ccctgggtag aaacggccct gtgagacttt gccgcctgtg ccagtgcagt gacaacatcg    2760
atcccaatgc agttggaaat tgcaatcgct tgacgggaga atgcctgaag tgcatctata    2820
acactgctgg cttctattgt gaccggtgca aagacggatt ttttggaaat cccctggctc    2880
ccaatccagc agacaaatgc aaagcctgca attgcaatct gtatgggacc atgaagcagc    2940
agagcagctg taaccccgtg acgggggcagt gtgaatgttt gcctcacgtg actggccagg   3000
actgtggtgc ttgtgacccct ggattctaca atctgcagag tgggcaaggc tgtgagaggt   3060
gtgactgcca tgccttgggc tccaccaatg ggcagtgtga catccgcacc ggccagtgtg    3120
agtgccagcc cggcatcact ggtcagcact gtgagcgctg tgaggtcaac cactttgggt    3180
ttggacctga aggctgcaaa ccctgtgact gtcatcctga gggatctctt tcacttcagt    3240
gcaaagatga tggtcgctgt gaatgcagag aaggctttgt gggaaatcgc tgtgaccagt    3300
gtgaagaaaa ctatttctac aatcggtctt ggcctggctg ccaggaatgt ccagcttgtt    3360
accggctggt aaaggataag gttgctgatc atagagtgaa gctccaggaa ttagagagtc    3420
tcatagcaaa ccttggaact ggggatgaga tggtgacaga tcaagccttc gaggatagac    3480
taaaggaagc agagagggaa gttatggacc tccttcgtga ggcccaggat gtcaaagatg    3540
ttgaccagaa tttgatggat cgcctacaga gagtgaataa cactctgtcc agccaaatta    3600
gccgtttaca gaatatccgg aataccattg aagagactgg aaacttggct gaacaagcgc    3660
gtgcccatgt agagaacaca gagcggttga ttgaaatcgc atccagagaa cttgagaaag    3720
caaaagtcgc tgctgccaat gtgtcagtca ctcagccaga atctacaggg gacccaaaca    3780
acatgactct tttggcagaa gaggctcgaa agcttgctga acgtcataaa caggaagctg    3840
atgacattgt tcgagtggca aagacagcca atgatacgtc aactgaggca tacaacctgc    3900
ttctgaggac actggcagga gaaaatcaaa cagcatttga gattgaagag cttaatagga    3960
```

```
agtatgaaca agcgaagaac atctcacagg atctggaaaa acaagctgcc cgagtacatg   4020
aggaggccaa aagggccggt gacaaagctg tggagatcta tgccagcgtg gctcagctga   4080 gcccttttgga ctctgagaca ctggagaatg aagcaaataa cataaagatg aagctgaga   4140 atctggaaca actgattgac cagaaattaa aagattatga ggacctcaga gaagatatga   4200
gagggaagga acttgaagtc aagaaccttc tggagaaagg caagactgaa cagcagaccg   4260
cagaccaact cctagcccga gctgatgctg ccaaggccct cgctgaagaa gctgcaaaga   4320
agggacggga taccttacaa gaagctaatg acattctcaa caacctgaaa gattttgata   4380
ggcgtgtgaa cgataacaag acggccgcag aggaggcact aaggaagatt cctgccatca   4440
accagaccat cactgaagcc aatgaaaaga ccagagaagc ccagcaggcc ctgggcagtg   4500
ctgcggcgga tgccacagag gccaagaaca aggcccatga ggcggagagg atcgcgagcg   4560
ctgtccaaaa gaatgccacc agcaccaagg cagaagctga agaacttttt gcagaagtta   4620
cagatctgga taatgaggtg aacaatatgt tgaagcaact gcaggaagca gaaaaagagc   4680
taaagagaaa acaagatgac gctgaccagg acatgatgat ggcagggatg gcttcacagg   4740
ctgctcaaga agccgagatc aatgccagaa aagccaaaaa ctctgttact agcctcctca   4800
gcattattaa tgacctcttg gagcagctgg ggcagctgga tacagtggac ctgaataagc   4860
taaacgagat tgaaggcacc ctaaacaaag ccaaagatga aatgaaggtc agcgatcttg   4920
ataggaaagt gtctgacctg gagaatgaag ccaagaagca ggaggctgcc atcatggact   4980
ataaccgaga tatcgaggag atcatgaagg acattcgcaa tctggaggac atcaggaaga   5040
ccttaccatc tggctgcttc aacaccccgt ccattgaaaa gccctagtgt ctttagggct   5100
ggaaggcagc atccctctga caggggggca gttgtgaggc cacagagtgc cttgacacaa   5160
agattacatt tttcagaccc ccactcctct gctgctgtcc atgactgtcc ttttgaacca   5220
ggaaaagtca cagagtttaa agagaagcaa attaaacatc ctgaatcggg aacaaagggt   5280
tttatctaat aaagtgtctc ttccattcac gttgctacct tacccacact ttcccttctg   5340
atttgcgtga ggacgtggca tcctacgtta ctgtacagtg gcataagcac atcgtgtgag   5400
cccatgtatg ctggggtaga gcaagtagcc ctcccctgtc tcatcgatac cagcagaacc   5460
tcctcagtct cagtactctt gtttctatga aggaaaagtt tggctactaa cagtagcatt   5520
gtgatggcca gtatatccag tccatggata aagaaaatgc atctgcatct cctacccctc   5580
ttccttctaa gcaaaaggaa ataaacatcc tgtgccaaag gtattggtca tttagaatgt   5640
cggtagccat ccatcagtgc ttttagttat tatgagtgta ggacactgag ccatccgtgg   5700
gtcaggatgc aattatttat aaaagtctcc aggtgaacat ggctgaagat ttttctagta   5760
tattaataat tgactaggaa gatgaacttt ttttcagatc tttgggcagc tgataattta   5820
aatctggatg ggcagcttgc actcaccaat agaccaaaag acatcttttg atattcttat   5880
aaatggaact tacacagaag aaatagggat atgataacca ctaaaatttt gttttcaaaa   5940
tcaaactaat tcttacagct ttttttattag ttagtcttgg aactagtgtt aagtatctgg   6000
cagagaacag ttaatcccta aggtcttgac aaaacagaag aaaaacaagc ctcctcgtcc   6060
tagtcttttc tagcaaaggg ataaaactta gatggcagct tgtactgtca gaatcccgtg   6120
tatccatttg ttcttctgtt ggagagatga gacatttgac ccttagctcc agttttcttc   6180
tgatgtttcc atcttccaga atccctcaaa aaacattgtt tgccaaatcc tggtggcaaa   6240
tacttgcact cagtatttca cacagctgcc aacgctatcg agttcctgca ctttgtgatt   6300
taaatccact ctaaaccttc cctctaagtg tagagggaag acccttacgt ggagtttcct   6360
```

```
agtgggcttc tcaacttttg atcctcagct ctgtggtttt aagaccacag tgtgacagtt    6420
ccctgccaca cacccccttc ctcctaccaa cccacctttg agattcatat atagccttta    6480
acactatgca actttgtact ttgcgtagca ggggcggggt ggggggaaag aaactattat    6540
ctgacacact ggtgctatta attatttcaa atttatattt ttgtgtgaat gttttgtgtt    6600
ttgtttatca tgattataga ataaggaatt tatgtaaata tacttagtcc tatttctaga    6660
atgcacatct gttcactttg ctcaattttt cctcttcact ggcacaatgt atctgaatac    6720
ctccttccct cccttctaga attctttgga ttgtactcca aagaattgtg ccttgtgttt    6780
gcagcatctc cattctctaa aattaatata attgctttcc tccacaccca gccactgtaa    6840
agaggtaact tgggtcctct tccattgcag tcctgatgat cctaacctgc agcacggtgg    6900
ttttacaatg ttccagagca ggaacgccag gttgacaagc tatggtagga ttaggaaagt    6960
ttgctgaaga ggatctttga cgccacagtg ggactagcca ggaatgaggg agaaatgccc    7020
tttctggcaa ttgttggagc tggataggta agttttataa gggagtacat tttgactgag    7080
cacttagggc atcaggaaca gtgctactta ctgatgggta gactgggaga ggtggtgtaa    7140
cttagttctt gatgatccca cttcctgttt ccatctgctt gggatatacc agagtttacc    7200
acaagtgttt tgacgatata ctcctgagct ttcactctgc tgcttctccc aggcctcttc    7260
tactatggca ggagatgtgg cgtgctgttg caaagttttc acgtcattgt ttcctggcta    7320
gttcatttca ttaagtggct acatcctaac atatgcattt ggtcaaggtt gcagaagagg    7380
actgaagatt gactgccaag ctagtttggg tgaagttcac tccagcaagt ctcaggccac    7440
aatggggtgg tttggtttgg tttcctttta actttctttt tgttatttgc ttttctcctc    7500
cacctgtgtg gtatattttt taagcagaat tttattttt aaaataaaag gttcttaca    7560 agatgatacc ttaattacac tcccgcaaca cagccattat tttattgtct agctccagtt    7620
atctgtattt tatgtaatgt aattgacagg atggctgctg cagaatgctg gttgacacag    7680
ggattattat actgctattt ttccctgaat ttttttcctt tgaattccaa ctgtggacct    7740
tttatatgtg ccttcacttt agctgtttgc cttaatctct acagccttgc tctccggggt    7800
ggttaataaa atgcaacact tggcattttt atgttttaag aaaaacagta ttttatttat    7860
aataaaatct gaatatttgt aaccctta                                      7889
```

<210> SEQ ID NO 8
<211> LENGTH: 1609
<212> TYPE: PRT
<213> ORGANISM: Homo sapiens

<400> SEQUENCE: 8

```
Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
            20                  25                  30

Ala Gln Ala Ala Met Asp Glu Cys Thr Asp Glu Gly Gly Arg Pro Gln
        35                  40                  45

Arg Cys Met Pro Glu Phe Val Asn Ala Ala Phe Asn Val Thr Val Val
    50                  55                  60

Ala Thr Asn Thr Cys Gly Thr Pro Glu Glu Tyr Cys Val Gln Thr
65                  70                  75                  80

Gly Val Thr Gly Val Thr Lys Ser Cys His Leu Cys Asp Ala Gly Gln
                85                  90                  95
```

-continued

```
Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
            180                 185                 190

Phe Ile Arg Thr Gly Gly Asp Glu Gln Gln Ala Leu Cys Thr Asp Glu
        195                 200                 205

Phe Ser Asp Ile Ser Pro Leu Thr Gly Gly Asn Val Ala Phe Ser Thr
    210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
            260                 265                 270

Tyr Tyr Tyr Ala Ile Ser Asp Phe Ala Val Gly Gly Arg Cys Lys Cys
        275                 280                 285

Asn Gly His Ala Ser Glu Cys Met Lys Asn Glu Phe Asp Lys Leu Val
    290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
        355                 360                 365

Asn Cys Gln Asp Asn Thr Asp Gly Ala His Cys Glu Arg Cys Arg Glu
    370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                405                 410                 415

Ser Cys Lys Pro Gly Val Met Gly Asp Lys Cys Asp Arg Cys Gln Pro
            420                 425                 430

Gly Phe His Ser Leu Thr Glu Ala Gly Cys Arg Pro Cys Ser Cys Asp
        435                 440                 445

Pro Ser Gly Ser Ile Asp Glu Cys Asn Ile Glu Thr Gly Arg Cys Val
    450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
                485                 490                 495

Cys Phe Gly His Ser Ser Val Cys Thr Asn Ala Val Gly Tyr Ser Val
            500                 505                 510

Tyr Ser Ile Ser Ser Thr Phe Gln Ile Asp Glu Asp Gly Trp Arg Ala
```

```
            515                 520                 525
Glu Gln Arg Asp Gly Ser Glu Ala Ser Leu Glu Trp Ser Ser Glu Arg
    530                 535                 540
Gln Asp Ile Ala Val Ile Ser Asp Ser Tyr Phe Pro Arg Tyr Phe Ile
545                 550                 555                 560
Ala Pro Ala Lys Phe Leu Gly Lys Gln Val Leu Ser Tyr Gly Gln Asn
                565                 570                 575
Leu Ser Phe Ser Phe Arg Val Asp Arg Arg Asp Thr Arg Leu Ser Ala
                580                 585                 590
Glu Asp Leu Val Leu Glu Gly Ala Gly Leu Arg Val Ser Val Pro Leu
                595                 600                 605
Ile Ala Gln Gly Asn Ser Tyr Pro Ser Glu Thr Thr Val Lys Tyr Val
    610                 615                 620
Phe Arg Leu His Glu Ala Thr Asp Tyr Pro Trp Arg Pro Ala Leu Thr
625                 630                 635                 640
Pro Phe Glu Phe Gln Lys Leu Leu Asn Asn Leu Thr Ser Ile Lys Ile
                645                 650                 655
Arg Gly Thr Tyr Ser Glu Arg Ser Ala Gly Tyr Leu Asp Asp Val Thr
                660                 665                 670
Leu Ala Ser Ala Arg Pro Gly Pro Gly Val Pro Ala Thr Trp Val Glu
                675                 680                 685
Ser Cys Thr Cys Pro Val Gly Tyr Gly Gly Gln Phe Cys Glu Met Cys
    690                 695                 700
Leu Ser Gly Tyr Arg Arg Glu Thr Pro Asn Leu Gly Pro Tyr Ser Pro
705                 710                 715                 720
Cys Val Leu Cys Ala Cys Asn Gly His Ser Glu Thr Cys Asp Pro Glu
                725                 730                 735
Thr Gly Val Cys Asn Cys Arg Asp Asn Thr Ala Gly Pro His Cys Glu
                740                 745                 750
Lys Cys Ser Asp Gly Tyr Tyr Gly Asp Ser Thr Ala Gly Thr Ser Ser
                755                 760                 765
Asp Cys Gln Pro Cys Pro Cys Pro Gly Gly Ser Ser Cys Ala Val Val
    770                 775                 780
Pro Lys Thr Lys Glu Val Val Cys Thr Asn Cys Pro Thr Gly Thr Thr
785                 790                 795                 800
Gly Lys Arg Cys Glu Leu Cys Asp Asp Gly Tyr Phe Gly Asp Pro Leu
                805                 810                 815
Gly Arg Asn Gly Pro Val Arg Leu Cys Arg Leu Cys Gln Cys Ser Asp
                820                 825                 830
Asn Ile Asp Pro Asn Ala Val Gly Asn Cys Asn Arg Leu Thr Gly Glu
                835                 840                 845
Cys Leu Lys Cys Ile Tyr Asn Thr Ala Gly Phe Tyr Cys Asp Arg Cys
    850                 855                 860
Lys Asp Gly Phe Phe Gly Asn Pro Leu Ala Pro Asn Pro Ala Asp Lys
865                 870                 875                 880
Cys Lys Ala Cys Asn Cys Asn Leu Tyr Gly Thr Met Lys Gln Gln Ser
                885                 890                 895
Ser Cys Asn Pro Val Thr Gly Gln Cys Glu Cys Leu Pro His Val Thr
                900                 905                 910
Gly Gln Asp Cys Gly Ala Cys Asp Pro Gly Phe Tyr Asn Leu Gln Ser
                915                 920                 925
Gly Gln Gly Cys Glu Arg Cys Asp Cys His Ala Leu Gly Ser Thr Asn
                930                 935                 940
```

```
Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
                965                 970                 975

Pro Glu Gly Cys Lys Pro Cys Asp Cys His Pro Glu Gly Ser Leu Ser
            980                 985                 990

Leu Gln Cys Lys Asp Asp Gly Arg  Cys Glu Cys Arg Glu  Gly Phe Val
        995                 1000                1005

Gly Asn  Arg Cys Asp Gln Cys  Glu Glu Asn Tyr Phe  Tyr Asn Arg
    1010                1015                1020

Ser Trp  Pro Gly Cys Gln Glu  Cys Pro Ala Cys Tyr  Arg Leu Val
    1025                1030                1035

Lys Asp  Lys Val Ala Asp His  Arg Val Lys Leu Gln  Glu Leu Glu
    1040                1045                1050

Ser Leu  Ile Ala Asn Leu Gly  Thr Gly Asp Glu Met  Val Thr Asp
    1055                1060                1065

Gln Ala  Phe Glu Asp Arg Leu  Lys Glu Ala Glu Arg  Glu Val Met
    1070                1075                1080

Asp Leu  Leu Arg Glu Ala Gln  Asp Val Lys Asp Val  Asp Gln Asn
    1085                1090                1095

Leu Met  Asp Arg Leu Gln Arg  Val Asn Asn Thr Leu  Ser Ser Gln
    1100                1105                1110

Ile Ser  Arg Leu Gln Asn Ile  Arg Asn Thr Ile Glu  Glu Thr Gly
    1115                1120                1125

Asn Leu  Ala Glu Gln Ala Arg  Ala His Val Glu Asn  Thr Glu Arg
    1130                1135                1140

Leu Ile  Glu Ile Ala Ser Arg  Glu Leu Glu Lys Ala  Lys Val Ala
    1145                1150                1155

Ala Ala  Asn Val Ser Val Thr  Gln Pro Glu Ser Thr  Gly Asp Pro
    1160                1165                1170

Asn Asn  Met Thr Leu Leu Ala  Glu Glu Ala Arg Lys  Leu Ala Glu
    1175                1180                1185

Arg His  Lys Gln Glu Ala Asp  Asp Ile Val Arg Val  Ala Lys Thr
    1190                1195                1200

Ala Asn  Asp Thr Ser Thr Glu  Ala Tyr Asn Leu Leu  Leu Arg Thr
    1205                1210                1215

Leu Ala  Gly Glu Asn Gln Thr  Ala Phe Glu Ile Glu  Glu Leu Asn
    1220                1225                1230

Arg Lys  Tyr Glu Gln Ala Lys  Asn Ile Ser Gln Asp  Leu Glu Lys
    1235                1240                1245

Gln Ala  Ala Arg Val His Glu  Glu Ala Lys Arg Ala  Gly Asp Lys
    1250                1255                1260

Ala Val  Glu Ile Tyr Ala Ser  Val Ala Gln Leu Ser  Pro Leu Asp
    1265                1270                1275

Ser Glu  Thr Leu Glu Asn Glu  Ala Asn Asn Ile Lys  Met Glu Ala
    1280                1285                1290

Glu Asn  Leu Glu Gln Leu Ile  Asp Gln Lys Leu Lys  Asp Tyr Glu
    1295                1300                1305

Asp Leu  Arg Glu Asp Met Arg  Gly Lys Glu Leu Glu  Val Lys Asn
    1310                1315                1320

Leu Leu  Glu Lys Gly Lys Thr  Glu Gln Gln Thr Ala  Asp Gln Leu
    1325                1330                1335
```

```
Leu Ala Arg Ala Asp Ala Ala Lys Ala Leu Ala Glu Glu Ala Ala
    1340            1345                1350

Lys Lys Gly Arg Asp Thr Leu Gln Glu Ala Asn Asp Ile Leu Asn
    1355            1360                1365

Asn Leu Lys Asp Phe Asp Arg Arg Val Asn Asp Asn Lys Thr Ala
    1370            1375                1380

Ala Glu Glu Ala Leu Arg Lys Ile Pro Ala Ile Asn Gln Thr Ile
    1385            1390                1395

Thr Glu Ala Asn Glu Lys Thr Arg Glu Ala Gln Gln Ala Leu Gly
    1400            1405                1410

Ser Ala Ala Asp Ala Thr Glu Ala Lys Asn Lys Ala His Glu
    1415            1420                1425

Ala Glu Arg Ile Ala Ser Ala Val Gln Lys Asn Ala Thr Ser Thr
    1430            1435                1440

Lys Ala Glu Ala Glu Arg Thr Phe Ala Glu Val Thr Asp Leu Asp
    1445            1450                1455

Asn Glu Val Asn Asn Met Leu Lys Gln Leu Gln Glu Ala Glu Lys
    1460            1465                1470

Glu Leu Lys Arg Lys Gln Asp Asp Ala Asp Gln Asp Met Met Met
    1475            1480                1485

Ala Gly Met Ala Ser Gln Ala Ala Gln Glu Ala Glu Ile Asn Ala
    1490            1495                1500

Arg Lys Ala Lys Asn Ser Val Thr Ser Leu Leu Ser Ile Ile Asn
    1505            1510                1515

Asp Leu Leu Glu Gln Leu Gly Gln Leu Asp Thr Val Asp Leu Asn
    1520            1525                1530

Lys Leu Asn Glu Ile Glu Gly Thr Leu Asn Lys Ala Lys Asp Glu
    1535            1540                1545

Met Lys Val Ser Asp Leu Asp Arg Lys Val Ser Asp Leu Glu Asn
    1550            1555                1560

Glu Ala Lys Lys Gln Glu Ala Ala Ile Met Asp Tyr Asn Arg Asp
    1565            1570                1575

Ile Glu Glu Ile Met Lys Asp Ile Arg Asn Leu Glu Asp Ile Arg
    1580            1585                1590

Lys Thr Leu Pro Ser Gly Cys Phe Asn Thr Pro Ser Ile Glu Lys
    1595            1600                1605

Pro
```

TREATMENT OF CORNEA USING LAMININ

CROSS-REFERENCE TO RELATED APPLICATIONS

This patent application is the U.S. national phase of International Patent Application No. PCT/JP2015/005473, filed Oct. 30, 2015, which claims the benefit of Japanese Patent Application No. 2014-222947, filed on Oct. 31, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 119,020 bytes ASCII (Text) file named "728061Sequence-Listing.txt," created Apr. 28, 2016.

TECHNICAL FIELD

The present invention relates to a novel therapy using a laminin. More specifically, the present invention is directed to ophthalmic therapy using a laminin and still more specifically directed to therapy and prophylaxis of corneal endothelia.

BACKGROUND ART

Human corneal endothelial cells are present at a density of about 3000 cells per $mm^2$ at birth. Human corneal endothelial cells do not have the ability to regenerate once they are damaged. In this manner, corneal endothelial cells are considered difficult to culture. Since culture and proliferation are currently difficult in transplantation techniques, treatment and surgery of corneal endothelia is practically impossible. There is a shortage in cornea donation in Japan, where the number of patients waiting for corneal transplantation is about 2600 whereas the number of corneal transplantations performed in Japan is approximately 1700 annually.

Patent Literatures 1 and 2 are known with regard to the relationship between laminins and ophthalmology.

CITATION LIST

Patent Literature

[PTL 1] Japanese National Phase PCT Laid-open Publication No. 2004-500012
[PTL 2] Japanese National Phase PCT Laid-open Publication No. 2003-532647

SUMMARY OF INVENTION

Solution to Problem

The inventors have discovered that specific laminins are useful in ophthalmic therapy, especially corneal endothelial therapy, on which the present invention is based. Thus, the present invention representatively provides the following.
(1) A therapeutic or prophylactic agent for a disease, a disorder, or a condition of a corneal endothelium, comprising at least one agent selected from the group consisting of laminins and fragments thereof.
(2) The therapeutic or prophylactic agent of item 1, wherein the laminins comprise an RGD sequence.
(3) The therapeutic or prophylactic agent of item 1 or 2, wherein the laminins comprise an α5 chain and/or a γ1 chain.
(4) The therapeutic or prophylactic agent of any one of items 1 to 3, wherein the laminins comprise laminin 511 (α5β1γ1) and laminin 521 (α5β2γ1).
(5) The therapeutic or prophylactic agent of any one of items 1 to 4, wherein the fragments have cell adhesion capability of a corneal endothelial cell.
(6) The therapeutic or prophylactic agent of any one of items 1 to 5, wherein the agent is laminin 511, laminin 521, or a laminin 511-E8 fragment.
(7) The therapeutic or prophylactic agent of any one of items 1 to 6, wherein the corneal endothelium is from a primate.
(8) The therapeutic or prophylactic agent of any one of items 1 to 7, wherein the disease, disorder, or condition of the corneal endothelium is selected from the group consisting of Fuchs' corneal endothelial dystrophy, corneal endotheliitis, trauma, and disorders and conditions from an ophthalmic surgery.
(9) The therapeutic or prophylactic agent of any one of items 1 to 8, wherein the disease, disorder, or condition of the corneal endothelium is selected from the group consisting of photophobia, blurred vision, visual impairment, ophthalmalgia, epiphora, hyperemia, pain, bullous keratopathy, eye discomfort, diminished contrast, glare, edema of the corneal stroma, bullous keratopathy, and corneal turbidity.
(10) The therapeutic or prophylactic agent of any one of items 1 to 9, wherein the corneal endothelium comprises a corneal endothelial layer, a Descemet's membrane, or both.
(11) The therapeutic or prophylactic agent of any one of items 1 to 10, wherein the corneal endothelium has a Descemet's membrane in a detached state.
(12) The therapeutic or prophylactic agent of any one of items 1 to 11, further comprising a corneal endothelial cell.
(13) The therapeutic or prophylactic agent of any one of items 1 to 11, further comprising a ROCK inhibitor.
(14) The therapeutic or prophylactic agent of any one of items 1 to 11, further comprising a corneal endothelial cell and a ROCK inhibitor.
(15) The therapeutic or prophylactic agent of item 13 or 14, wherein the ROCK inhibitor is selected from the group consisting of Y-27632 ((R)-(+)-trans-(4-pyridyl)-4-(1-aminoethyl)-cyclohexanecarboxamide dihydrochloride monohydrate) and a pharmaceutically acceptable salt thereof.
(16) The therapeutic or prophylactic agent of any one of items 1 to 15, wherein the agent is injected into an eye thereby being contacted with tissue in the eye.
(17) The therapeutic or prophylactic agent of any one of items 1 to 16, wherein the agent is present at about 21 nM or greater.
(18) The therapeutic or prophylactic agent of any one of items 1 to 17, wherein a corneal endothelial cell is further administered.
(19) The therapeutic or prophylactic agent of any one of items 1 to 18, wherein the agent is provided while being mixed with a corneal endothelial cell, and at least one agent selected from the group consisting of laminins and fragments thereof is injected into an eye thereby being contacted with tissue in the eye.
(20) The therapeutic or prophylactic agent of any one of items 1 to 19, further comprising a ROCK inhibitor.
(21) The therapeutic or prophylactic agent of any one of items 1 to 20, wherein the ROCK inhibitor is selected from the group consisting of Y-27632 ((R)-(+)-trans-(4-pyridyl)-

4-(1-aminoethyl)-cyclohexanecarboxamide dihydrochloride monohydrate) and a pharmaceutically acceptable salt thereof.

(22) The therapeutic or prophylactic agent of any one of items 1 to 21, wherein the agent mixed with the corneal endothelial cell is about 2.1 nM or greater, and the agent to be injected is about 21 nM or greater.

(23) At least one agent selected from the group consisting of laminins and fragments thereof for use in therapy or prophylaxis of a disease, a disorder, or a condition of a corneal endothelium.

(24) The agent of item 23, further comprising a feature described in one or more of items 2 to 22.

(25) A method for therapy or prophylaxis of a disease, a disorder, or a condition of a corneal endothelium, the method comprising administering an effective amount of at least one agent selected from the group consisting of laminins and fragments thereof to a subject in need of the therapy or prophylaxis.

(26) The method of item 25, further comprising a feature described in one or more of items 2 to 11.

(27) The method of item 26 or 26, further comprising administering a corneal endothelial cell to the subject.

(28) The method of any one of items 25 to 27, further comprising administering a ROCK inhibitor to the subject.

(29) The method of item 28, wherein the ROCK inhibitor is selected from the group consisting of Y-27632 ((R)-(+)-trans-(4-pyridyl)-4-(1-aminoethyl)-cyclohexanecarboxamide dihydrochloride monohydrate) and a pharmaceutically acceptable salt thereof.

(30) The method of any one of items 25 to 29, further comprising administering a corneal endothelial cell and a ROCK inhibitor to the subject.

(31) The method of any one of items 25 to 30, wherein the agent is injected into an eye of the subject thereby being contacted with tissue in the eye.

(32) The method of any one of items 25 to 31, wherein the agent is present at about 21 nM or greater.

(33) The method of any one of items 25 to 32, further comprising administering a corneal endothelial cell separately from the agent.

(34) The method of any one of items 25 to 33, wherein the agent is provided while being mixed with a corneal endothelial cell, and at least one agent selected from the group consisting of laminins and fragments thereof is injected into an eye thereby being contacted with tissue in the eye.

(35) The method of any one of items 25 to 34, further comprising administering a ROCK inhibitor separately from the agent.

(36) The method of any one of items 25 to 35, wherein the ROCK inhibitor is selected from the group consisting of Y-27632 ((R)-(+)-trans-(4-pyridyl)-4-(1-aminoethyl)-cyclohexanecarboxamide dihydrochloride monohydrate) and a pharmaceutically acceptable salt thereof.

(37) The method of any one of items 25 to 32, wherein the agent mixed with a corneal endothelial cell is about 2.1 nM or greater, and the agent to be injected is about 21 nM or greater.

(38) Use of at least one agent selected from the group consisting of laminins and fragments thereof in the manufacture of a medicament for therapy or prophylaxis of a disease, a disorder, or a condition of a corneal endothelium.

(39) Use of item 38, further comprising the feature of one or more of items 2 to 22.

(40) Use of at least one agent selected from the group consisting of laminins and fragments thereof for therapy or prophylaxis of a disease, a disorder, or a condition of a corneal endothelium.

(41) Use of item 40, further comprising a feature described in one or more of items 2 to 22.

It is understood that one or more of the aforementioned features can further be provided as a combination in addition to the explicitly shown combinations in the present invention. Additional embodiments and advantages of the present invention are recognized by those skilled in the art who read and understand the following detailed description as needed.

Advantageous Effects of Invention

The present invention allows novel ophthalmic therapies, especially novel therapies of corneal endothelial cells (especially human corneal endothelial cells). In particular, the present invention can result in near complete recoveries from bullous keratopathy. In a preferred embodiment, the Descemet's membrane is healed. Such an effect is a significant effect that could not be achieved with conventional techniques.

BRIEF DESCRIPTION OF DRAWINGS

FIG. 3 shows staining with, from the left, anti-$Na^+/K^+$-ATPase antibodies, anti-ZO-1 antibodies, anti-N-cadherin antibodies, and phalloidin.

(+) (100 µM), and the bottom row shows a result with laminin 511-E8 fragments and Y-27632 (+) (100 µM). Phalloidin staining demonstrates that more cells adhere in an individual to which cells are injected with laminin 511-E8 fragments (2.1 nM) and Y-27632 (+) (100 µM). Right side shows a graph of cell density data. The vertical axis indicates the cell density (cells/mm$^2$). The adhered cell density was significantly higher in an individual to which cells were injected with laminin 511-E8 fragments (2.1 nM) and Y-27632 (+) (100 µM).

Figure 5:
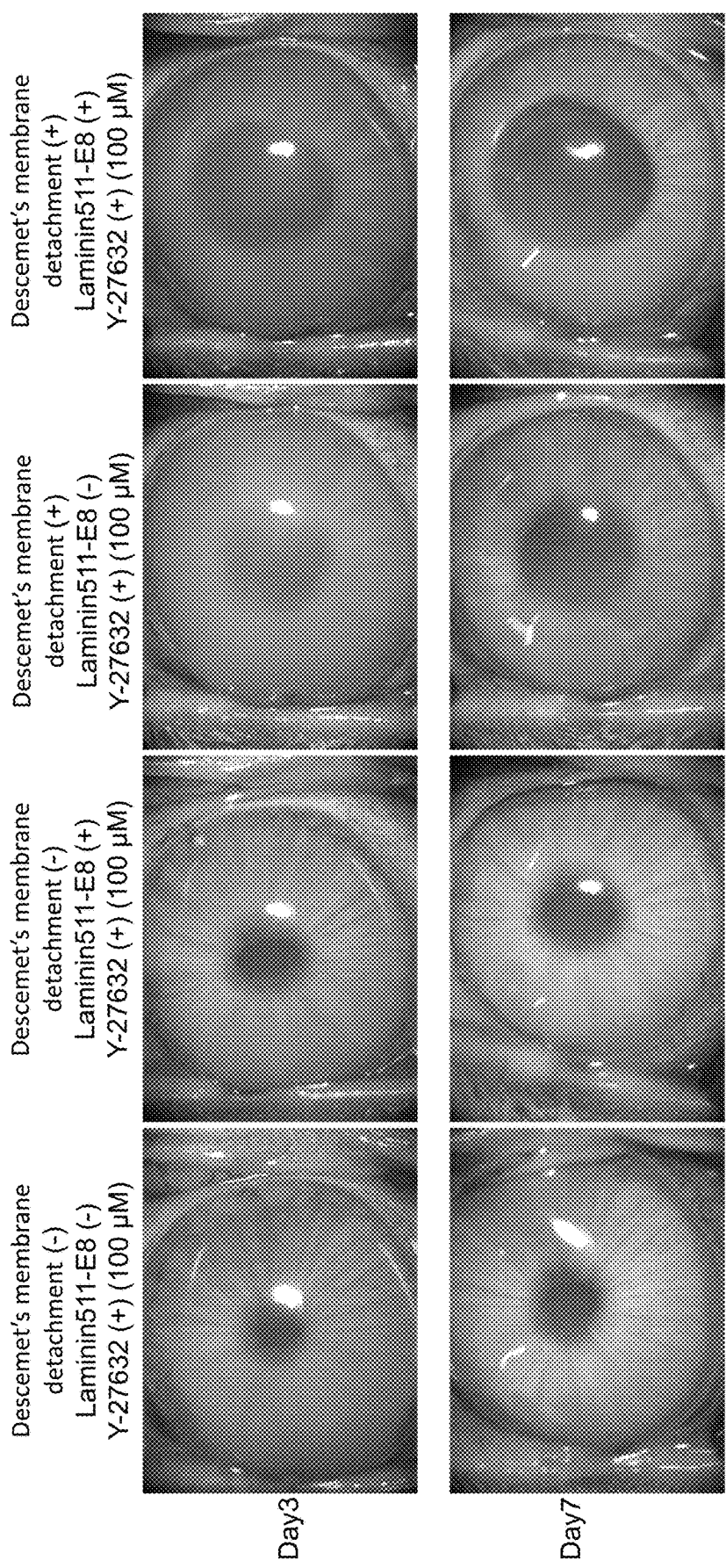

FIG. 5 shows pictures of the anterior ocular segment after cultured corneal endothelium transplantation in a rabbit bullous keratopathy model. Pictures of the anterior ocular segment are shown, from the left, for an individual which had corneal endothelial cells detached but not the Descemet's membrane and had cultured corneal endothelial cells injected with Y-27632 (+) (100 µM), an individual which had corneal endothelial cells detached but not the Descemet's membrane and had cells injected with laminin 511-E8 fragments (2.1 nM) and Y-27632 (+) (100 µM), an individual of a bullous keratopathy model which had the Descemet's membrane detached and cells injected with Y-27632 (+) (100 µM), and an individual of a bullous keratopathy model which had the Descemet's membrane detached and had cells injected with laminin 511-E8 fragments (2.1 nM) and Y-27632 (+) (100 µM). The top row shows results for Day 3 and the bottom row shows results for Day 7.

Figure 6:
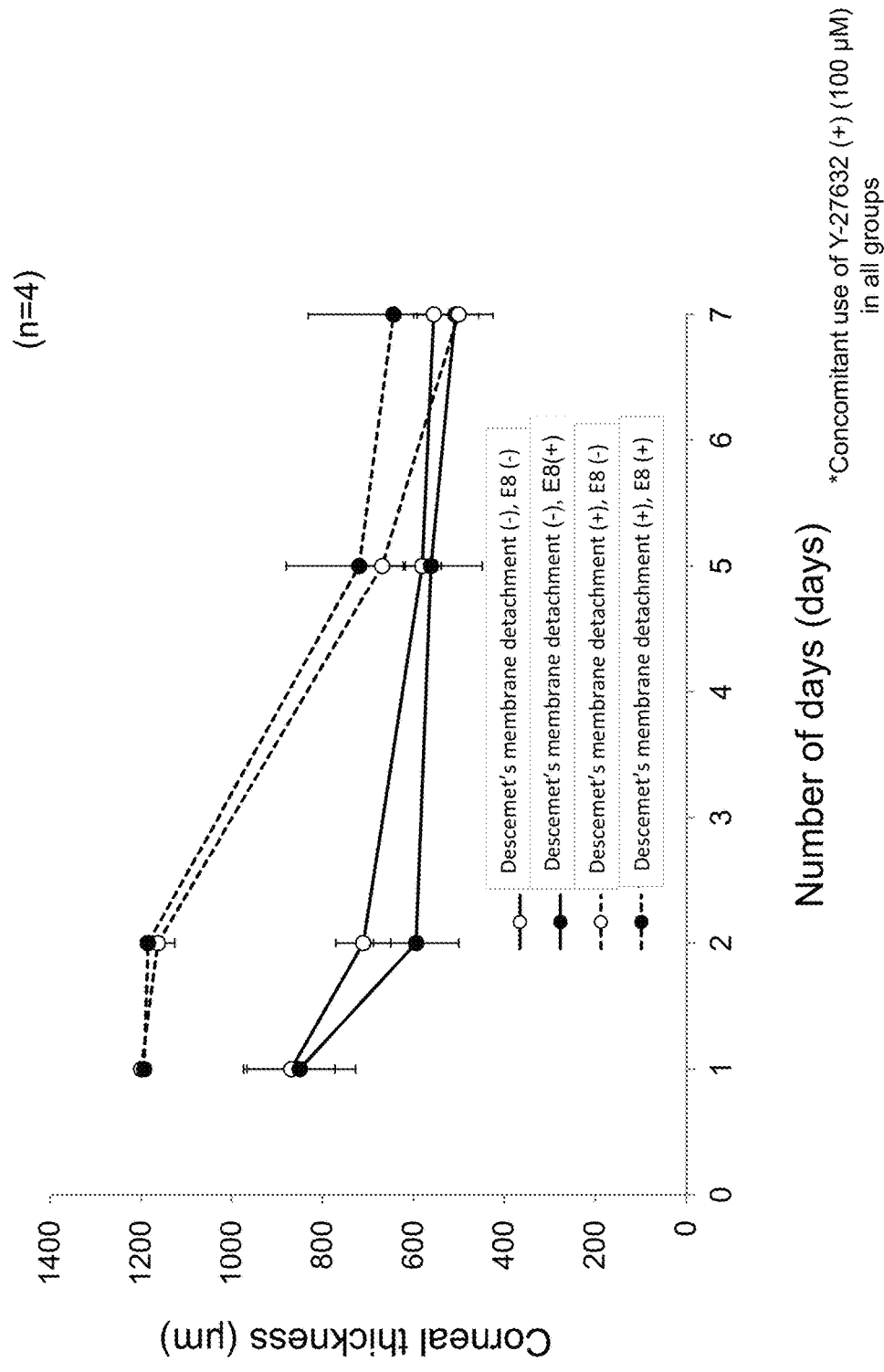

FIG. 6 shows the corneal thickness (µm) of the four groups shown in FIG. 5 after cultured corneal endothelium transplantation. The horizontal axis indicates the number of days after treatment. Solid lines indicate no Descemet's membrane detachment, and dotted lines indicate having Descemet's membrane detachment. Each filled circle indicates having laminin 511-E8 fragments, and open circles indicate no laminin 511-E8 fragment. Thinning of corneal thickness was delayed more with detachment of the Descemet's membrane relative to cases without detachment.

Figure 7:
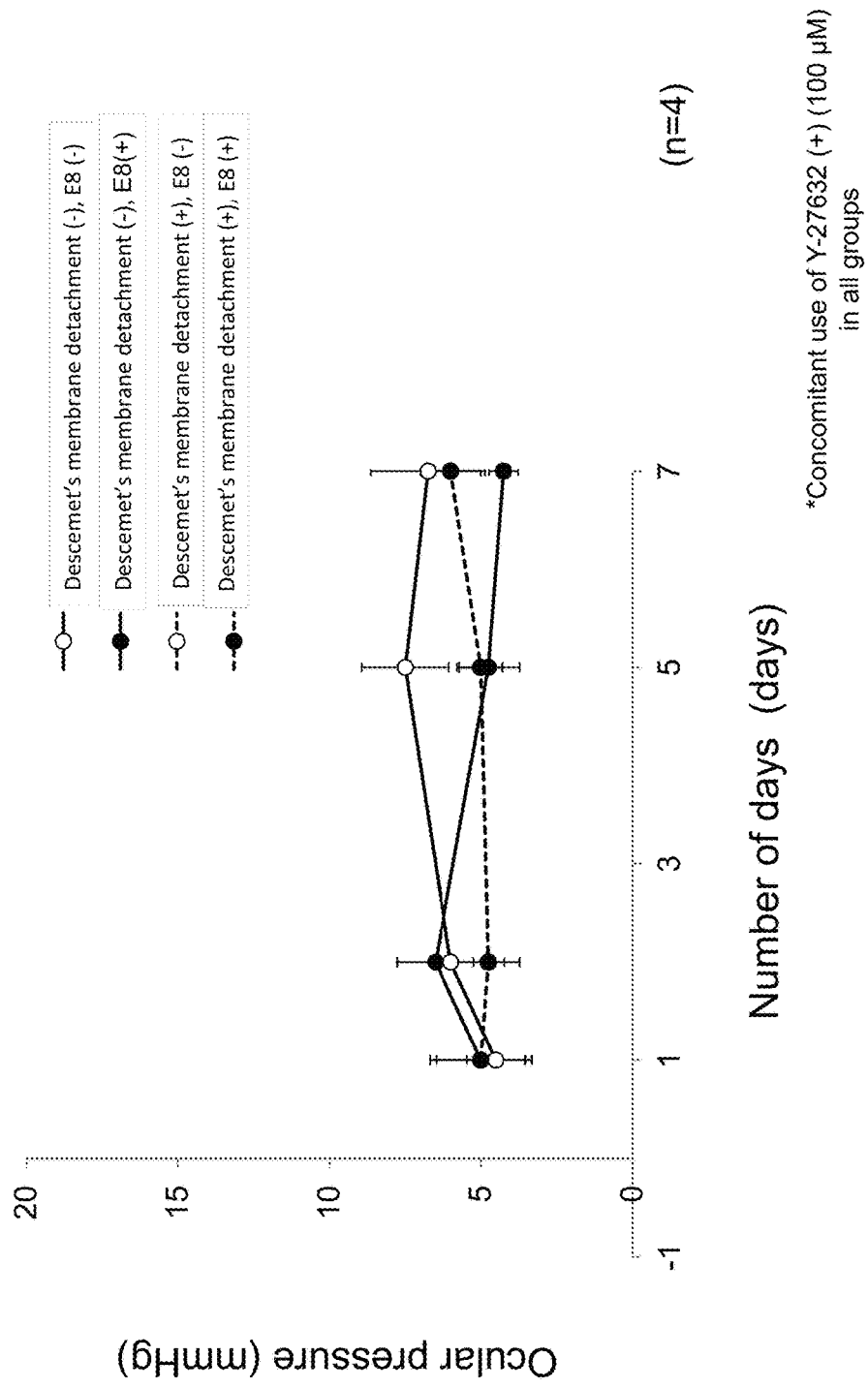

FIG. 7 shows ocular pressure (mmHg) in the four groups shown in FIG. 5 after cultured corneal endothelium transplantation. The horizontal axis indicates the number of days after treatment. Solid lines indicate no Descemet's membrane detachment, and dotted lines indicate having Descemet's membrane detachment. Each filled circle indicates having laminin 511-E8 fragments, and open circles indicate no laminin 511-E8 fragment. Elevation in ocular pressure, which is considered a complication due to cell transplantation, was not observed in any group.

Figure 8:
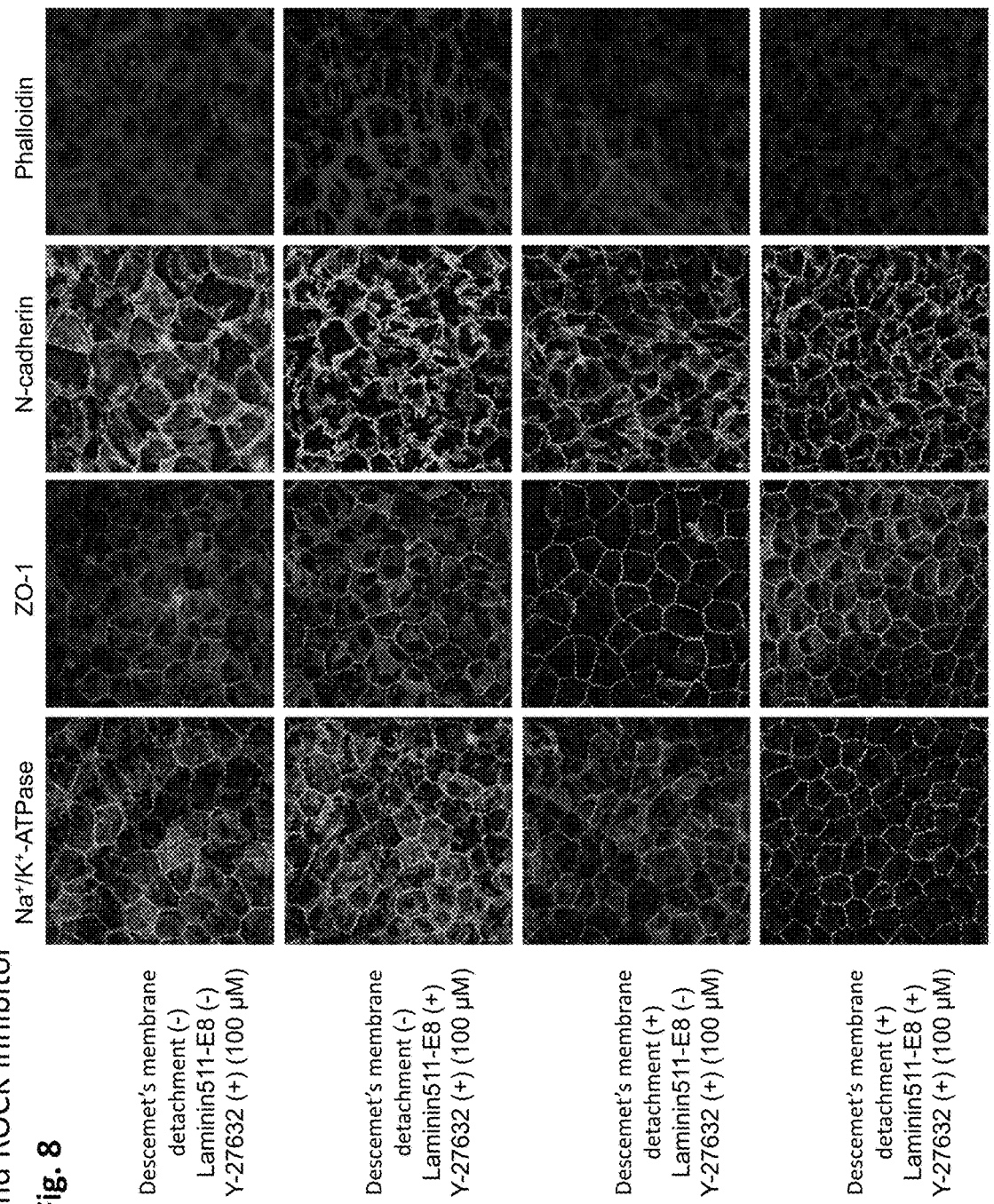

FIG. 8 shows histological examination of the four groups shown in FIG. 6 14 days after cultured corneal endothelium transplantation. FIG. 8 shows staining with, from the left, anti-Na$^+$/K$^+$-ATPase antibodies, anti-ZO-1 antibodies, anti-N-cadherin antibodies, and phalloidin. FIG. 8 shows images of staining, from the top row, for individuals which had corneal endothelial cells detached but not the Descemet's membrane and had cultured corneal endothelial cells injected with Y-27632 (+) (100 µM), individuals which had corneal endothelial cells detached but not the Descemet's membrane and had cells injected with laminin 511-E8 fragments (2.1 nM) and Y-27632 (+) (100 µM), individuals of a bullous keratopathy model which had the Descemet's membrane detached and had cells injected with Y-27632 (+) (100 µM), and individuals of a bullous keratopathy model which had the Descemet's membrane detached and had cells injected with laminin 511-E8 fragments (2.1 nM) and Y-27632 (+) (100 µM).

Figure 9:
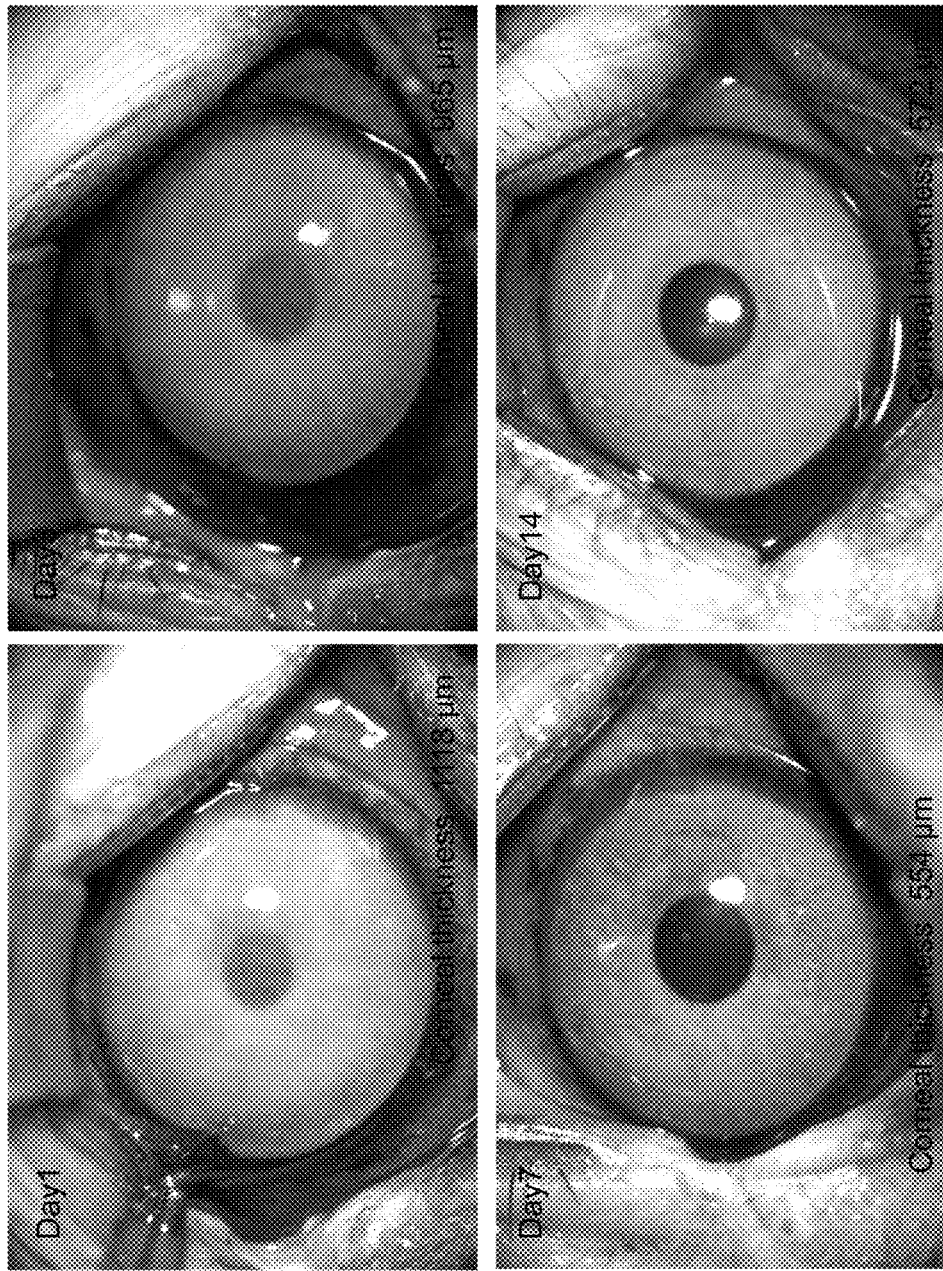

FIG. 9 shows pictures of the anterior ocular segment after cultured corneal endothelium transplantation in a monkey bullous keratopathy model subjected to concomitant use of laminin 511-E8 fragments. A cynomolgus monkey model with corneal endothelial cells mechanically scraped off was injected with cultured cynomolgus monkey corneal endothelial cells into the anterior chamber and was maintained in a face-down posture for three hours. The top left picture shows the result on Day 1, top right picture shows the result on Day 3, bottom left picture shows the result on Day 7, and the bottom right shows the result on Day 14.

Figure 10:
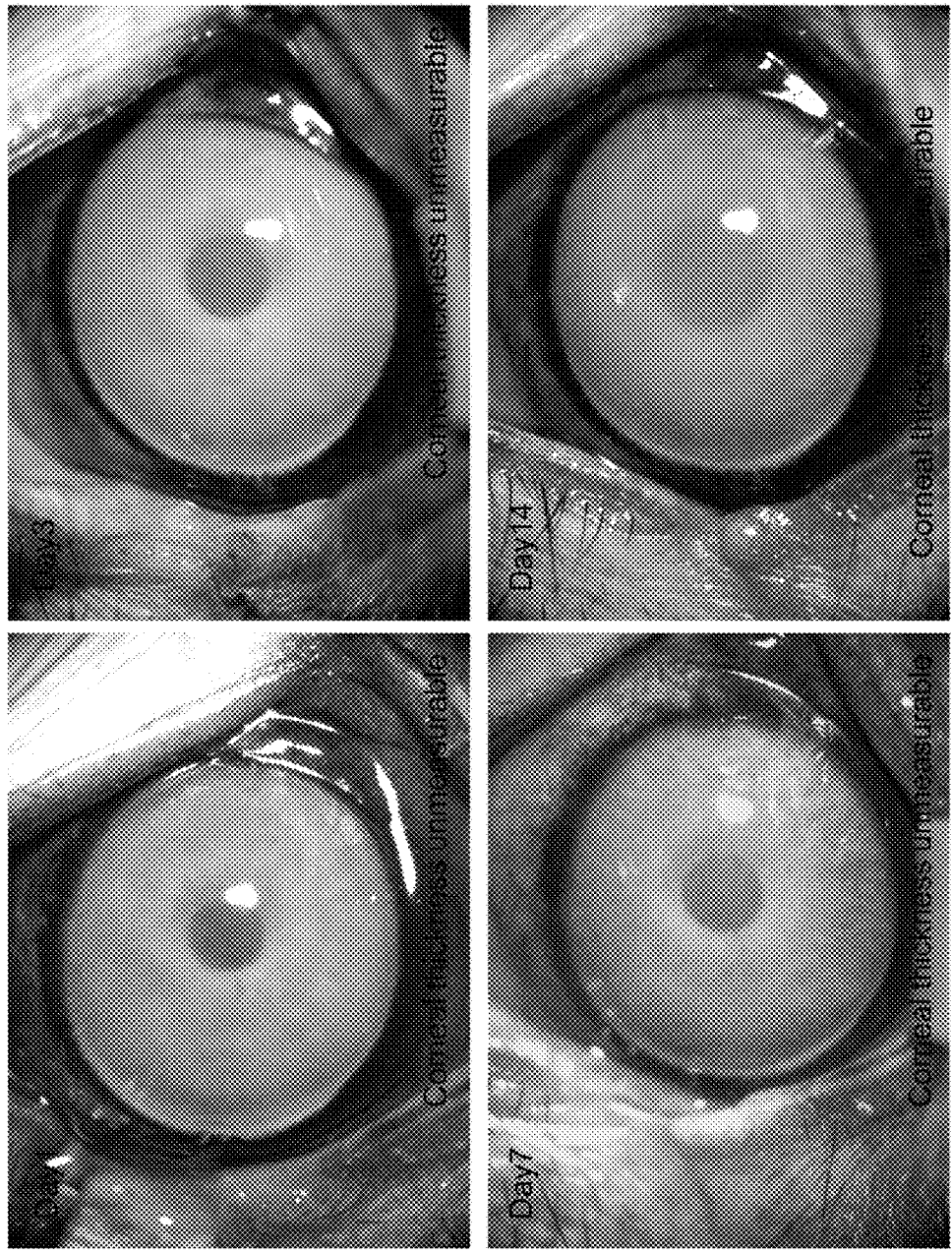

FIG. 10 shows pictures of the anterior ocular segment after detaching the Descemet's membrane and transplanting cultured corneal endothelial cells concomitantly with laminin 511-E8 fragments in a monkey bullous keratopathy model. A cynomolgus monkey model with corneal endothelial cells mechanically scraped off was injected, after detachment of the Descemet's membrane, with cultured cynomolgus monkey corneal endothelial cells into the anterior chamber and was maintained in a face-down posture for three hours. The top left picture shows the result on Day 1, top right picture shows the result on Day 3, bottom left picture shows the result on Day 7, and the bottom right shows the result on Day 14.

Figure 11:
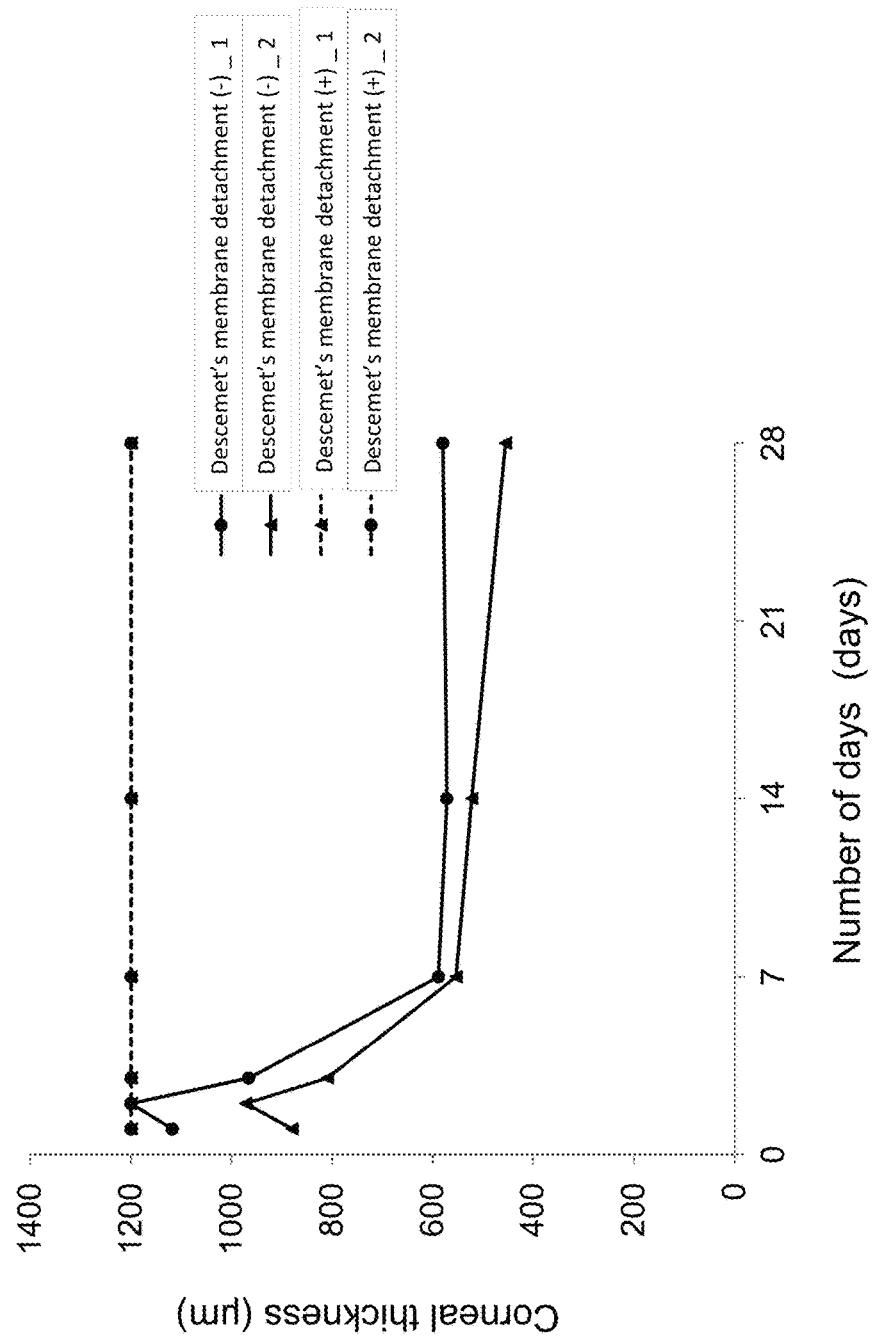

FIG. 11 shows the corneal thickness after cultured corneal endothelium transplantation in a monkey bullous keratopathy model with concomitant use of laminin 511-E8 fragments. The corneal thickness (µm) of individuals with and without Descemet's membrane detachment is shown. The horizontal axis indicates the number of days after treatment, and the vertical axis indicates the corneal thickness (µm). Solid lines indicate an example without detachment of the Descemet's membrane, and the dotted lines indicate individuals with Descemet's membrane detachment. Filled circles and triangles indicate individual differences. Thinning of corneal thickness was not observed in both examples with Descemet's membrane detachment.

Figure 12:
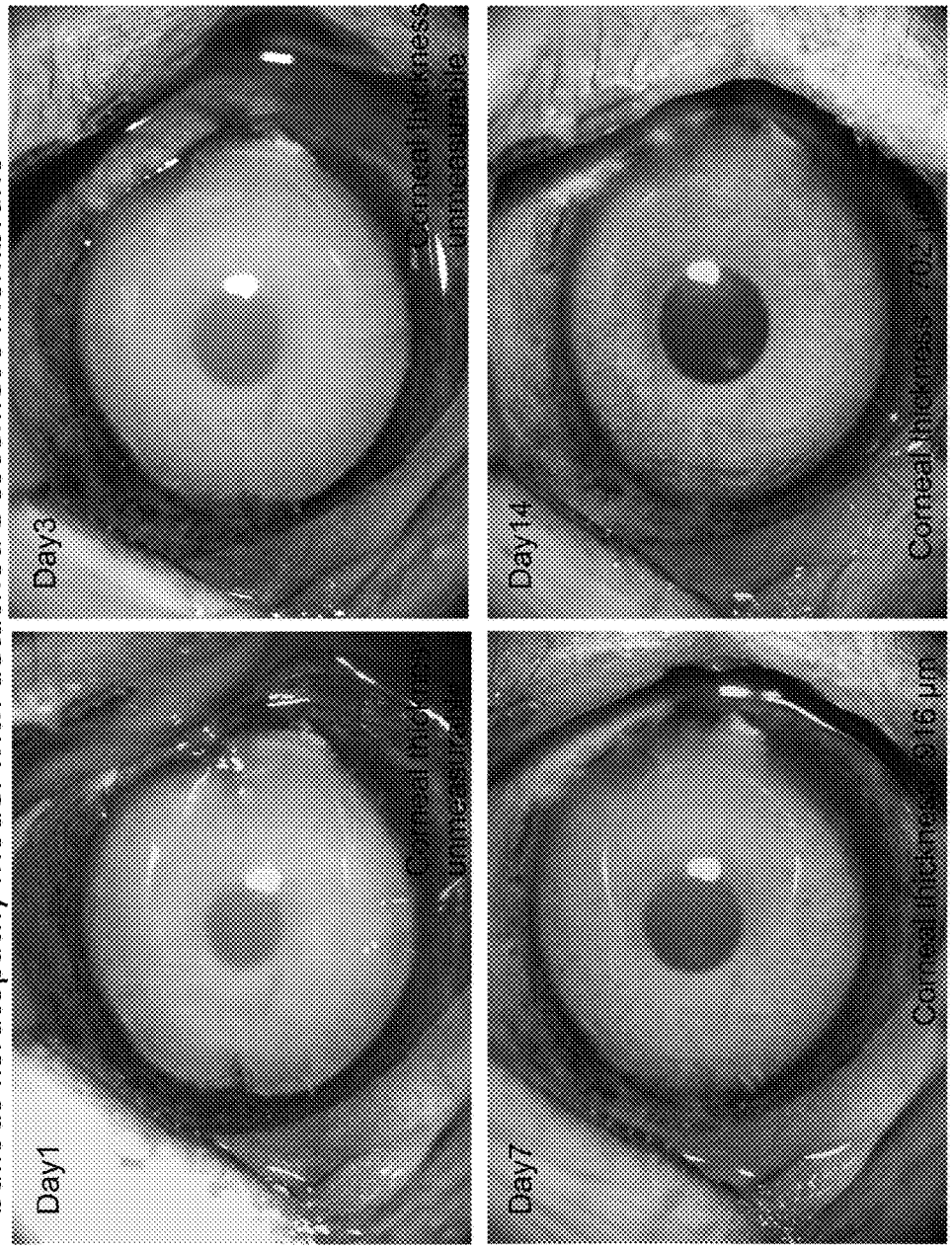

FIG. 12 shows pictures of the anterior ocular segment after detaching the Descemet's membrane in a monkey bullous keratopathy model, injecting laminin 511-E8 fragments into the anterior chamber at a concentration of 21 nM, and leaving the model standing for one hour to coat the corneal stroma exposed by the detachment of the Descemet's membrane in the living body, then transplanting cultured corneal endothelial cells concomitantly with laminin 511-E8 fragments. The top left picture shows the result on Day 1, top right picture shows the result on Day 3, bottom left picture shows the result on Day 7, and the bottom right shows the result on Day 14.

Figure 13:
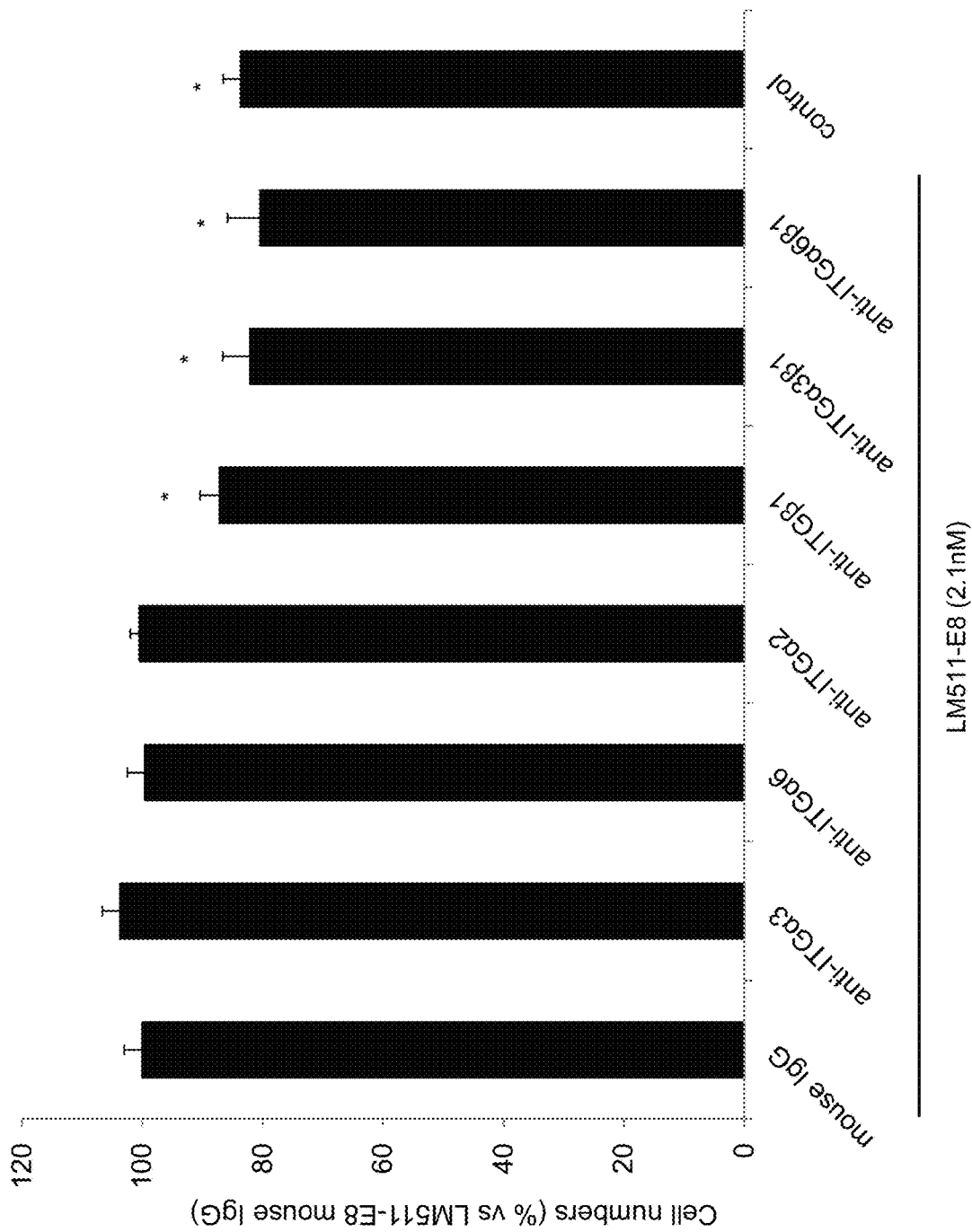

FIG. 13 shows the effect of integrins on adhesion of corneal endothelial cells. Laminin 511-E8 fragments were added so that the final concentration was 2.1 nM, and the corneal endothelial cells were seeded. The number of adhering cells after 24 hours is shown (proportion to mouse IgG is shown) when seeding after adding, from the left, in order, mouse IgG, anti-integrin $\alpha_3$ antibody, anti-integrin $\alpha_6$ antibody, anti-integrin $\alpha_2$ antibody, anti-integrin $\beta_1$ antibody, anti-integrin $\alpha_3\beta_1$ antibody, and anti-integrin $\alpha_6\beta_1$ antibody. The right end shows the control to which only mouse IgG was added for seeding without adding a laminin 511-E8 fragment.

FIG. 14 shows that activation of cell adhesion associated proteins is mediated by an integrin. A laminin 511-E8 fragment-free group was prepared as a control on the left end. Groups to which laminin 511-E8 fragments were added so that the final concentration was 2.1 nM were prepared in the second column from the left and thereafter. The results of Western blot are shown in the second column from the left and thereafter for cases adding, in order, mouse IgG, anti-integrin $\alpha_3$ antibody, anti-integrin $\alpha_6$ antibody, anti-integrin $\alpha_2$ antibody, anti-integrin $\beta_1$ antibody, anti-integrin $\alpha_3\beta_1$ antibody, and anti-integrin $\alpha_6\beta_1$ antibody for seeding. From the top row, p-FAK, FAK, p-Paxillin, and background GAPDH are shown. The numerical values in each band indicate the relative value of quantified band intensity while assuming the no laminin 511-E8 on the left end as 1.

DESCRIPTION OF EMBODIMENTS

The present invention is described hereinafter. Throughout the entire specification, a singular expression should be understood as encompassing the concept thereof in the plural form unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

Definitions

As used herein, "corneal endothelial cell" is used in the meaning that is commonly used in the art. A cornea is one of the lamellar tissues constituting an eye. A cornea is transparent and is positioned at a part closest to the external environment. In humans, it is understood that a cornea is composed of five layers, i.e., corneal epithelium, Bowman's membrane, Lamina propria, Descemet's membrane (corneal endothelial basement membrane), and corneal endothelium, in order from the outside (body surface). Unless specifically noted otherwise, parts other than the epithelium and endothelium may be collectively called "corneal stroma", which are also called as such herein. As used herein "HCEC" (human corneal endothelial cell) is an abbreviation of human corneal endothelial cells. A rabbit corneal endothelial cell is abbreviated as "RCEC", and a monkey corneal endothelial cell is abbreviated as "MCEC". It is understood that naturally-occurring cells as well as cells differentiated from stem cells such as differentiated cells induced from iPS or the like can be used as the corneal endothelial cells used in the present invention.

As used herein, "isolated" refers to a state where a substance that naturally accompanies an entity under normal circumstances is at least reduced, and preferably a state where the entity is substantially free of such a substance. Thus, isolated cells, tissue and the like refer to cells, tissue and the like that are substantially free of other substances which accompany them (e.g., other cells, proteins, nucleic acids or the like) in a natural environment.

<Laminin>

As used herein, "laminin" is a constituent protein of a basement membrane of an extracellular matrix. Laminins promote multicellularity/tissue construct and maintenance thereof, cell adhesion, cell migration, and cell growth and have a close relationship with cancer cells. A laminin is considered to be expressed at the early stage (two-cell stage) of blastogenesis. A laminin is a heterotrimer consisting of one of each of an $\alpha$ chain, a $\beta$ chain and a $\gamma$ chain. For the naming of laminins, the nomenclature in the order of discovery (laminin-1, laminin-2, etc.) is known. However, correspondence to subunits is not considered, so that a newer naming method, in which the name of the subclass $\alpha$, $\beta$, or $\gamma$ (a three digit number, the digit of one hundred indicates $\alpha$, the digit of ten indicates $\beta$, and the digit of one indicates $\gamma$) is described together, is employed herein. In case of $\alpha1$, $\beta1$, and $\gamma1$, such a laminin is called laminin 111. For laminins, five types of $\alpha$ chains, 3 types of $\beta$ chains, and three types of $\gamma$ chains have been discovered. Thus, the theoretic maximum number of combinations is 5×3×3=45, so that 45 types of laminin molecules are possible. However, it is believed that not all of the combinations exist in nature. Each subunit, for instance, is called LAMA1, LAMA2, LAMA3, LAMA4, or LAMA5 for an $\alpha$ chain, LAMB1, LAMB2, or LAMB3 for a $\beta$ chain, and LAMC1, LAMC2, or LAMC3 for a $\gamma$ chain. Laminin proteins used in the present invention may be naturally-occurring laminin proteins or those with a modified form where one or more amino acid residues are modified while retaining the biological activity thereof, especially the cell adhesion promoting activity. Further, the laminin proteins in the present invention are not limited in terms of the origin, production method thereof or the like, as long as the laminin protein has the features described herein. Thus, the laminin proteins used in the present invention may be any of naturally occurring proteins, proteins expressed from a recombinant DNA by a genetic engineering approach, or chemically synthesized proteins. The origin of the laminin proteins used in the present invention is not particularly limited, but is preferably derived from a human. When culturing a human cell for the purpose of obtaining a medical material, it is preferable, but is not limited to, using a laminin derived from a human in order to avoid the use of a material derived from another animal.

Binding molecules of a laminin are known. $\alpha1\beta1$, $\alpha2\beta1$, $\alpha2\beta2$, $\alpha3\beta1$, $\alpha6\beta1$, $\alpha6\beta4$, $\alpha7\beta1$, $\alpha9\beta1$, $\alpha v\beta3$, $\beta v\beta5$, and $\alpha v\beta8$ are integrins known as a laminin receptor.

The following Table describes representative laminins and the explanation thereof.

TABLE 1

| Trimer composition (name) | Main expression site | Integrin binding specificity |
|---|---|---|
| $\alpha1\beta1\gamma1$ (laminin-1) | Fetal tissue | $\alpha6\beta1$ |
| $\alpha1\beta2\gamma1$ (laminin-3) | | |
| $\alpha2\beta1\gamma1$ (laminin-2) | Muscles, nerves | $\alpha7\beta1$, $\alpha6\beta1$, $\alpha3\beta1$ |
| $\alpha2\beta2\gamma1$ (laminin-4) | (Schwann cell) | |
| $\alpha2\beta1\gamma3$ (laminin-12) | | |
| $\alpha3\beta3\gamma2$ (laminin-5) | Skin, lung, and other epithelial tissue | $\alpha3\beta1$, $\alpha6\beta4$ |
| $\alpha3\beta1\gamma1$ (laminin-6) | | |
| $\alpha3\beta2\gamma1$ (laminin-7) | | |
| $\alpha4\beta1\gamma1$ (laminin-8) | Blood vessel | $\alpha6\beta1$, $\alpha3\beta1$ |
| $\alpha4\beta2\gamma1$ (laminin-9) | | |
| $\alpha5\beta1\gamma1$ (laminin-10) | Blood vessel, liver, lung, and other epithelial tissue | $\alpha3\beta1$, $\alpha6\beta1$ |
| $\alpha5\beta2\gamma1$ (laminin-11) | | |

As used herein, "$\alpha1$ chain" (LAMA1) is a subunit of a laminin.protein of a cell adhesion molecule in an extracellular matrix, and is called LAMA1, LAMA, S-LAM-alpha, or the like. For human LAMA1, the sequences of the gene and protein are registered as NCBI registration numbers NM_005559 and NP_005550, respectively. OMIM is identified with an accession number 150320. When used for the purpose herein, it is understood that "$\alpha1$ chain" or "LAMA1" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "α2 chain" (LAMA2) is a subunit of a laminin.protein of a cell adhesion molecule in an extracellular matrix, and is called LAMA2, LAMM, or the like. For human LAMA2, the sequences of the gene and protein are registered as NCBI registration numbers NM_000426 and NP_000417, respectively. OMIM is identified with an accession number 156225. When used for the purpose herein, it is understood that "α2 chain" or "LAMA2" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "α3 chain" (LAMA3) is a subunit of a laminin protein of a cell adhesion molecule in an extracellular matrix, and is called LAMA3, BM600, E170, LAMNA, LOCS, lama3a, or the like. For human LAMA3, the sequences of the gene and protein are registered as NCBI registration numbers NM_000227 and NP 000218, respectively. OMIM is identified with an accession number 600805. When used for the purpose herein, it is understood that "α3 chain" or "LAMA3" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "α4 chain" (LAMA4) is a subunit of a laminin protein of a cell adhesion molecule in an extracellular matrix, and is called LAMA4, LAMA3, LAMA4*-1, CMDIJJ or the like. For human LAMA4, the sequences of the gene and protein are registered as NCBI registration numbers NM_001105206 and NP 001098676, respectively. OMIM is identified with an accession number 600133. When used for the purpose herein, it is understood that "α4 chain" or "LAMA4" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid encoding the protein under a high or low stringency condition.

As used herein, "α5 chain" (LAMA5) is a subunit of a laminin protein of a cell adhesion molecule in an extracellular matrix, and is called LAMA5, KIAA1907, or the like. For human LAMA5, the sequences of the gene and protein are registered as NCBI registration numbers NM_005560 and NP_005551, respectively. OMIM is identified with an accession number 601033. When used for the purpose herein, it is understood that "α5 chain" or "LAMA5" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "β1 chain" (LAMB1) is a subunit of a laminin protein of a cell adhesion molecule in an extracellular matrix, and is called LAMB1, CLM, LIS5, or the like. For human LAMB1, the sequences of the gene and protein are registered as NCBI registration numbers NM_002291 and NP_002282, respectively. OMIM is identified with an accession number 150240. When used for the purpose herein, it is understood that "β1 chain" or "LAMB1" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "β2 chain" (LAMB2) (laminin S) is a subunit of a laminin.protein of a cell adhesion molecule in an extracellular matrix, and is called LAMB2, LAMS, NPHS5, or the like. For human LAMB2, the sequences of the gene and protein are registered as NCBI registration numbers NM_002292 and NP_002283, respectively. OMIM is identified with an accession number 150325. When used for the purpose herein, it is understood that "β2 chain" or "LAMB2" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "β3 chain" (LAMB3) is a subunit of a laminin protein of a cell adhesion molecule in an extracellular matrix, and is called LAMB3, BM600-125KDA, LAM5, LAMNB1, or the like. For human LAMB3, the sequences of the gene and protein are registered as NCBI registration numbers NM_000228 and NP_000219, respectively. OMIM is identified with an accession number 150310. When used for the purpose herein, it is understood that "β3 chain" or "LAMB3" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "γ1 chain" (LAMC1) is a subunit of a laminin protein of a cell adhesion molecule in an extracellular matrix, and is called LAMC1, LAMB2, or the like. For human LAMC1, the sequences of the gene and protein are registered as NCBI registration numbers NM_002293 and NP_002284, respectively. OMIM is identified with an accession number 150290. When used for the purpose herein, it is understood that "γ1 chain" or "LAMC1" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "γ2 chain" (LAMC2) is a subunit of a laminin protein of a cell adhesion molecule in an extracellular matrix, and is called LAMC2, B2T, BM600, CSF, EBR2, EBR2A, LAMB2T, LAMNB2, or the like. For human LAMC2, the sequences of the gene and protein are registered as NCBI registration numbers NM 005562 and NP 005553, respectively. OMIM is identified with an accession number 150292. When used for the purpose herein, it is understood that "γ² chain" or "LAMC2" means not only a protein having an amino acid sequence set forth in a specific sequence number or accession (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "γ3 chain" (LAMC3) is a subunit of a laminin protein of a cell adhesion molecule in an extracellular matrix, and is called LAMC3, OCCM, or the like. For human LAMC3, the sequences of the gene and protein are registered as NCBI registration numbers NM_006059 and NP_006050, respectively. OMIM is identified with an accession number 604349. When used for the purpose herein, it is understood that "γ3 chain" or "LAMC3" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

Figure 2:
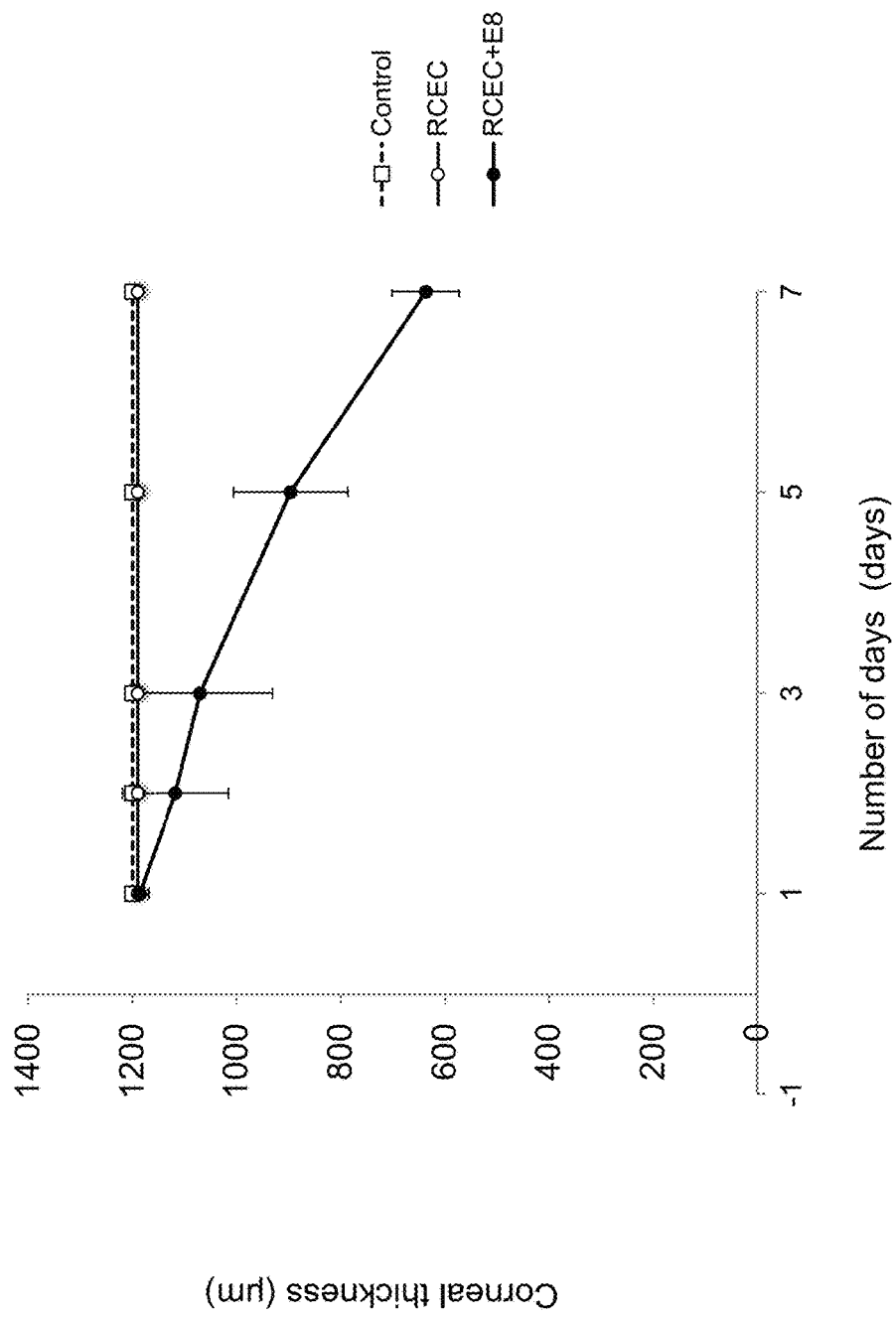
FIG. 2 shows the change in corneal thickness after cultured cornea transplantation in a rabbit bullous keratopathy model using laminin 511-E8 fragments. The vertical axis indicates the corneal thickness (μm) measured by an ultrasound pachymeter. The horizontal axis indicates the number of days after treatment. The bar indicates the standard error.

As used herein, "laminin expressed in corneal endothelial cells" refers to a type of laminin with a gene which is expressed in a normal state, or preferably significantly expressed at the protein level, in corneal endothelial cells. α5, β1, β2, and γ1 are confirmed as being expressed by the analysis herein (FIG. 2 in WO 2015/080297). Thus, at least laminin 511 and laminin 521 are confirmed as being expressed. Dev. Dyn. 218, 213-234, 2000, and J. Biol. Chem. 277 (15), 12741-12748, 2002 have detailed description of laminin 511. Thus, the content disclosed in these documents is incorporated herein by reference. For laminin 511 and the like, it is possible to utilize those that are commercially available. For example, recombinant proteins of laminin 511 and laminin 521 are commercially available and obtainable from BioLamina AB.

As used herein, "expression" of a gene, polynucleotide, polypeptide or the like refers to the gene or the like being subjected to a certain effect in vivo to be in another form. Preferably, the expression refers to a gene, polynucleotide or the like being transcribed and translated to be in a form of a polypeptide, but transcription resulting in mRNA can also be one form of expression. More preferably, such a polypeptide form can be those subjected to post-translation processing (referred to as a derivative herein). For example, the expression level of each laminin chain can be determined by any method. Specifically, the expression level of each laminin chain can be found by evaluating the amount of mRNA of each laminin chain, amount of protein of each laminin chain, or biological activity of the protein of each laminin chain. The amount of mRNA or protein of each laminin chain can be determined by a method as described herein.

As used herein, "functional equivalent" refers to anything that has the same function of interest but a different structure with respect to the original entity. Thus, it is understood that "a laminin or each laminin chain, or a functional equivalent thereof" or a "group consisting of a laminin, each laminin chain, and a functional equivalent thereof" encompasses a laminin or each laminin chain itself, as well as fragments, mutants, or variants of the laminin or each laminin chain (e.g., amino acid sequence variant or the like) having one or more of cell adhesion capability, differentiation controlling and/or growth promoting action on an eye cell or the like, and substances that can change into a laminin or each laminin chain itself, or a fragment, mutant, or variant of the laminin or each laminin chain at the time of action (including, for example, nucleic acids encoding a laminin or each laminin chain itself or a fragment, mutant, or variant of the laminin or each laminin chain, vectors and cells comprising such a nucleic acid, and the like). Typical examples of "a laminin or each laminin chain, or a functional equivalent thereof" or a "group consisting of a laminin, each laminin chain, and a functional equivalent thereof" include at least one agent selected from the group consisting of laminins and fragments thereof. In the present invention, it is understood that a functional equivalent of a laminin or each laminin chain can be used in the same manner as the laminin or each laminin chain without any specific mention thereof.

As used herein, "fragment" refers to a polypeptide or a polynucleotide with a sequence length of 1 to n−1 with respect to the full length polypeptide or polynucleotide (with length n). The length of a fragment can be appropriately changed in accordance with the objective. For a polypeptide, examples of the lower limit of the length thereof include 3, 4, 5, 6, 7, 8, 9, 10, 15, 20, 25, 30, 40, 50 and more amino acids. Lengths represented by an integer that is not specifically listed herein (e.g. 11 and the like) can also be appropriate as the lower limit. For a polynucleotide, examples of the lower limit of the length thereof include 5, 6, 7, 8, 9, 10, 15, 20, 25, 30, 40, 50, 75, 100 and more nucleotides. Lengths represented by an integer that is not specifically listed herein (e.g. 11 and the like) can also be appropriate as the lower limit. It is understood herein that fragments themselves of such a laminin chain, when functioning as a factor of activity thereof, e.g., growth promotion or maintenance, are within the scope of the present invention. According to the present invention, the term "activity" as used herein refers to a function of a molecule in the broadest meaning. Activity generally encompasses, but is not intended to be limited to, biological function, biochemical function, physical function, and chemical function of a molecule. Examples of activity include enzymatic activity, ability to interact with another molecule, ability to activate, promote, stabilize, inhibit, suppress, or destabilize a function of another molecule, stability, and ability to localize at a specific position in a cell. When applicable, the term is also directed to a function of a protein complex in the broadest sense. As used herein, "biological function", with regard to a gene or a nucleic acid or polypeptide related thereto, refers to a specific function that the gene, nucleic acid or polypeptide can have in a living body. Examples thereof include, but are not limited to, production of a specific antibody, enzymatic activity, impartation of resistance and the like. As used herein, biological function can be exerted by "biological activity". As used herein, "biological activity" refers to activity that a certain agent (e.g., polynucleotide, protein, or the like) can have in a living body, including activity exerting a variety of functions (e.g., transcription promoting activity) such as the activity of activating or deactivating a molecule from interaction with another molecule. When two agents interact, the biological activity thereof can be thought of as the bond between the two molecules and the biological change resulting therefrom, e.g., the two molecules are bound when precipitation of one of the molecules with an antibody results in co-precipitation of the other molecule. Thus, one method of determination includes observing such co-precipitation. When an agent is for instance an enzyme, the biological activity thereof encompasses the enzymatic activity thereof. Another example includes binding of a ligand to a corresponding receptor when an agent is a ligand. Such biological activity can be measured by a well-known technique in the art. Thus, "activity" refers to various measurable indicators that indicate or reveal the bond (either directly or indirectly) or affects a response (i.e., having a measurable effect in response to some exposure or stimulation). Examples thereof include the affinity of a compound that directly binds to the polypeptide or polynucleotide of the present invention, the amount of proteins upstream or downstream after some exposure or stimulation, and a dimension of another similar function.

"Functionally active" as used herein refers to a polypeptide, a fragment, or a derivative having a structural function, controlling function, or biochemical function of a protein such as biological activity in accordance with the embodiment associated with the polypeptide, fragment or derivative of the invention.

As used herein, a "fragment" of a laminin refers to any fragment of a laminin. As an agent used in the present invention, it is understood that not only the full length laminin, but also a fragment of the laminin can be used, as long as the fragment has the function of the full length laminin, particularly the cell adhesion capability of an endothelial cell. Thus, a fragment of a laminin used in the present invention generally has at least one function of the laminin. Such a function can encompass cell adhesion capability of an endothelial cell in particular.

The sequence of a laminin found to be expressed in corneal endothelial cells in the present invention will be explained. It is understood that these laminins are preferred representative examples of the present invention and the present invention is not limited to these specific laminin subtypes.

A typical nucleotide sequence of a laminin α5 chain can be:
(a) a polynucleotide having the base sequence set forth in SEQ ID NO: 1 or a fragment sequence thereof;
(b) a polynucleotide encoding a polypeptide consisting of the amino acid sequence set forth in SEQ ID NO: 2 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 2, wherein the variant polypeptide has biological activity;
(d) a polynucleotide which is an allele or a splice mutant of the base sequence set forth in SEQ ID NO: 1 or a fragment thereof;
(e) a polynucleotide encoding a species homolog of a polypeptide consisting of the amino acid sequence set forth in SEQ ID NO: 2 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to activity of a laminin α5 chain. Doi M et al., J. Biol. Chem. 277(15), 12741-12748, 2002 and U.S. Pat. No. 6,933,273 can be referenced with regard to α5 chains.

An amino acid sequence of a laminin α5 chain can be:
(a) a polypeptide consisting of the amino acid sequence set forth in SEQ ID NO: 2 or a fragment thereof;
(b) a polypeptide having biological activity and one or more amino acids with a mutation selected from the group consisting of a substitution, an addition and a deletion in the amino acid sequence set forth in SEQ ID NO: 2;
(c) a polypeptide encoded by an allele or a splice mutant of the base sequence set forth in SEQ ID NO: 1;
(d) a polypeptide which is a species homolog of the amino acid sequence set forth in SEQ ID NO: 2; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to the activity of a laminin α5 chain. Doi M et al., J. Biol. Chem. 277(15), 12741-12748, 2002 and U.S. Pat. No. 6,933,273 can be referenced with regard to α5 chains.

A typical nucleotide sequence of a laminin β1 chain can be:
(a) a polynucleotide having the base sequence set forth in SEQ ID NO: 3 or a fragment sequence thereof;
(b) a polynucleotide encoding a polypeptide consisting of the amino acid sequence set forth in SEQ ID NO: 4 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 4, wherein the variant polypeptide has biological activity;
(d) a polynucleotide which is an allele or a splice mutant of the base sequence set forth in SEQ ID NO: 3 or a fragment thereof;
(e) a polynucleotide encoding a species homolog of a polypeptide consisting of the amino acid sequence set forth in SEQ ID NO: 4 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to activity of a laminin β1 chain. Pillarainen et al., J. Biol. Chem. 262 (22), 10454-10462, 1987 and U.S. Pat. No. 6,933,273 can be referenced with regard to β1 chains.

An amino acid sequence of a laminin β1 chain can be:
(a) a polypeptide consisting of the amino acid sequence set forth in SEQ ID NO: 4 or a fragment thereof;
(b) a polypeptide having biological activity and one or more amino acids with a mutation selected from the group consisting of a substitution, an addition, and a deletion in the amino acid sequence set forth in SEQ ID NO: 4;
(c) a polypeptide encoded by an allele or a splice mutant of the base sequence set forth in SEQ ID NO: 3;
(d) a polypeptide which is a species homolog of the amino acid sequence set forth in SEQ ID NO: 4; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to activity of a laminin pi chain. Pillarainen et al., J. Biol. Chem. 262 (22), 10454-10462, 1987 and U.S. Pat. No. 6,933,273 can be referenced with regard to β1 chains.

A typical nucleotide sequence of a laminin β2 chain can be:
(a) a polynucleotide having the base sequence set forth in SEQ ID NO: 5 or a fragment sequence thereof;
(b) a polynucleotide encoding a polypeptide consisting of the amino acid sequence set forth in SEQ ID NO: 6 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 6, wherein the variant polypeptide has biological activity;
(d) a polynucleotide which is an allele or a splice mutant of the base sequence set forth in SEQ ID NO: 5 or a fragment thereof;
(e) a polynucleotide encoding a species homolog of a polypeptide consisting of the amino acid sequence set forth in SEQ ID NO: 6 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to the activity of a laminin β2 chain. Wewer U M et al., Genomics. Nov. 15, 1994; 24(2): 243-52., 1987 and U.S. Pat. No. 6,933,273 can be referenced with regard to β2 chains.

An amino acid sequence of a laminin 12 chain can be:
(a) a polypeptide consisting of the amino acid sequence set forth in SEQ ID NO: 6 or a fragment thereof;
(b) a polypeptide having biological activity and one or more amino acids with a mutation selected from the group consisting of a substitution, an addition, and a deletion in the amino acid sequence set forth in SEQ ID NO: 6;
(c) a polypeptide encoded by an allele or a splice mutant of the base sequence set forth in SEQ ID NO: 5;
(d) a polypeptide which is a species homolog of the amino acid sequence set forth in SEQ ID NO: 6; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to the activity of a laminin β2 chain. Wewer U M et al., Genomics. Nov. 15, 1994; 24(2): 243-52., 1987 and U.S. Pat. No. 6,933,273 can be referenced with regard to β2 chains.

A typical nucleotide sequence of a laminin γ1 chain can be:
(a) a polynucleotide having the base sequence set forth in SEQ ID NO: 7 or a fragment sequence thereof;
(b) a polynucleotide encoding a polypeptide consisting of the amino acid sequence set forth in SEQ ID NO: 8 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 8, wherein the variant polypeptide has biological activity;
(d) a polynucleotide which is an allele or a splice mutant of the base sequence set forth in SEQ ID NO: 7 or a fragment thereof;
(e) a polynucleotide encoding a species homolog of a polypeptide consisting of the amino acid sequence set forth in SEQ ID NO: 8 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to activity of a laminin γ1 chain. Pillarainen et al., J. Biol. Chem. 263 (14), 6751-6758, 1988 and U.S. Pat. No. 6,933,273 can be referenced for γ1 chains.

An amino acid sequence of a laminin γ1 chain can be:
(a) a polypeptide consisting of the amino acid sequence set forth in SEQ ID NO: 8 or a fragment thereof;
(b) a polypeptide having biological activity and one or more amino acids with a mutation selected from the group consisting of a substitution, an addition, and a deletion in the amino acid sequence set forth in SEQ ID NO: 8;
(c) a polypeptide encoded by an allele or a splice mutant of the base sequence set forth in SEQ ID NO: 7;
(d) a polypeptide which is a species homolog of the amino acid sequence set forth in SEQ ID NO: 8; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to the activity of a laminin γ1 chain. Pillarainen et al., J. Biol. Chem. 263 (14), 6751-6758, 1988 and U.S. Pat. No. 6,933,273 can be referenced with regard to γ1 chains.

As used herein, "protein", "polypeptide", "oligopeptide" and "peptide" are interchangeably used in the same meaning, referring to a polymer of amino acids of any length. Such a polymer may be a linear chain, a branched chain, or a cyclic chain. Amino acids may be naturally-occurring, non-naturally occurring, or altered amino acids. This term may also encompass those assembled into a complex of multiple polypeptide chains. This term also encompasses naturally or artificially-altered amino acid polymers. Examples of such an alteration include disulfide bond formation, glycosylation, lipidation, acetylation, phosphorylation, and any other operation or alteration (e.g., conjugation with a label component). This definition also encompasses, for example, polypeptides comprising one or more analogs of amino acids (e.g., including non-naturally-occurring amino acids and the like), peptide-like compounds (e.g., peptoid), and other alterations known in the art. For the protein of the invention (e.g., each laminin chain), a DNA encoding each chain gene of interest can be incorporated into an appropriate vector and introduced into a eukaryotic or prokaryotic cell using an expression vector which can be expressed in the respective host, and respective chains are expressed to obtain a desired protein. Host cells that can be used to express a laminin are not particularly limited. Examples thereof include prokaryotic host cells, such as *E. coli* and *Bacillus subtilis*, and eukaryotic host cells such as yeast, fungi, insect cells, plants and plant cells, and mammalian cells. Vectors constructed to express a laminin chain of interest or the like can be introduced into the aforementioned host cells, using transformation, transfection, conjugation, protoplast fusion, electroporation, particle gun technique, calcium phosphate precipitation, Agrobacterium method, direct microinjection or the like. Cells comprising a vector are grown in an appropriate culture medium to produce a laminin chain or the like used in the present invention, then the laminin chain is purified from the cells or culture medium to obtain the laminin chain or the like. The purification can be performed using size exclusion chromatography, HPLC, ion exchange chromatography, immunoaffinity chromatography, or the like.

As used herein, "amino acid" may be naturally occurring or non-naturally occurring, as long as the objective of the present invention is met.

As used herein, "polynucleotide", "oligonucleotide", and "nucleic acid" are interchangeably used in the same meaning, referring to a polymer of nucleotides of any length. These terms also encompass "oligonucleotide derivative" and "polynucleotide derivative". The "oligonucleotide derivative" and "polynucleotide derivative" are interchangeably used and refer to an oligonucleotide or polynucleotide which comprises a derivative of a nucleotide or an oligonucleotide or polynucleotide with a bond between nucleotides that is different from normal bonds. Specific examples of such oligonucleotides include: 2'-O-methyl-ribonucleotide; oligonucleotide derivatives with a phosphodiester bond in an oligonucleotide converted into phosphorothioate bond; oligonucleotide derivatives with a phosphodiester bond in an oligonucleotide converted into an N3'-β5' phosphoramidate bond; oligonucleotide derivatives with a ribose and a phosphodiester bond in an oligonucleotide converted into a peptide nucleic acid bond; oligonucleotide derivatives with a uracil in an oligonucleotide substituted with a C-5 propynyl uracil; oligonucleotide derivatives with uracil in an oligonucleotide substituted with a C-5 thiazole uracil; oligonucleotide derivatives with a cytosine in an oligonucleotide substituted with a C-5 propynyl cytosine; oligonucleotide derivatives with a cytosine in an oligonucleotide substituted with a phenoxazine-modified cytosine; oligonucleotide derivatives with a ribose in DNA substituted with a 2'-O-propylribose; oligonucleotide derivatives with a ribose in an oligonucleotide substituted with a 2'-methoxyethoxy ribose, and the like. Unless noted otherwise, specific nucleic acid sequences are intended to encompass sequences that are explicitly set forth, as well as their conservatively altered variants (e.g., degenerate codon substitutes) and complementary sequences. Specifically, a degenerate codon substitute can be achieved by making a sequence in which the third position of one or more selected (or all the) codons is substituted with a mixed base and/or deoxyinosine residue (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). As used herein, "nucleic acid" is interchangeably used with gene, cDNA, mRNA, oligonucleotide, and polynucleotide. As used herein, "nucleotide" may be naturally occurring or non-naturally-occurring.

As used herein, "gene" refers to an agent that defines a genetic trait. Normally, a gene is sequenced in a given order on a chromosome. A gene that defines the primary structure of a protein is referred to as a structural gene, and a gene that affects the expression thereof is referred to as a regulator gene. Herein, "gene" may refer to a "polynucleotide", "oligonucleotide", and "nucleic acid".

Amino acids may be mentioned herein by either their commonly known three letter symbol or their one letter symbol recommended by the IUPAC-IUB Biochemical Nomenclature Commission. Similarly, nucleotides may be mentioned by their commonly recognized one letter code. Similarity, identity, and homology of an amino acid sequence and a base sequence is compared by calculation using a default parameter with a sequence analysis tool, BLAST. For example, identity can be searched using BLAST 2.2.26 (published on Oct. 30, 2011) of the NCBI. Herein, values for identity generally refer to a value when aligned under the default condition using the aforementioned BLAST. However, when a higher value is obtained by changing a parameter, the highest value is considered the value of identity. When identity is evaluated in multiple regions, the highest value thereamong is considered the value of identity. Similarity is a value calculated by taking into consideration a similar amino acid in addition to identity.

As used herein, "polynucleotide that hybridizes under a stringent condition" refers to well-known conditions commonly used in the art. It is understood that laminins encoded by a "polynucleotide that hybridizes under a stringent condition" to nucleic acid sequences of each specifically-disclosed laminin chain may also be used as the laminins used in the present invention. Such a polynucleotide can be obtained using colony hybridization, plaque hybridization, southern blot hybridization, or the like, with a polynucleotide selected from the polynucleotides of the present invention used as a probe. Specifically, this refers to a polynucleotide that can be identified by performing hybridization at 65° C. in the presence of 0.7 to 1.0M of NaCl using a filter to which a colony or plaque-derived DNA is immobilized, and then washing the filter under the condition of 65° C. with a SSC (saline-sodium citrate) solution of 0.1 to 2 fold concentration (wherein the composition of the SSC solution of one fold concentration is 150 mM sodium chloride and 15 mM sodium citrate). Hybridization can be performed according to methods described in experimental documents such as Molecular Cloning 2nd ed., Current Protocols in Molecular Biology, Supplement 1-38, DNA Cloning 1: Core Techniques, A Practical Approach, Second Edition, Oxford University Press (1995). In this regard, sequences comprising only an A sequence or a T sequence are preferably excluded from sequences that hybridize under a stringent condition. Thus, the polypeptides (e.g., laminins) used in the present invention also encompass polypeptides encoded by a nucleic acid molecule that hybridizes under a stringent condition to a nucleic acid molecule encoding the polypeptide specifically described in the present invention. These low stringency conditions include: performing hybridization for 18 to 20 hours at 40° C. in a buffer comprising 35% formamide, 5×SSC, 50 mM Tris-HCl (pH 7.5), 5 mM EDTA, 0.02% PVP, 0.02% BSA, 100 µg/ml denatured salmon sperm DNA, and 10% (weight/volume) dextran sulfate; washing 1 to 5 hours at 55° C. in a buffer consisting of 2×SSC, 25 mM Tris-HCl (pH 7.4), 5 mM EDTA, and 0.1% SDS; and washing for 1.5 hours at 60° C. in a buffer consisting of 2×SSC, 25 mM Tris-HCl (pH 7.4), 5 mM EDTA, and 0.1% SDS.

Functional equivalents with one or more amino acid insertions, substitutions, or deletions, or additions to one or both ends in an amino acid sequence can be used as the functional equivalents of the invention. Herein, "one or more amino acid insertions, substitutions, or deletions, or additions to one or both ends in an amino acid sequence" mean that an alteration is made with multiple amino acid substitutions or the like that could occur naturally by a well-known technical method such as site-directed mutagenesis or a naturally-occurring mutation.

Altered amino acid sequences of each laminin chain or the like used in the present invention can be those with, for example, about 1 to 30, preferably about 1 to 20, more preferably about 1 to 9, still more preferably about 1 to 5, particularly preferably about 1 to 2 amino acid insertions, substitutions, or deletions, or additions to one or both ends. Altered amino acid sequences may be amino acid sequences having one or more (preferably, 1 or several, or 1, 2, 3, or 4) conservative substitutions in an amino acid sequence of each laminin chain or the like. Herein, "conservative substitution" means a substitution of one or more amino acid residues with other chemically similar amino acid residues which does not substantially alter the functions of a protein. Examples thereof include substitutions of a given hydrophobic residue with another hydrophobic residue, substitutions of a given polar residue with another polar residue having the same electric charge. Functionally similar amino acids that can be used for such a substitution are known in the art for each amino acid. Specific examples of non-polar (hydrophobic) amino acids include alanine, valine, isoleucine, leucine, proline, tryptophan, phenylalanine, methionine, and the like. Specific examples of polar (neutral) amino acids include glycine, serine, threonine, tyrosine, glutamine, asparagine, cysteine, and the like. Specific examples of (basic) amino acids having a positive electric charge include arginine, histidine, lysine and the like. Further, examples of (acidic) amino acids having a negative electric charge include aspartic acid, glutamic acid and the like.

The "agent" as used herein, in a broad sense, may be any substance or other elements (e.g., light, radiation, heat, electricity, and other forms of energy) as long as the intended objective can be achieved. Examples of such a substance include, but are not limited to, proteins, polypeptides, oligopeptides, peptides, polynucleotides, oligonucleotides, nucleotides, nucleic acids (including, for example, DNAs such as cDNA and genomic DNA and RNAs such as mRNA), polysaccharides, oligosaccharides, lipids, organic small molecules (e.g., hormones, ligands, information transmitting substances, organic small molecules, molecules synthesized by combinatorial chemistry, small molecules that can be used as a medicament (e.g., small molecule ligands and the like)) and complex molecules thereof. Typical examples of an agent specific to a polynucleotide include, but are not limited to, polynucleotides having complementarity with a certain sequence homology (e.g., 70% or greater sequence identity) to a sequence of the polynucleotide, polypeptides such as a transcription factor that bind to a promoter region, and the like. Typical examples of an agent specific to a polypeptide include, but are not limited to, antibodies directed specifically to the polypeptide or a derivative or analog thereof (e.g., single chain antibodies), specific ligands or receptors when the polypeptide is a receptor or ligand, substrates when the polypeptide is an enzyme, and the like.

As used herein, "normal cellular function" of a cell refers to a function which the cell inherently possesses when referring to a specific cell such as corneal endothelial cells is referred. For corneal endothelial cells, examples of such a function include, but are not limited to, ability to adapt to cornea transplantation, ZO-1 and $Na^+/K^+$-ATPase (Matsubara M, Tanishima T: Wound-healing of the corneal endothelium in the monkey: a morphometric study, Jpn J Ophthalmol 1982, 26: 264-273; Matsubara M, Tanishima T: Wound-healing of corneal endothelium in monkey: an autoradiographic study, Jpn J Ophthalmol 1983, 27: 444-450; Van Horn D L, Hyndiuk R A: Endothelial wound repair in primate cornea, Exp Eye Res 1975, 21: 113-124, and Van Horn D L, Sendele D D, Seideman S, Buco P J: Regenerative capacity of the corneal endothelium in rabbit and cat, Invest Ophthalmol Vis Sci 1977, 16: 597-613), and the like.

ZO-1 and $Na^+/K^+$-ATPase can be evaluated by observing the expression of a gene at a nucleic acid level such as RT-PCR or immunological means. Confirmation of $Na^+/K^+$-ATPase and ZO-1 expression and/or function at the same level as normal cells enables confirmation as to whether cells of interest have a normal function.

For the ability to adapt to cornea transplantation, tests of transplanting cultured cells can generally be conducted by mechanically scraping off the corneal endothelium as a bullous keratopathy model for experimental animals such as rabbits. However, since corneal endothelial cells of rabbits grow in vivo, it is not possible to deny the possibility of natural healing due to growth of corneal endothelial cells of hosts (Matsubara M, et al., Jpn J Ophthalmol 1982, 26: 264-273; Matsubara M, et al., Jpn J Ophthalmol 1983, 27: 444-450; Van Horn D L, et al., Exp Eye Res 1975, 21: 113-124 and Van Horn D L, et al., Invest Ophthalmol Vis Sci 1977, 16: 597-613). Thus, in order to more accurately evaluate the ability to adapt to transplantation, it is preferable to evaluate engraftment to primates. When the ability to adapt to transplantation to humans is evaluated, adaptability is evaluated in primates, such as cynomolgus monkeys, after at least one month, preferably at least two months, more preferably at least three months, still more preferably at least six months, and further still more preferably at least twelve months, for example. Confirmation of the ability to adapt to transplantation in primates such as monkeys is important, particularly in application to humans.

(General Techniques)

Molecular biological approaches, biochemical approaches, and microbiological approaches used herein are well known and conventional approaches in the art that are described in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997 and the like. For corneal endothelial cells, reports of Nancy Joyce et al. {Joyce, 2004 #161} {Joyce, 2003 #7} are well known. Since long-term culture and subculture results in fibroblast-like transformation as discussed above, research is currently being conducted for efficient culturing methods. The relevant portions (which can be the entire document) of the above documents are incorporated herein by reference.

PREFERRED EMBODIMENTS

Preferred embodiments are described hereinafter. It is understood that the embodiments are examples of the present invention, and the scope of the present invention should not be limited to such preferred embodiments. It is also understood that those skilled in the art can readily make alterations or modifications within the scope of the present invention by referring to the following preferred embodiments. It is further understood that any embodiments can be combined.

<Therapy or Prophylaxis>

In one aspect, the present invention provides a therapeutic or prophylactic agent for a disease, a disorder, or a condition of a cornea, such as a corneal endothelium, comprising at least one agent selected from the group consisting of laminins and fragments thereof. In this aspect, the present invention also provides at least one agent selected from the group consisting of laminins and fragments thereof for use in therapy or prophylaxis of a disease, a disorder, or a condition of a corneal endothelium. In this aspect, the present invention alternatively provides a method for therapy or prophylaxis of a disease, a disorder, or a condition of a corneal endothelium, the method comprising administering an effective amount of at least one agent selected from the group consisting of laminins and fragments thereof to a subject in need of the therapy or prophylaxis. In this aspect, it is understood that a therapeutic or prophylactic effect for corneas can be similarly achieved for corneal endothelia as well as epithelia and the like.

In a specific embodiment, the present invention provides a therapeutic or prophylactic agent for a disease, a disorder, or a condition of a corneal endothelium, comprising at least one agent selected from the group consisting of laminins and fragments thereof.

In one embodiment, the agent or laminin used in the present invention comprises an RGD sequence. Although not wishing to be bound by any theory, an RGD sequence is considered to be associated with cell adhesion. It is understood that a laminin with a prominent ability for cell adhesion can be used for therapy or prophylaxis of a disease, a disorder, or a condition of a corneal endothelium or for improvement thereof.

In another embodiment, the agent or laminin used in the present invention comprises an α5 chain. Although not wishing to be bound by any theory, this is because types of laminin comprising an α5 chain are demonstrated by the results shown in the Examples and the like to be capable of therapy or prophylaxis of a disease, a disorder, or a condition or a corneal endothelium or improvement thereof, and β and β chains are considered to have a certain degree of flexibility as long as an α5 chain is present.

In another embodiment, the agent or laminin used in the present invention comprises a γ1 chain. Although not wishing to be bound by any theory, this is because types of laminin comprising a γ1 chain are demonstrated by the results shown in the Examples and the like to be capable of therapy or prophylaxis of a disease, a disorder, or a condition or a corneal endothelium or improvement thereof, and α and β chains are considered to have a certain degree of flexibility as long as a γ1 chain is present.

In yet another embodiment, the agent or laminin used in the present invention comprises an α5 chain and/or a γ1 chain. Although not wishing to be bound by any theory, this is because types of laminin comprising an α5 chain and/or a γ1 chain are demonstrated by the results shown in the Examples and the like to be capable of therapy or prophylaxis of a disease, a disorder, or a condition or a corneal endothelium or improvement thereof, and the effect of laminin 511 and laminin 521 is demonstrated such that β is shown to have a certain degree of flexibility as long as an α5 chain and/or a γ1 chain is determined.

In one preferred embodiment, the laminin comprises laminin 511 and laminin 521. Thus, the agent of the invention may be laminin 511, laminin 521, or a fragment thereof in this embodiment. Any fragment may be used as the fragment of laminin 511 or laminin 521 of the invention, as long as the fragment is capable of therapy or prophylaxis of a disease, a disorder, or a condition of a corneal endothelium or improvement thereof. Examples of such fragments include, but are not limited to, a laminin 511-E8 fragment and laminin 521 fragment (SEQ ID NOs: 9 and 10 (nucleic acid sequence and amino acid sequence) and SEQ ID NOs: 11 and 12 (nucleic acid sequence and amino acid sequence), respectively) (see Taniguchi Y, Ido H, Sanzen N, Hayashi M, Sato-Nishiuchi R, Futaki S, Sekiguchi K. The C-terminal region of laminin beta chains modulates the integrin binding affinities of laminins. J Biol Chem. 284: 7820-7831, 2009; available from Nippi. Inc.) A laminin 511-E8 fragment and laminin 521 fragment are fragments obtained by elastase treatment and are comprised of three LG domains (LG1 to LG3) in the a chain C-terminal region and a portion of a coiled-coil domain of a heterotrimer. An E8 fragment is regarded as corresponding to an integrin binding site of a heterotrimer molecule in which an α chain, a β chain and a γ chain of a laminin assemble via a coiled-coil domain with one another. Thus, a fragment of a full length laminin in which an integrin binding site is substantially retained can be used as a preferred fragment. It is understood that such a fragment can be made by an appropriate alteration based on information on laminin 511-E8 and laminin 521 fragments.

In this regard, the E8 fragment of a human laminin α5β1γ1 (herein, also referred to as "human laminin 511-E8") means a fragment of human laminin α5β1γ1 (hereinafter, also referred to as "human laminin 511") corresponding to the E8 fragment of mouse laminin allyl (hereinafter, also referred to as "mouse laminin 111-E8"). As used herein, the term "laminin 511-E8 fragment" is also denoted as "Laminin 511-E8 fragment", "Laminin 511 E8", or "Laminin 511-E8". The E8 fragment of a laminin has been identified as a fragment with strong cell adhesion activity among fragments that can be obtained by digesting murine laminin allyl (hereinafter, referred to as "mouse laminin 111") with elastase (Edgar D., Timpl R., Thoenen H. The heparin-binding domain of lamininis responsible for its effects on neurite outgrowth and neuronal survival. EMBO J., 3: 1463-1468, 1984., Goodman S L., Deutzmann R., von der Mark K. Two distinct cell-binding domains in laminin can independently promote nonneuronal cell adhesion and spreading. J. Cell Biol., 105: 589-598, 1987). For human laminin 511 and human laminin 332, the presence of a fragment corresponding to the mouse laminin 111-E8 is assumed upon digestion with elastase. The human laminin 511-E8 fragment used in the present invention only needs to be a fragment of human laminin 511 with the same cell adhesion activity, structure, and approximate molecular weight as mouse laminin 111-E8, and it is not required to be an elastase digestion product of human laminin 511. A method of manufacturing a human laminin 511-E8 fragment is not particularly limited. Examples of such a method include a method of digesting a full length human laminin 511 with a proteolytic enzyme such as elastase in order to fractionate and purify a fragment of interest, a method of manufacture as a recombinant protein, and the like. Manufacturing as a recombinant protein is preferred from the viewpoint of manufacturing quantity, quality consistency, manufacturing cost, or the like. A recombinant human laminin 511-E8 fragment can be manufactured by appropriately using a known genetic engineering technique. A method of manufacturing a recombinant human laminin 511-E8 fragment can manufacture, for example, by obtaining DNA encoding a protein of each of α chain, β chain, and γ chain of a human laminin 511-E8 fragment, inserting each obtained DNA into an expression vector, expressing the resulting three kinds of expression vectors by cotransfection into an appropriate host cell, and purifying a protein forming a trimer with a known method (for example, see Hiroyuki Ido, et al, "The requirement of the glutamic acid residue at the third position from the carboxyl termini of the laminin γ chains in integrin binding by laminins" The Journal of Biological Chemistry, 282, 11144-11154, 2007). Japanese Patent Application No. 2011-78370 can be referred to for a specific production method. Similar fragments can also be produced by using human laminin 521. This is called a laminin 521-E8 fragment. It is understood that such a fragment can be made in the same manner as a laminin 511-E8 fragment and retains the same activity as a laminin 511-E8 fragment. In the present invention, it is understood that an E8 fragment can be similarly manufactured for any laminin comprising an α5 chain and/or a γ1 chain. It is also understood that such an E8 fragment can be used similarly to a full length laminin in the present invention.

In a preferred embodiment, the laminin comprises laminin 511 (α5β1γ1) and laminin 521 (α5β2γ1), or the agent is laminin 511, laminin 521, a laminin 511-E8 fragment, or a laminin 521-E8 fragment.

In another embodiment, the fragment used in the present invention has cell adhesion capability of a cell of a cornea (corneal endothelial cell).

In one embodiment, concentration of the agent used (e.g., laminin or a fragment thereof) can be any concentration (also referred to as an effective concentration, or therapeutically effective concentration for therapy or prophylactically effective concentration for prophylaxis) as long as there is a therapeutic or prophylactic effect. Examples thereof include, but are not limited to, about 0.1 nM or greater, about 0.2 nM or greater, about 0.3 nM or greater, about 0.4 nM or greater, about 0.5 nM or greater, about 0.6 nM or greater, about 0.7 nM or greater, about 0.8 nM or greater, about 0.9 nM or greater, about 1 nM or greater, about 2 nM or greater, about 2.1 nM or greater, about 3 nM or greater, about 4 nM or greater, about 5 nM or greater, about 6 nM or greater, about 7 nM or greater, about 8 nM or greater, about 9 nM or greater, about 10 nM or greater, about 15 nM or greater, about 20 nM or greater, about 21 nM or greater, about 25 nM or greater, about 30 nM or greater, about 40 nM or greater, about 50 nM or greater, about 60 nM or greater, about 70 nM or greater, about 80 nM or greater, about 90 nM or greater, about 100 nM or greater, and the like.

In one embodiment, the site targeted by the present invention includes the corneal endothelium. Thus, the diseases, disorders, or conditions targeted by the present invention include, but are not limited to, a disease, a disorder, or a condition of a corneal endothelium targeted by the present invention.

In one embodiment, the ophthalmic site is from a primate. In another embodiment, the ophthalmic site is from a human.

In one embodiment, the ocular cell is from a primate. In another embodiment, the cell of the eye is from a human.

In one embodiment, the corneal endothelium is from a primate. In another embodiment, the corneal endothelium is from a human.

In one embodiment, the cell of the corneal endothelium is from a primate. In another embodiment, the cell of the corneal endothelium is from a human. Although not wishing to be bound by any theory, since the therapeutic or prophylactic effect with a laminin in a corneal endothelium model in the Examples of the present specification is demonstrated not only in rabbits but also in primates, it is the understanding of those skilled in the art that a similar therapeutic or prophylactic effect is achieved in any mammal.

Examples of diseases, disorders, or conditions of a corneal endothelium targeted by the present invention include diseases which require transplantation of a corneal endothelium, such as bullous keratopathy, corneal edema, corneal leukoma, especially bullous keratopathy caused by a corneal endothelium disorder due to corneal dystrophy, trauma or internal ophthalmic surgery. A graft can be used in therapy thereof. Examples of the cause of such bullous keratopathy, corneal endothelium disorder, or the like include surgery, as well as Fuchs' corneal endothelial dystrophy, trauma, pseudoexfoliation syndrome, corneal endotheliitis, and the like.

In another embodiment, examples of the disease, disorder, or condition of a corneal endothelium include photophobia, blurred vision, visual impairment, ophthalmalgia, epiphora, hyperemia, pain, bullous keratopathy, eye discomfort, diminished contrast, glare, edema of the corneal stroma, bullous keratopathy, corneal turbidity, and the like.

Examples of subjects of therapy or prophylaxis of a disease, a disorder, or a condition of a corneal endothelium of the invention include mammals (e.g., humans, mice, rats, hamsters, rabbits, cats, dogs, cows, sheep, monkeys, and the like), and are preferably primates (e.g., humans).

In one embodiment, the corneal endothelium targeted by the present invention comprises a corneal endothelial layer, a Descemet's membrane, or both.

In a preferred embodiment, the corneal endothelium targeted by the present invention comprises a Descemet's membrane. The corneal endothelium targeted by the present invention includes corneal endothelium with a Descemet's membrane in a detached state. The technique of the invention was found to be capable of treating a Descemet's membrane in a detached state, complete recovery from which had been difficult with conventional techniques. The technique of the invention can also be understood as qualitative improvement in terms of this point.

<Combined Therapy>

In another aspect, the present invention provides a therapeutic or prophylactic agent for a disease, a disorder, or a condition of a corneal endothelium, using at least one agent selected from the group consisting of laminins and fragments thereof and a corneal endothelial cell. In this regard, the agent and corneal endothelial cell of the invention may be used as a mixture or administered independently. Thus, in this aspect, the present invention provides a method for therapy or prophylaxis of a disease, a disorder, or a condition of a corneal endothelium, the method comprising administering an effective amount of at least one agent selected from the group consisting of laminins and fragments thereof to a subject in need of the therapy or prophylaxis and administering a corneal endothelial cell and/or a ROCK inhibitor to the subject. It is understood that the agent (laminin, fragment thereof, or the like), the corneal endothelial cell, the ROCK inhibitor and the like used in the method of the present invention of this aspect can be used in any form explained herein.

Although not wishing to be bound by any theory, the opacity in a cornea was cleared, corneal thickness was reduced, and markers indicating a function returned to normal, as demonstrated in the Examples, by using a corneal endothelial cell and at least one agent selected from the group consisting of laminins and fragments thereof in the therapy itself. Furthermore, a therapeutic result that had been previously unattainable was achieved. Further, the time required for therapy is characterized in being significantly shorter, as demonstrated in cases where a significant effect manifested in two to three days and attained near complete recovery in one week.

In another aspect, the present invention provides a therapeutic or prophylactic agent for a disease, a disorder, or a condition of a corneal endothelium, using at least one agent selected from the group consisting of laminins and fragments thereof and a ROCK inhibitor (this term is synonymous with "Rho kinase inhibitor"). In this regard, the agent and the ROCK inhibitor of the invention may be used as a mixture or administered independently. It is understood that the agent (laminin, fragment thereof, or the like) used in the method of the invention of this aspect can be used in any form explained herein.

In the present invention, "Rho kinase" refers to serine/threonine kinase which is activated with activation of Rho. Examples thereof include ROKα (ROCK-II: Leung, T. et al., J. Biol. Chem., 270, 29051-29054, 1995), p160ROCK (ROKβ, ROCK-I: Ishizaki, T. et al., The EMBO J., 15(8), 1885-1893, 1996), and other proteins having serine/threonine kinase activity.

Examples of ROCK inhibitors include compounds disclosed in the following documents: U.S. Pat. No. 4,678,783, Japanese Patent No. 3421217, International Publication No. WO 95/28387, International Publication No. WO 99/20620, International Publication No. WO 99/61403, International Publication No. WO 02/076976, International Publication No. WO 02/076977, International Publication No. WO 2002/083175, International Publication No. WO 02/100833, International Publication No. WO 03/059913, International Publication No. WO 03/062227, International Publication No. WO 2004/009555, International Publication No. WO 2004/022541, International Publication No. WO 2004/108724, International Publication No. WO 2005/003101, International Publication No. WO 2005/039564, International Publication No. WO 2005/034866, International Publication No. WO 2005/037197, International Publication No. WO 2005/037198, International Publication No. WO 2005/035501, International Publication No. WO 2005/035503, International Publication No. WO 2005/035506, International Publication No. WO 2005/080394, International Publication No. WO 2005/103050, International Publication No. WO 2006/057270, International Publication No. WO 2007/026664, and the like. Such compounds can be manufactured by the methods described in the respective documents where the compounds are disclosed. The specific examples thereof include 1-(5-isoquinolinesulfonyl) homopiperazine or a salt thereof (e.g., fasudil (1-(5-isoquinolinesulfonyl) homopiperazine)), (+)-trans-4-(1-aminoethyl)-1-(4-pyridylcarbamoyl)cyclohexane((R)-(+)-trans-(4-pyridyl)-4-(1-aminoethyl)-cyclohexanecarboxamide) or a salt thereof (e.g., Y-27632 ((R)-(+)-trans-(4-pyridyl)-4-(1-aminoethyl)-cyclohexanecarboxamide dehydrochloride monohydrate) and the like) and the like. For these compounds, a commercially available product (Wako Pure Chemical Industries, Ltd, Asahi Kasei Pharma Corporation, or the like) can also be suitably used.

In a preferred embodiment, examples of the ROCK inhibitor (Rho kinase inhibitor) used in the present invention include, but are not limited to, Y-27632 ((R)-(+)-trans-(4-pyridyl)-4-(1-aminoethyl)-cyclohexanecarboxamide dehydrochloride monohydrate) and the like.

Any corneal endothelial cell can be used as the "corneal endothelial cell" used herein. The corneal endothelial cell may be isolated or cultured. Corneal endothelial cells may be those cultured by a normal culturing method with an approach developed by the inventors or those cultured by other approaches. For instance, corneal endothelial cells cultured by the approach described in WO 2013/100208 can be used. For example, fibrillization inhibiting agent can be constantly present during culture of the corneal endothelial cells, while an adhesion promoting agent can be present for a certain period (e.g., 24 to 72 hours, or 48 hours or the like), then removed momentarily, and then present for a certain period (e.g., 24 to 72 hours, or 48 hours or the like; this period may change each time or remain the same). Alternatively, these culturing methods may optionally be a method without using an adhesion promoting agent. For instance, the following three types are examples thereof.

(Culturing Method 1)

Y-27632 (e.g., available from WAKO, catalog number: 253-00513), which is a ROCK inhibitor with adhesion promoting action, is added for 48 hours with a final concentration of 10 µmol/l during primary culture and subculture.

(Culturing Method 2)

A ROCK inhibitor Y-27632 is constantly added during culture with a final concentration of 10 µmol/l.

(Culturing Method 3)

Cells are cultured in a basal medium supplemented with SB431542 (e.g., available from Merck Millipore, Billerica, Mass.) (1 µmol/l) and SB203580 (1 µmol/l) without adding Y-27632.

The medium to be used may be a medium component that has been sold and used or a component developed separately for corneal endothelia. Examples of such a medium component include, but are not limited to, OptiMEM, DMEM, M199, MEM, and the like (which are available from INVITROGEN and the like). Typical examples include, for humans, Opti-MEM I Reduced-Serum Medium, Liquid (INVITROGEN catalog No.: 31985-070)+8% FBS (BIO-WEST, catalog No.: S1820-500)+200 mg/ml $CaCl_2.2H_2O$ (SIGMA catalog No.: C7902-500G)+0.08% chondroitin sulfate (SIGMA catalog No.: C9819-5G)+20 µg/ml ascorbic acid (SIGMA catalog No.: A4544-25G)+50 µg/ml gentamicin (INVITROGEN catalog No.: 15710-064)+5 ng/ml EGF (INVITROGEN catalog No.: PHG0311) acclimated for a 3T3 feeder cell as the basal medium and SB431542 (1 µmol/l) and SB203580 (1 µmol/l).

<1> Harvesting and Culturing Corneal Endothelial Cells in a Test Tube

Corneal endothelial cells are harvested from the cornea of a recipient himself or an appropriate donor using a conventional method. Considering the transplantation conditions in the present invention, corneal endothelial cells derived from the same species may be prepared. For example, the Descemet's membrane and endothelial cell layer of corneal tissue are detached from the corneal stroma and then are transferred to a culture dish and are treated with Dispase or the like. Corneal endothelial cells fall off the Descemet's membrane thereby. Corneal endothelial cells remaining on the Descemet's membrane can be taken off by pipetting or the like. After the removal of the Descemet's membrane, the corneal endothelial cells are cultured in a culture liquid (e.g., described in WO 2013/100208). As a culture or culture liquid, the following can be used for example: FBS (fetal bovine serum) (e.g., BIOWEST, catalog number: S1820-500), b-FGF (basic fibroblast growth factor) (e.g., INVITROGEN, catalog number: 13256-029), and an antibiotic substance, such as penicillin or streptomycin, may be appropriately added to commercially available DMEM (Dulbecco's Modified Eagle's Medium) (e.g., INVITROGEN, catalog number: 12320 or the like), followed by adding components of a culture normalizer shown in WO 2013/100208. Coating the agent of the invention for culturing promotes the adhesion of corneal endothelial cells to the surface of a culture container, resulting in excellent growth. When culturing by adding a laminin to the culture liquid, it is preferable to use a culture dish with a surface coated with type I collagen, type IV collagen, fibronectin, laminin, or extracellular matrix of bovine corneal endothelial cells or the like. Alternatively, it is possible to use a common culture container which is treated with a commercially available coating agent such as FNC coating Mix® (50 ml (AES-0407), ATHENA, catalog number: 0407). The temperature conditions for culturing corneal endothelial cells are not particularly limited, as long as the corneal endothelial cells grow. For example, the temperature is about 25° C. to about 45° C., and is preferably about 30° C. to about 40° C. considering the growth efficiency, and more preferably about 37° C. The culturing method is conducted in an environment of about 5 to 10% $CO_2$ concentration under humidification in a normal cell culturing incubator.

<2> Subculturing

After the growth of corneal endothelial cells subjected to culturing, the cells may be subcultured. Preferably, subculturing is performed upon sub-confluence or confluence. Subculturing may be performed as follows. First, cells are treated with trypsin-EDTA or the like so that the cells are detached from the surface of a culture container. The cells are then collected. The culture normalizer or medium of the invention is added to the collected cells to obtain a cell suspension. It is preferable to subject the cells to centrifugation when or after the cells are collected. The centrifugation enables preparation of a high density cell suspension. Preferable cell density is about 1 to $2\times10^6$ cells/mL. Examples of centrifugation conditions include, but are not limited to, 500 rpm (30 g) to 1000 rpm (70 g), for to 10 minutes.

The cell suspension is seeded to a culture container and subjected to culture in the same manner as in the aforementioned primary culture. While the dilution factor upon subculturing varies depending on the state of the cells, it is about 1:2 to 1:4 and is preferably 1:3. Subculturing may be conducted under culture conditions similar to those of the aforementioned primary culture. The incubation time varies depending on the state of cells to be used or the like. Examples thereof include 7 to 30 days. The aforementioned subculturing may be performed multiple times as needed. When a ROCK inhibitor or the like is used, the cell adhesion in an initial period of the culture can be enhanced, resulting in shorter culturing period.

<Purification of High Density Corneal Endothelial Cell Using Density Gradient Centrifugation>

In one embodiment, cells can be used in the present invention after purifying high density corneal endothelial cells using density gradient centrifugation. The method therefor is typically the following. Cultured human corneal endothelial cells, a mixture of low density cells and high density cells, can be subjected to density gradient centrifugation for 15 minutes at 800×g using a suitable means (e.g., OptiPrep™). The cells contained in pellets and supernatant can be collected, and suitable number of each of the cells (e.g., 420 cells/mm$^2$) are seeded and cultured as the pellet group and supernatant group, respectively. The morphology is observed with a phase contrast microscope after 30 days to analyze the expression of a corneal endothelial function associated marker by immunostaining and to measure the cell density/cell area. The cultured cells, after centrifugation, exhibit monolayer polygonal cell morphology in both the pellet group and the supernatant group. Cells exhibiting Na$^+$/K$^+$-ATPase and ZO-1 expression are obtained. In addition, the pellet group generally has a significantly higher cell density. The median value (interquartile range) of cell area is generally lower in the pellet group with less dispersion. Thus, it is understood that high density cells can be purified by density gradient centrifugation and used in the present invention.

<Coating>

In one embodiment, the present invention provides a therapeutic or prophylactic agent for a disease, a disorder, or a condition of a corneal endothelium, comprising at least one agent selected from the group consisting of laminins and fragments thereof, wherein the agent is injected into an eye thereby being contacted with tissue in the eye. Thus in this aspect, the present invention also provides a method for therapy or prophylaxis of a disease, a disorder, or a condition of a corneal endothelium, the method comprising administering an effective amount of at least one agent selected from the group consisting of laminins and fragments thereof to a subject in need of the therapy or prophylaxis, wherein the agent is injected into an eye of the subject thereby being contacted with tissue in the eye. It is understood that the agent (laminin, fragment thereof, or the like) used in the method of the invention in this aspect can be used in any form explained herein. In this regard, it is understood that the agent is injected into an eye thereby being contacted with tissue in the eye, resulting in the formation of a coating (also referred to as a laminin coating herein) of at least one agent selected from the group consisting of laminins and fragments thereof in the eye to promote healing of the cornea.

In one embodiment, the concentration of the agent used upon coating may be any concentration, as long as there is a therapeutic or prophylactic effect (also referred to as an effective concentration; also referred to as effective coating concentration for coating). Examples thereof include, but are not limited to, about 0.1 nM or greater, about 0.2 nM or greater, about 0.3 nM or greater, about 0.4 nM or greater, about 0.5 nM or greater, about 0.6 nM or greater, about 0.7 nM or greater, about 0.8 nM or greater, about 0.9 nM or greater, about 1 nM or greater, about 2 nM or greater, about 2.1 nM or greater, about 3 nM or greater, about 4 nM or greater, about 5 nM or greater, about 6 nM or greater, about 7 nM or greater, about 8 nM or greater, about 9 nM or greater, about 10 nM or greater, about 15 nM or greater, about 20 nM or greater, about 21 nM or greater, about 25 nM or greater, about 30 nM or greater, about 40 nM or greater, about 50 nM or greater, about 60 nM or greater, about 70 nM or greater, about 80 nM or greater, about 90 nM or greater, about 100 nM or greater, and the like.

In one preferred embodiment, corneal cells such as corneal endothelial cells may be further administered after, simultaneously with, or before the agent is injected near the corneal endothelium thereby being contacted with cells or tissue constituting the corneal endothelium. Thus, corneal endothelial cells may be administered independently from the agent in the present invention. The timing of administering a corneal cell such as a corneal endothelial cell is preferably after or simultaneously with the injection of the agent into an eye and contact with tissue in the eye (coating), and more preferably after the agent is injected into an eye thereby being contacted with tissue in the eye. It was revealed that engraftment of a corneal cell such as a corneal endothelial cell administered in such a manner onto corneal endothelial tissue is promoted by the presence of a coating to significantly promote a therapeutic effect.

In another aspect, the present invention is a therapeutic or prophylactic agent for a disease, a disorder, or a condition of a corneal endothelium, comprising a mixture of at least one agent selected from the group consisting of laminins and fragments thereof and a cornea cell such as a corneal endothelial cell, wherein at least one agent selected from the group consisting of laminins and fragments thereof, which is different from at least one agent selected from the group consisting of laminins and fragments thereof, is injected into an eye thereby being contacted with tissue in the eye, preferably with a portion of tissue subjected to therapy of prophylaxis (e.g., corneal endothelium or the like). Thus, in this aspect, the present invention provides a method for therapy or prophylaxis of a disease, a disorder, or a condition of a corneal endothelium, the method comprising administering an effective amount of at least one agent selected from the group consisting of laminins and fragments thereof to a subject in need of the therapy or prophylaxis, wherein the agent is provided while being mixed with a corneal endothelial cell, and at least one agent selected from the group consisting of laminins and fragments thereof is injected into an eye thereby being contacted with tissue in the eye. In this aspect, the aforementioned mixture may be administered before, simultaneously with, or after at least one agent selected from the group consisting of laminins and fragments thereof is injected into an eye thereby being contacted with tissue in the eye (coating). The timing of administering a mixture is preferably after or simultaneously with the injection of the agent an eye and contact with tissue in the eye, and more preferably after the agent is injected into an eye thereby being contacted with tissue in the eye. Although not wishing to be bound by any theory, it is understood that such a coating provides an environment where establishment of a mixture of the aforementioned agent and a cornea cell such as a corneal endothelial cell is promoted such that healing of the cornea is promoted. It is understood that a cornea cell such as a corneal endothelial cell can be used in any form explained herein or any known form.

In a preferred embodiment, the therapeutic or prophylactic agent of the invention, in a form of coating, further comprises a ROCK inhibitor. A ROCK inhibitor and the agent may be concomitantly, sequentially, or independently administered.

A ROCK inhibitor may be in any form explained separately herein and is preferably Y-27632 ((R)-(+)-trans-(4-pyridyl)-4-(1-aminoethyl)-cyclohexanecarboxamide dihydrochloride monohydrate) or the like.

In one embodiment in the present invention, an agent mixed with a cornea cell such as the corneal endothelial cell is about 2.1 nM or greater, and the agent to be injected is about 21 nM or greater.

(Use)

In another aspect, the present invention provides use of at least one agent selected from the group consisting of laminins and fragments thereof in manufacture of a medicament for therapy or prophylaxis of a disease, a disorder, or a condition of a corneal endothelium. Alternatively in this aspect, the present invention provides use of at least one agent selected from the group consisting of laminins and fragments thereof for therapy or prophylaxis of a disease, a disorder, or a condition of a corneal endothelium. It is understood that the agent (laminin, fragment thereof, or the like) used in the use of the invention can be used in any form explained herein.

Reference literatures such as scientific literatures, patents, and patent applications cited herein are incorporated herein by reference to the same extent that the entirety of each document is specifically described. As used herein, "or" is used when "at least one or more" matters listed in the sentence can be used. When it is explicitly described as "within the range of two values" herein, the two values themselves are also included in the range. The description "about" as used herein indicates, unless specifically noted otherwise, the numerical value rounded up or down to an effective number, or for a specific value, the value thereof ±10%.

As described above, the present invention has been explained while showing preferred embodiments to facilitate understanding. The present invention is explained hereinafter based on Examples. The aforementioned explanation and the following Examples are not provided to limit the present invention, but for the sole purpose of exemplification. Thus, the scope of the present invention is not limited to the embodiments and Examples specifically described herein and is limited only by the scope of claims.

EXAMPLES

The Examples of the present invention are disclosed hereinafter. Biological samples and the like, when applicable, were handled in accordance with standards specified by the Ministry of Health, Labour and Welfare, Ministry of Education, Culture, Sports, Science and Technology, or the like.

(Experimental Approach: Preparation of Cultured Corneal Endothelial Cell)
(Approach)*(Cultured)

Rabbit corneal endothelial cells (RCECs, source of cells and culture method): For rabbit corneal endothelial cells used in the following experiment, the Descemet's membrane comprising the endothelial cell layer was detached from the corneal tissue and was placed in 1.2 U/ml Dispase I [(Sanko Pure Chemical) catalog number: GD81060] dissolved in DMEM (Gibco-Invitrogen) and was inoculated at 37° C. After one hour, the corneal endothelial cells were detached and collected from the Descemet's membrane by pipetting, and were centrifuged for 5 minutes at 1000 rpm to remove the supernatant. A culture medium was added and mixed with precipitated corneal endothelial cells. The entire volume thereof was seeded onto a 6-well plate coated with FNC Coating Mix. The culture medium used was DMEM (catalog number: 12320; Gibco-Invitrogen) supplemented with 10% FBS, 50 μg/ml gentamicin (catalog number: 15710-064; Invitrogen), 10 μg/ml Y-27632 (catalog number: 6880005, Calbiochem, La Jolla, Calif.), and 2 ng/ml basic fibroblast growth factor (catalog number: 13256-029; bFGF; Invitrogen). As in monkeys, previously reported lines [Koizumi N et al., Exp Eye Res., 2012; 95: 60-67; Koizumi N et al., Invest Ophthalmol Vis Sci. 2007; 48: 4519-4526; Okumura N et al., Am J Pathol. 2012; 181: 268-277] were used for culturing rabbit corneal endothelial cells (CEC).

The medium was exchanged every two days. Subculture was performed at 50 to 80% confluence. The subculturing method included washing cells with $Ca^{2+}Mg^{2+}$ free PBS (PBS-; Nissui Pharmaceutical Co., Ltd., Tokyo. Japan), adding TrypLE™ N Select (catalog number: 12563; Invitrogen), and incubating for 5 minutes at 37° C. After the cells were detached and collected from the plate and were centrifuged for 5 minutes at 1000 rpm, a culture medium was added to produce a cell suspension. The cells were seeded at a density of 1:2 on a plate coated with FNC Coating Mix.

This was used as the cultured corneal endothelial cells.

(Statistical Analysis)

A statistically significant difference (p value) in mean values comparing two samples was determined using Student's t test. A statistically significant difference in comparing multiple sample sets was analyzed using Dunnett's multiple comparison test. The values shown in the graph represent mean±SE.

Example 1: Cultured Corneal Endothelium Transplantation Experiment in Rabbit Bullous Keratopathy Model Using Laminin 511-E8 Fragment In this Example, a laminin 511-E8 fragment was used as a laminin and a rabbit bullous keratopathy model was used as a pathological model for cultured corneal endothelium transplantation.

(Materials and Methods)
(Used Reagents Etc.)
The following reagents and the like were used in this Example.
*Cultured rabbit corneal endothelial cells (also abbreviated as RCEC; prepared as disclosed above)
*Laminin 511 E8 fragment (Nippi. Inc., 382-02413)
*Rabbit bullous keratopathy model (produced as described below in (Transplantation method))
*Others mentioned in the experimental approach
(Transplantation Method)

The experiment shown in FIG. 1 was conducted as follows.

A rabbit corneal endothelium was mechanically detached using a 20 gauge silicone needle (Soft Tapered Needle; Inami & Co., Ltd., Tokyo, Japan) to make a bullous keratopathy model. The control group is a produced model that was not injected with cells. The RCEC group was injected with cultured rabbit corneal endothelial cells in the anterior chamber of the produced model and was maintained in a face-down posture for three hours. Further, the RCEC+E8 group was injected with cultured rabbit corneal endothelial cells, together with DMEM containing laminin 511-E8 fragments adjusted to a concentration of 2.1 nM, into the anterior chamber of the produced model and was maintained in a face-down posture for three hours.

(Measurement of Corneal Thickness)

The measurement experiment shown in FIG. 2 was conducted as follows.

Figure 1:
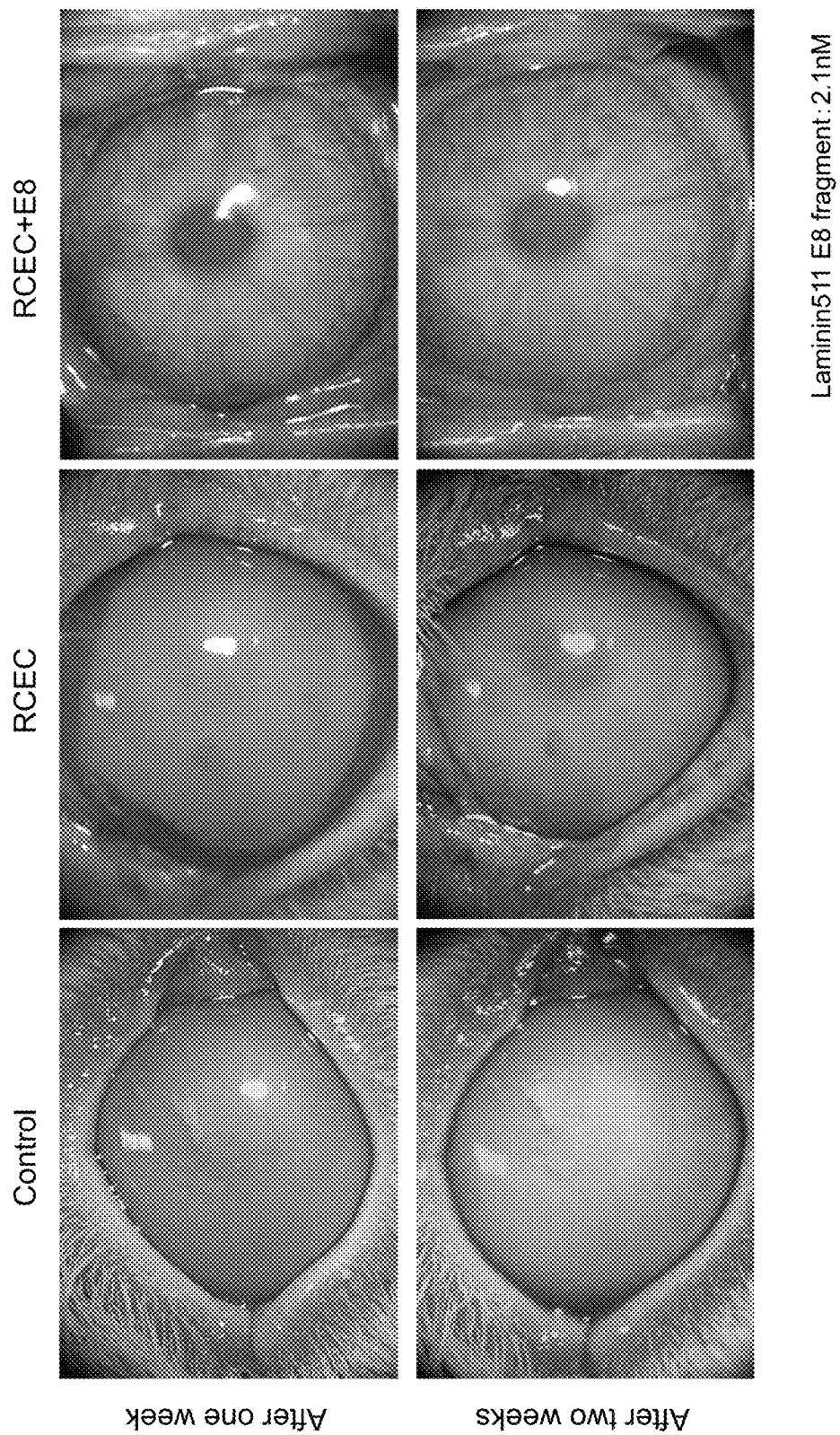
FIG. 1 shows pictures of an anterior ocular segment after cultured corneal endothelium transplantation in a rabbit bullous keratopathy model using a laminin 511-E8 fragment. Pictures of an anterior ocular segment are shown, from the left, for Control: an anterior ocular segment with rabbit corneal endothelial cells mechanically scraped off as a control, RCEC: an anterior ocular segment of a produced model, which was injected with cultured rabbit corneal endothelial cells into the anterior chamber and maintained in a face-down posture for three hours, and RCEC+E8: an anterior ocular segment of a produced model which was injected with cultured rabbit corneal endothelial cells into the anterior chamber with DMEM containing laminin 511-E8 fragments adjusted to a concentration of 2.1 nM and maintained in a face-down posture for three hours. The top row shows pictures after one week and the bottom row shows pictures after two weeks.

The corneal thickness of an individual produced in FIG. 1 was measured sequentially with an ultrasound pachymeter (SP-2000; Tomey, Nagoya, Japan). When unmeasurable, 1200 μm, which is the measurable upper limit value, was used.

(Histological Examination)

The histological examination in FIG. 3 was conducted as follows. The examination was checking normal functioning with immunostaining using $Na^+/K^+$-ATPase and ZO-1. This is for examining the functions of corneal endothelial cells, pumping function and barrier function. $Na^+/K^+$-ATPase and ZO-1 indicate normalcy of corneal endothelial cell functions, pumping function and barrier function, respectively. The approach is as follows.

(Cell Observation Method (Histological Test) Such as Staining)

Cells were observed with a phase contrast microscope. After cells were immobilized, ZO-1 and $Na^+/K^+$-ATPase were used as function associated markers and immunostaining was applied for observation with a fluorescence microscope. For tissue staining inspection, cornea tissue extracted from a rabbit was immobilized with 4% formaldehyde for 10 minutes at room temperature (RT) and was incubated for 30 minutes with 1% bovine serum albumin (BSA). To find the phenotype of regenerated corneal endothelial tissue, immunohistochemical analysis was performed on an adhesion binding associated protein ZO-1 and pumping function associated protein $Na^+/K^+$-ATPase. ZO-1 and $Na^+/K^+$-ATPase were used as markers associated with cell functions. ZO-1 and $Na^+/K^+$-ATPase were stained using 1:200 dilution of ZO-1 polyclonal antibodies (Zymed Laboratories, Inc., South San Francisco, Calif.) and $Na^+/K^+$-ATPase monoclonal antibodies (Upstate Biotec, Inc., Lake Placid, N.Y.). 1:2000 dilution of Alexa Fluor®488 label (Life Technologies Corp., Carlsbad, Calif.) was used as the secondary antibody. The nucleus of cells was then stained with DAPI (Vector Laboratories, Inc., Burlingame, Calif.). The cell morphology was further stained with 1:400 dilution of Alexa Fluor® 488-conjugated phalloidin (Life Technologies Corp., Carlsbad, Calif.). The slide was then observed under a fluorescence microscope (TCS SP2 AOBS; Leica Microsystems, Welzlar, Germany).

(Results)

Figure 3:
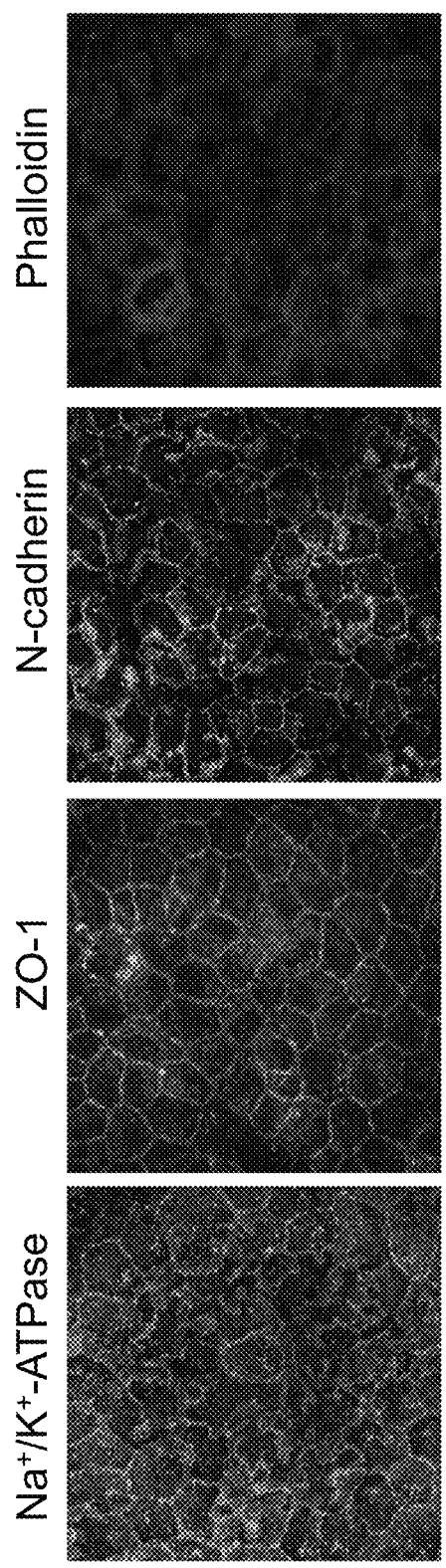
FIG. 3 shows results of histological examination after cultured corneal endothelium transplantation using a laminin 511-E8 fragment.

The results are shown in FIGS. 1 to 3. FIG. 1 shows pictures of an anterior ocular segment after cultured corneal endothelium transplantation in a rabbit bullous keratopathy model using a laminin 511-E8 fragment. Pictures of the anterior ocular segment are shown for, from the left, Control: control with rabbit corneal endothelial cells mechanically scraped off, RCEC: produced model injected with cultured rabbit corneal endothelial cells into the anterior chamber and maintained in a face-down posture for three hours, and RCEC+E8: produced model with cultured rabbit corneal endothelial cells injected into the anterior chamber, with DMEM comprising laminin 511-E8 fragments adjusted to a concentration of 2.1 nM, and maintained in a face-down posture for three hours. The top row shows pictures after one week and the bottom row shows pictures after two weeks. The cornea was turbid in the control group and the RCEC group, but the cornea was transparent and healed in the RCEC+E8 group, demonstrating that a cornea is transparent and healed when cells are injected with a laminin.

FIG. 2 shows the change in corneal thickness after cultured cornea transplantation in a rabbit bullous keratopathy model using a laminin 511-E8 fragment. As shown, the corneal thickness starts to decrease significantly after administration. When the corneal thickness was measured with an ultrasound pachymeter, the cornea was maintained in a thick state at about 1200 µm or greater (measurement limit) in the control and RCEC groups, but the corneal thickness thinned to an average of 637 µm on day 7 in the RCEC+E8 group. This is understood as transplantation of cells with a laminin regenerating the corneal endothelium and pumping and barrier functions.

FIG. 3 shows results of histological examination after cultured cornea transplantation using a laminin 511-E8 fragment. As shown in the Figure, a gene product that is expressed in normal corneal endothelial cells was expressed. Specifically, $Na^+/K^+$-ATPase indicating a pumping function and ZO-1 indicating a tight junction (barrier function) were expressed. In addition, N-cadherin indicating an adherence junction is demonstrated to be normally expressed. It was further demonstrated by phalloidin staining that cells had a monolayer polygonal morphology, which is the same as normal cells. In view of the above, it was revealed that the cells recovered normal functions.

In view of the results, it is understood that administration of a laminin or a fragment thereof with a corneal endothelial cell can significantly heal a disease or a disorder of a corneal endothelium and recover normal functions.

Example 2: Cultured Corneal Endothelium Transplantation Experiment in Rabbit Bullous Keratopathy Model with Concomitant Use of Laminin and ROCK Inhibitor Previously, it was reported that cell adhesion to a substrate is promoted by injecting cultured corneal endothelial cells into the anterior chamber with a ROCK inhibitor. In this regard, the effect of concomitant use of a laminin and a ROCK inhibitor was examined.

(Materials and Methods)
(Used Reagent Etc.)
The following reagents and the like were used in this Example.
*Cultured rabbit corneal endothelial cells (RCEC; prepared as disclosed above)
*Laminin 511 E8 fragment (same as those in Example 1; Nippi. Inc., 382-02413)
*Y-27632 ((R)-(+)-trans-(4-pyridyl)-4-(1-aminoethyl)-cyclohexanecarboxamide dihydrochloride monohydrate) (catalog number: 6880005, Calbiochem, La Jolla, Calif.)
*Rabbit bullous keratopathy model (same as those in Example 1; production method described in (Transplantation method))
*Others mentioned in the experimental approach
(Transplantation Method)
The experiment shown in FIG. 4 was conducted as follows.

A rabbit corneal endothelium was mechanically detached to make a bullous keratopathy model. Adhesion of injected cells to a substrate after 24 hours was compared between individuals injected with cultured rabbit corneal endothelial cells together with a ROCK inhibitor Y-27632 (+) (100 µM) into the anterior chamber and individuals injected with cells together with laminin 511-E8 fragments (2.1 nM) and Y-27632 (+) (100 µM). The rabbit was euthanized after 24 hours. Corneal tissue was extracted and subjected to phalloidin staining to evaluate the morphology and cell count of adhered cells.

Measurement experiments shown in FIGS. 5 to 8 were conducted as follows.
(Transplantation Method)
Tests were conducted with 4 groups of 4 rabbits, i.e., group injected with cultured corneal endothelial cells together with Y-27632 (+) (100 µM) after detaching corneal endothelial cells without detaching the Descemet's membrane, group injected with cells together with laminin 511-E8 fragments (2.1 nM) and Y-27632 (+) (100 µM) after detaching corneal endothelial cells without detaching the Descemet's membrane, group in which a bullous keratopathy model with detached Descemet's membrane was injected with cells together with Y-27632 (100 µM), and group in which a bullous keratopathy model with detached Descemet's membrane was injected with cells together with laminin 511-E8 fragments (2.1 nM) and Y-27632 (+) (100 µM).

Figure 4:
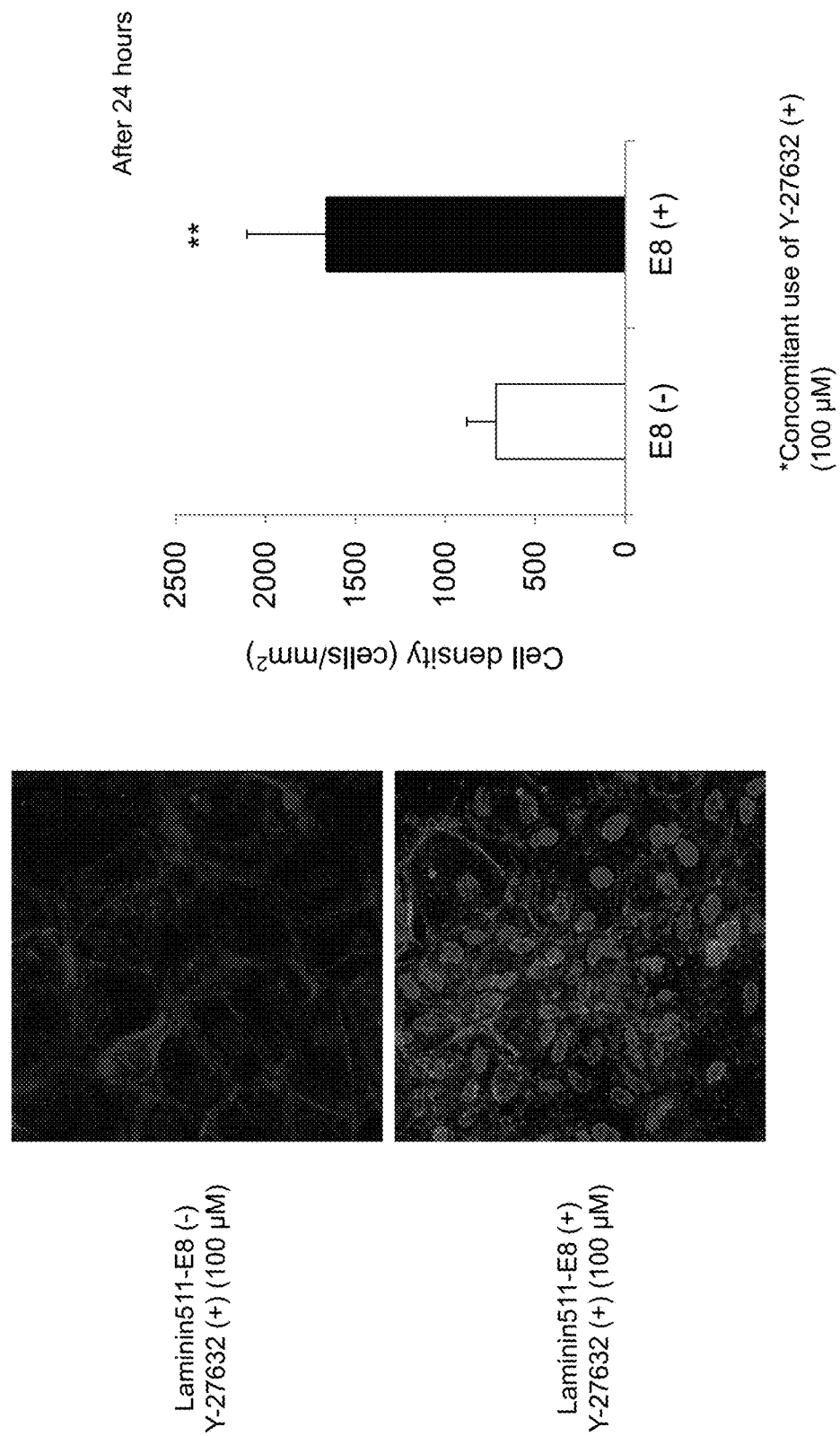
FIG. 4 shows results of examining cultured corneal endothelium transplantation in a rabbit bullous keratopathy model concomitantly using a laminin and a ROCK inhibitor. The bullous keratopathy model was produced by mechanically detaching the corneal endothelium of a rabbit. Adhesion of injected cells to the substrate after 24 hours was compared for individuals to which cultured rabbit corneal endothelial cells were injected with a ROCK inhibitor Y-27632 (+) (100 μM) into the anterior chamber and individuals to which cells, laminin 511-E8 fragments (2.1 nM), and Y-27632 (+) (100 μM) were injected. The left side shows pictures of phalloidin and DAPI staining. The top row shows a result with no laminin 511-E8 fragment and with Y-27632

(Measurement of Corneal Thickness and Ocular Pressure)
The corneal thickness was measured with an ultrasound pachymeter (SP-2000; Tomey, Nagoya, Japan). When unmeasurable, 1200 µm, which is the measurable upper limit value, was used. Further, the ocular pressure was measured with a Tonovet (M. E. Technica, Tokyo).
(Histological Examination)
The histological examination shown in FIG. 8 was conducted in the same manner as in Example 1.
(Results)
FIG. 4 shows results of cell adhesion to a substrate in cultured corneal endothelium transplantation in a rabbit bullous keratopathy model concomitantly using a laminin and a ROCK inhibitor after 24 hours. Phalloidin staining demonstrated that more cells adhered in individuals injected with cells together with laminin 511-E8 fragments (2.1 nM) and Y-27632 (+) (100 µM). Adhering cell density was also higher in individuals injected with cells, together with laminin 511-E8 fragments (2.1 nM) and Y-27632 (+) (100 µM) (on average 717.3 cells/mm$^2$ in the absence of laminin, which increased to 1662.8 cells/mm$^2$ in the presence of laminin). This is understood as a laminin further promoting cell adhesion in a living body when the laminin is concomitantly used with a ROCK inhibitor.

FIG. 5 shows pictures of the anterior ocular segment for 4 groups, which are, from the left, group injected with cultured corneal endothelial cells together with Y-27632 (+) (100 µM) after detaching corneal endothelial cells without detaching the Descemet's membrane, group injected with cells together with laminin 511-E8 fragments (2.1 nM) and Y-27632 (+) (100 µM) after detaching corneal endothelial cells without detaching the Descemet's membrane, group in which a bullous keratopathy model with detached Descemet's membrane was injected with cells together with Y-27632 (100 µM), and group in which a bullous keratopathy model with detached Descemet's membrane was injected with cells together with laminin 511-E8 fragments (2.1 nM) and Y-27632 (+) (100 µM).

FIGS. 6 and 7 are graphs showing corneal thickness and ocular pressure, respectively. Thinning of corneal thickness was delayed when the Descemet's membrane was detached compared to a case without detachment, but ultimately the corneal thickness became thin in both cases. Ocular pressure was within a normal range throughout the observation period.

FIG. 8 shows histological examination after cultured corneal endothelium transplantation using a laminin 511-E8 fragment. It was demonstrated, as shown in the drawing, that $Na^+/K^+$-ATPase (pumping function) and ZO-1 (barrier function) were expressed, and N-cadherin was also expressed normally in all groups. Phalloidin staining in the laminin 511-E8 fragment added group demonstrated that cells had a normal monolayer polygonal morphology, which is the same as normal tissue. In addition, pumping function and tight junction were expressed normally in the laminin 511-E8 fragment added group, while the adherence junction was also normal to exhibit a normal morphology. Thus, it was revealed that the cells in the laminin 511-E8 fragment added group recovered normal functions.

In view of the results, it is understood that a laminin or a fragment thereof can be used with a ROCK inhibitor and administered with corneal endothelial cells to significantly heal a disease or a disorder of a corneal endothelium and further improve a function that recovers normal functions.

Example 3: Example in a Monkey Bullous Keratopathy Model

Next, a monkey bullous keratopathy model was used as an example of primates to similarly examine the effect of concomitant use of a laminin, a ROCK inhibitor, and corneal endothelial cell transplantation.
(Materials and Methods)
(Used Reagents Etc.)
The following reagents and the like were used in this Example.
*Cultured monkey corneal endothelial cells (prepared in the same manner as in the rabbit culturing method, which is explained again below)
*Laminin 511 E8 fragment (same as Example 1; Nippi. Inc., 382-02413)
*Y-27632 ((R)-(+)-trans-(4-pyridyl)-4-(1-aminoethyl)-cyclohexanecarboxamide dihydrochloride monohydrate) (same as Example 2; catalog number: 6880005, Calbiochem, La Jolla, Calif.)
*Monkey bullous keratopathy model (produced as described below in (Transplantation method))
(Culture Method)
Monkey corneal endothelial cells (MCECs) can be obtained and cultured as follows. Specifically, the Descemet's membrane comprising the endothelial cell layer was detached from corneal tissue and was placed in 1.2 U/ml Dispase I [(Sanko Pure Chemical) catalog number: GD81060] dissolved in DMEM (Gibco-Invitrogen) and was inoculated at 37° C. After one hour, the corneal endothelial cells were detached and collected from the Descemet's membrane by pipetting, and were centrifuged for 5 minutes at 1000 rpm to remove the supernatant. A culture medium was added and mixed with the precipitated corneal endothelial cells. The entire volume thereof was seeded onto a 6-well plate coated with FNC Coating Mix. The culture medium used was DMEM (catalog number: 12320; Gibco-Invitrogen) supplemented with 10% FBS, 50 µg/ml gentamicin (catalog number: 15710-064; Invitrogen), 10 µg/ml Y-27632 (catalog number: 6880005, Calbiochem, La Jolla, Calif.), and 2 ng/ml basic fibroblast growth factor (catalog number: 13256-029; bFGF; Invitrogen). As in monkeys, previously reported lines [Tan D T et al., Lancet., 2012; 379: 1749-1761; Koizumi N et al., Exp Eye Res., 2012; 95: 60-67; Koizumi N et al., Invest Ophthalmol Vis Sci. 2007; 48: 4519-4526; Okumura N et al., Am J Pathol. 2012; 181: 268-277] were used for culturing rabbit corneal endothelial cells (CEC).

The medium was exchanged every two days. Subculture was performed at 50 to 80% confluence. The subculturing method included washing cells with $Ca^{2+}Mg^{2+}$-free PBS (PBS-; Nissui Pharmaceutical Co., Ltd., Tokyo. Japan), adding TrypLE® Select (catalog number: 12563; Invitrogen), and incubating for 5 minutes at 37° C. After the cells were detached and collected from the plate and were centrifuged for 5 minutes at 1000 rpm, a culture medium was added to produce a cell suspension. The cells were seeded at a density of 1:2 on a plate coated with FNC Coating Mix.
(Transplantation Method)
A cynomolgus monkey corneal endothelium was mechanically detached using a 20 gauge silicone needle (Soft Tapered Needle; Inami & Co., Ltd., Tokyo, Japan) to make a bullous keratopathy model. In FIG. 9, 5.0=105 cultured monkey corneal endothelial cells were injected with DMEM containing laminin 511-E8 fragments adjusted to a concentration of 2.1 nM into the anterior chamber of the bullous keratopathy model, which was maintained in a face-down posture for three hours. In FIG. 10, the Descemet's membrane was detached in a produced bullous keratopathy model and, similarly, $5.0\times10^5$ cultured monkey corneal endothelial cells were injected with DMEM containing laminin 511-E8 fragments adjusted to a concentration of 2.1 nM into the anterior chamber of the bullous keratopathy model, which was maintained in a face-down posture for three hours.
(Measurement of Corneal Thickness)
The corneal thickness was measured with an ultrasound pachymeter (SP-2000; Tomey, Nagoya, Japan). When unmeasurable, 1200 µm, which is the measurable upper limit value, was used.
(Results)
Results are shown in FIGS. 9 to 10. FIG. 9 shows pictures of the anterior ocular segment after cultured corneal endothelium transplantation in monkey bullous keratopathy model subjected to concomitant use of laminin 511-E8 fragments. It was found that the laminin or a fragment thereof of the invention can heal bullous keratopathy by administration with corneal endothelial cells with a ROCK inhibitor in primate models, which have significantly restricted corneal endothelial growth in a living body. Meanwhile, FIG. 10 shows pictures of the anterior ocular segment after detaching the Descemet's membrane and transplanting cultured corneal endothelial cells concomitantly with laminin 511-E8 fragments in a monkey bullous keratopathy model. The cornea was not transparent or healed in a model where cynomolgus monkey corneal endothelial cells were mechanically scraped off. While the cornea was transparent and healed in a rabbit bullous keratopathy model, a therapeutic effect was not observed in a cynomolgus monkey model. This suggests the possibility that a corneal endothelium is not regenerated depending on the animal species because adhesion of transplanted cells to the cornea decreases when the Descemet's membrane is detached. FIG. 11 shows the change in corneal thickness in individuals subjected to transplantation without Descemet's membrane detachment and individuals subjected to transplantation with Descemet's membrane detachment in a graph. The corneal thickness did not become thin in the Descemet's membrane detachment group, whereas it did without Descemet's membrane detachment.

Example 4: Example of Therapy with Laminin Coating in Descemet's Membrane Detached Subject Next, improvement was confirmed in the effect of concomitant use of a laminin, a ROCK inhibitor, and corneal endothelial cell transplantation by separately coating stroma on the back side of a cornea exposed by Descemet's membrane detachment with a laminin to confirm that.
(Materials and Methods)
(Used Reagents Etc.)
The following reagents and the like were used in this Example.
*Cultured monkey corneal endothelial cells (prepared in the same manner as in Example 3)
*Laminin 511-E8 fragment (same as Example 1; Nippi. Inc., 382-02413)
*Y-27632 ((R)-(+)-trans-(4-pyridyl)-4-(1-aminoethyl)-cyclohexanecarboxamide dihydrochloride monohydrate) (same as Example 2; catalog number: 6880005, Calbiochem, La Jolla, Calif.)
(Method)
A cynomolgus monkey corneal endothelium was mechanically detached using a 20 gauge silicone needle (Soft Tapered Needle; Inami & Co., Ltd., Tokyo, Japan) to make a bullous keratopathy model. The Descemet's membrane was detached in the produced bullous keratopathy model. Laminin 511-E8 fragments were injected into the anterior chamber of the bullous keratopathy model at a concentration of 21 nM and the model was left standing for one hour. The corneal stroma exposed by detaching the Descemet's membrane was coated thereby in the living body. Subsequently, $5.0 \times 10^5$ cultured monkey corneal endothelial cells were injected with DMEM containing laminin 511-E8 fragments adjusted to a concentration of 2.1 nM into the anterior chamber of the bullous keratopathy model, which was maintained in a face-down posture for three hours as in Example 3.
(Results)
Results are shown in FIG. 12. As shown in FIG. 12, detachment of the Descemet's membrane followed by injection of laminin 511-E8 fragments into the anterior chamber at a concentration of 21 nM to coat the corneal stroma resulted in the cornea being transparent and healed, which was not attained without coating (FIG. 10). This demonstrates that injection of a laminin with a cell suspension can not only promote cell adhesion, but also engraftment of cells in a living body by use thereof as a coating agent in a living body.

Example 5: Effect of Integrin on Adhesion of Corneal Endothelial Cell

In this Example, the effect of various integrins on adhesion of corneal endothelial cells was examined.
(Materials and Methods)
(Used Reagents Etc.)
The following reagents and the like were used in this Example.
*Control refers to a laminin 511-E8 fragment free group.
*Mouse IgG (DAKO, X0931)
*Anti-integrin α3 (Millipore, MAB1952Z-20)
*Anti-integrin α6 (Millipore, MAB1378-20)
*Anti-integrin α2 (Millipore, MAB1950Z-20)
*Anti-integrin β1 (R&D Systems, MAB17781)
*For anti-integrin α3β1 and anti-integrin α6β1, a combination of the above was used.
*Laminin 511-E8 fragment (same as the above Examples)
(Method)
The medium was completely removed from a culture dish culturing human corneal endothelial cells. The cells were washed twice with PBS (−). After washing, phosphate buffer was added, and the mixture was incubated for 5 minute at 37° C. (5% $CO_2$). Subsequently, PBS (−) was removed and TrypLE™ Select (10×) (Life Technologies, A12177-01) was added. The mixture was incubated for 10 minutes at 37° C. (5% $CO_2$). Opti-MEMI (Life Technologies, 31985-070) was then added to collect the cells. After collecting the cells, the cells were centrifuged for 3 minutes at 1200 rpm to make a cell suspension with Opti-MEM I. At this time, a laminin 511-E8 fragment free group was prepared as a control, as well as a group supplemented with laminin 511-E8 fragments so that the final concentration was 2.1 nM. At the same time, mouse IgG and integrin neutralizing antibody were added to the laminin 511-E8 fragment added group to adjust the final concentration to 2 μg/ml. After the adjustment, cells were seeded on a 96-well plate at 5000 cells/well and were incubated for 24 hours at 37° C. (5% $CO_2$). After 24 hours of seeding, the medium was completely removed and the cells were washed twice with PBS (−). After washing, a medium and CellTiter-Glo Luminescent Cell Viability Assay (Promega Corporation, Madison, Wis.) were added at a ratio of 1:1. The mixture was shaken in the dark for 2 minutes and was then left standing for 10 minutes. Measurements were taken thereafter. 24 h, *p<0.01, Dunnet's test, n=6.
(Results)
Results are shown in FIG. 13. As shown, addition of laminin 511-E8 fragments to a medium upon seeding promoted adhesion of corneal endothelial cells for the control, but cell adhesion was suppressed to the same level as the control by neutralizing antibodies of integrin β1.

Example 6: Relationship Between Activation of Cell Adhesion Associated Protein and Integrin Next, this Example demonstrated that activation of a cell adhesion associated protein is mediated by an integrin.
(Materials and Methods)
(Reagents Etc.)
In principle, the same conditions as those in Example 5 were used.
*Mouse IgG (same as in Example 5)
*Anti-integrin $α_3$ (same as in Example 5)
*Anti-integrin $α_6$ (same as in Example 5)
*Anti-integrin $α_2$ (same as in Example 5)
*Anti-integrin $β_1$ (same as in Example 5)
*Anti-integrin $α_3β_1$ (same as in Example 5)
*Anti-integrin $α_6β_1$ (same as in Example 5)
(Method)
The medium was completely removed from a culture dish culturing human corneal endothelial cells. The cells were washed twice with PBS (−). After washing, phosphate buffer was added, and the mixture was incubated for 5 minute at 37° C. (5% $CO_2$). Subsequently, PBS (−) was removed and TrypLE™ Select (10×) (Life Technologies, A12177-01) was added. The mixture was incubated for 10 minutes at 37° C. (5% $CO_2$). Opti-MEMI (Life Technologies, 31985-070) was then added to collect the cells. After collecting the cells, the cells were centrifuged for 3 minutes at 1200 rpm to make a cell suspension with Opti-MEM I. At this time, a laminin 511-E8 fragment free group was prepared as a control, as well as a group supplemented with laminin 511-E8 fragments so that the final concentration was 2.1 nM. At the same time, mouse IgG and integrin neutralizing antibody were added to the laminin 511-E8 fragment added group to adjust the final concentration to 2 μg/ml. After adjustment, cells were seeded on a 12-well plate at $1 \times 10^5$ cells/well and proteins were collected after three hours of seeding. Western blot was used to detect Phospho-FAK (Cell Signaling TECHNOLOGY, 8556S), FAK (Cell Signaling TECHNOL- OGY, 32855), and p-Paxillin (Cell Signaling TECHNOLOGY, 2541S). The dilution factor for each antibody was 1:1000. The densitometry was quantified using Image J.
(Results)
Results are shown in FIG. 14. As shown, p-FAK was promoted by laminin 511-E8 fragments after three hours of seeding, but was suppressed to the same level as the control by neutralizing antibodies of integrin β1. p-Paxillin was also promoted by laminin 511-E8 fragments, but was suppressed to the same level as the control by neutralizing antibodies of integrin β1. In view of the above, it is understood that E8 promotes cell adhesion by activating an adhesion associated protein via an integrin.

In view of Examples 5 and 6, earlier cell adhesion relative to fragment free cells is observed by adding laminin 511-E8 fragments. The number of adhering cells after 24 hours significantly increased to 137.3±2.8% (p<0.01). Further, cell adhesion action by laminin 511-E8 fragments was suppressed by neutralizing antibodies of integrin $\alpha_3\beta_1$ and $\alpha_6\beta_1$ such that the action was at the same level as laminin 511-E8 fragment free cells (p<0.01). Phosphorylation of FAK was promoted by laminin 511-E8 fragments, but suppressed by an integrin neutralizing antibody. Thus, it is understood that laminin 511 binds to an integrin and promotes phosphorylation of FAK to promote substrate adhesion of corneal endothelial cells. Therefore, it is understood that laminins such as laminin 511-E8 fragments can be applied in corneal endothelial cell transplantation.

Example 7: Formulation Example: Laminin-Cell Mixture Formulation

In this Example, a therapeutic solution containing the agent of the invention is manufactured as follows as a Formulation Example.

The following solution is prepared by a conventional method.
Laminin 511, laminin 521 and/or a fragment thereof (0.75 μg/cm$^2$)
  Final concentration is 2.1 nM
Cultured corneal endothelial cells
  (appropriate amount of cells prepared according to Example 1 or the like)
Suitable Buffer
  appropriate amount
Total Quantity
  100 mL

Example 8: Formulation Example: Laminin Coating Composition

In this Example, a coating solution comprising the agent of the invention is manufactured as follows as a Formulation Example.

A coating solution is prepared as shown below by a conventional method.
Laminin 511, laminin 521 and/or a fragment thereof (0.75 μg/cm$^2$)
  Final concentration is 21 nM
Suitable Buffer
  appropriate amount
Total Quantity
  100 mL Each component can be obtained as described in Examples 1 to 4.

As described above, the present invention has been exemplified using preferable embodiments of the present invention. However, it is understood that the scope of the present invention should be construed only by the scope of claims. It is understood that patents, patent applications and literatures cited herein are incorporated herein by reference, as if the contents thereof are specifically described herein. The present application claims priority to Japanese Patent Application No. 2014-222947 filed on Oct. 31, 2014, the entire content of which is incorporated herein by reference.

INDUSTRIAL APPLICABILITY

The present invention allows novel ophthalmic therapy, especially novel therapy of corneal endothelial cells (especially human corneal endothelial cells). In particular, the present invention can result in near complete recovery of bullous keratopathy, such that the present invention is particularly useful in the pharmaceutical industry.

SEQUENCE LISTING FREE TEXT

SEQ ID NO: 1: laminin α5 chain nucleic acid sequence (NM_005560)
SEQ ID NO: 2: laminin α5 chain amino acid sequence (NP_005551)
SEQ ID NO: 3: laminin β1 chain nucleic acid sequence (NM_002291)
SEQ ID NO: 4: laminin β1 chain amino acid sequence (NP_002282)
SEQ ID NO: 5: laminin β2 chain nucleic acid sequence (NM_002292)
SEQ ID NO: 6: laminin β2 chain amino acid sequence (NP_002283)
SEQ ID NO: 7: laminin γ1 chain nucleic acid sequence (NM_002293)
SEQ ID NO: 8: laminin γ1 chain amino acid sequence (NP_002284)

The invention claimed is:

1. A method for treating a disease, a disorder, or a condition of a corneal endothelium of a subject, comprising administering a corneal endothelial cell suspension comprising a therapeutically effective amount of at least one agent selected from the group consisting of laminins and fragments thereof to the subject, wherein the laminins and fragments thereof comprise an α5 chain and/or a γ1 chain.

2. The method of claim 1, wherein the laminins comprise an Arginine-Glycine-Aspartic Acid (RGD) sequence.

3. The method of claim 1, wherein the laminins comprise laminin 511 (α5β1γ1) and laminin 521 (α5β2γ1).

4. The method of claim 1, wherein the fragments increase cell adhesion capability of a corneal endothelial cell.

5. The method of claim 1, wherein the agent is laminin 511, laminin 521, or a laminin 511-E8 fragment.

6. The method of claim 1, wherein the corneal endothelium is from a primate.

7. The method of claim 1, wherein the disease, disorder, or condition of the corneal endothelium is selected from the group consisting of Fuchs' corneal endothelial dystrophy, corneal endotheliitis, trauma, and disorders and conditions from an ophthalmic surgery.

8. The method of claim 1, wherein the disease, disorder, or condition of the corneal endothelium is selected from the group consisting of photophobia, blurred vision, visual impairment, ophthalmalgia, epiphora, hyperemia, pain, bullous keratopathy, eye discomfort, diminished contrast, glare, edema of the corneal stroma, and corneal turbidity.

9. The method of claim 1, wherein the corneal endothelium comprises a corneal endothelial layer, a Descemet's membrane, or both.

10. The method of claim 1, wherein the corneal endothelium has a Descemet's membrane in a detached state.

11. The method of claim 1, further comprising administering a Rho kinase (ROCK) inhibitor to the subject.

12. The method of claim 11, wherein the ROCK inhibitor is selected from the group consisting of Y-27632 ((R)-(+)-trans-(4-pyridyl)-4-(1-aminoethyl)-cyclohexanecarboxamide dihydrochloride monohydrate) and a pharmaceutically acceptable salt thereof.

13. The method of claim 1, wherein the step of administering comprises injecting the suspension into an eye of the subject, thereby contacting the agent with tissue in the eye.

14. The method of claim 13, wherein the agent is present at a concentration of 21 nM or greater in the suspension.

15. The method of claim 13, wherein the agent is present in the suspension at a concentration of 2.1 nM or greater.

* * * * *

UNITED STATES PATENT AND TRADEMARK OFFICE
CERTIFICATE OF CORRECTION

PATENT NO. : 11,633,477 B2
APPLICATION NO. : 15/523231
DATED : April 25, 2023
INVENTOR(S) : Noriko Koizumi et al.

Page 1 of 1

It is certified that error appears in the above-identified patent and that said Letters Patent is hereby corrected as shown below:

On the Title Page

Page 2, item (56) right column, Lines 65-67, the reference "Europen Patent Office, Communication Pursuant to Article 94 (3) EPC in European Patent Application No. 15854105.2 (dated Oct. 14, 2019)," should read "European Patent Office, Communication Pursuant to Article 94(3) EPC in European Patent Application No. 15854105.2 (dated Oct. 14, 2019)."

In the Claims

In Claim 1, Column 111, at Line 57, "y1 chain" should read "γ1 chain."

Signed and Sealed this
Eleventh Day of July, 2023

Katherine Kelly Vidal
*Director of the United States Patent and Trademark Office*